(12) United States Patent
Tu et al.

(10) Patent No.: US 12,214,010 B2
(45) Date of Patent: Feb. 4, 2025

(54) DESMOPRESSIN ORAL COMPOSITIONS

(71) Applicant: Tulex Pharmaceuticals Inc., Cranbury, NJ (US)

(72) Inventors: Yu-Hsing Tu, West Windsor, NJ (US); Kalyan Kathala, Monroe, NJ (US); Romona Bhattacharya, Franklin Park, NJ (US); Yingjun Fan, Plainsboro, NJ (US); Ashok Perumal, Monmouth Junction, NJ (US)

(73) Assignee: Tulex Pharmaceuticals Inc., Cranbury, NJ (US)

( * ) Notice: Subject to any disclaimer, the term of this patent is extended or adjusted under 35 U.S.C. 154(b) by 0 days.

(21) Appl. No.: 18/625,923

(22) Filed: Apr. 3, 2024

(65) Prior Publication Data

US 2024/0335501 A1 Oct. 10, 2024

Related U.S. Application Data

(60) Provisional application No. 63/457,005, filed on Apr. 4, 2023.

(51) Int. Cl.

| | |
|---|---|
| *A61K 38/10* | (2006.01) |
| *A61K 9/00* | (2006.01) |
| *A61K 38/095* | (2019.01) |
| *A61K 47/10* | (2017.01) |
| *A61K 47/12* | (2006.01) |
| *A61K 47/14* | (2017.01) |
| *A61K 47/18* | (2017.01) |
| *C07K 7/16* | (2006.01) |

(52) U.S. Cl.
CPC .......... *A61K 38/095* (2019.01); *A61K 9/0053* (2013.01); *A61K 47/10* (2013.01); *A61K 47/12* (2013.01); *A61K 47/14* (2013.01); *A61K 47/183* (2013.01); *C07K 7/16* (2013.01)

(58) Field of Classification Search
None
See application file for complete search history.

(56) References Cited

U.S. PATENT DOCUMENTS

| | | | |
|---|---|---|---|
| 5,047,398 | A | 9/1991 | Hagstam et al. |
| 7,799,761 | B2 | 9/2010 | Fein |
| 8,993,521 | B2 | 3/2015 | Carbajal Navarro et al. |
| 11,020,448 | B2 | 6/2021 | Klein et al. |
| 2003/0119728 | A1 | 6/2003 | Scheidl et al. |
| 2003/0216302 | A1* | 11/2003 | Bhowmick .......... A61K 9/0019 |
| | | | 514/10.9 |
| 2011/0251123 | A1* | 10/2011 | Carbajal Navarro ..... A61P 7/12 |
| | | | 514/10.9 |
| 2011/0251125 | A1 | 10/2011 | Bay et al. |
| 2017/0106043 | A1 | 4/2017 | Nilsson et al. |
| 2018/0271946 | A1 | 9/2018 | Houchin et al. |
| 2021/0161810 | A1 | 6/2021 | Fein |

FOREIGN PATENT DOCUMENTS

| | | |
|---|---|---|
| WO | WO-9501185 A1 | 1/1995 |
| WO | WO-2004014411 A1 | 2/2004 |
| WO | WO-2009027561 A2 | 3/2009 |

OTHER PUBLICATIONS

Shaikh et al., PharmaTutor 4:25-34 (2016) (Year: 2016).*
Rowe et al., eds., "Benzoic Acid," in: Handbook of Pharmaceutical Excipients, 6th Ed., Pharmaceutical Press and the American Pharmacists Association, p. 61-63 (2009) (Year: 2009).*
"Buffers", U. Texas Austin, available online at https://ch302.cm.utexas.edu/chemEQ/buffers/selector.php?name=buffers, 2 pages (2013) (Year: 2013).*
Allen, Howard C et al., Pharmaceutical Dosage Forms and Drug Delivery Systems. Seventh Edition, Lippincott Williams & Wilkins (1999).
Comar. Packaging and Medical Solutions. Retrieved from Internet URL : www.comar.com/ on Feb. 9, 2023.
Drug Plastics. Pharmaceutical & Lifestyle Packaging. Retrieved from www.drugplastics.com/ on Feb. 9, 2023.
Gennaro, Alfonso R. Remingtons Pharmaceutical Sciences: The Science and Practice of Pharmacy, 20th Ed., Lippincott Williams & Wilkins. p. 1 (2000).
Hoover, John E et al. Remington's Pharmaceutical Sciences. Mack Publishing Company vol. 65(6):933 (1976).
Liberman, Herbert A et al. Pharmaceutical Dosage Forms: Parental Medications. Marcel Decker, New York: pp. 1-4 (1980).
No Author, Compound Evaluation Form, Desmopressin, 2020.
No Author, Ddavp tablets, Pharmaceutical Label, (2007).
No Author, Desmopressin Acetate, Pharmaceutical Label, (2021).
No Author, Guidance for Industry, Statistical Approaches to Establishing Bioequivalence, US Department of Health and Human Services, 2001.
No Author, Pharmacopeia (USP) 659 "Packaging and Storage Requirements" Rev. Bull. May 1, 2017.
O.Berk. Packaging Solutions. Retrieved from Internet URL: www.oberk.com/ on Feb. 9, 2023.

* cited by examiner

*Primary Examiner* — Thea D'Ambrosio
(74) *Attorney, Agent, or Firm* — Wilson Sonsini Goodrich & Rosati

(57) ABSTRACT

Provided herein are desmopressin oral liquid formulations. Also provided herein are methods of making and using desmopressin oral liquid compositions for the treatment of certain diseases including diabetes insipidus, enuresis, hemophilia A, von willebrand disease, high blood urea levels and others.

22 Claims, 1 Drawing Sheet
Specification includes a Sequence Listing.

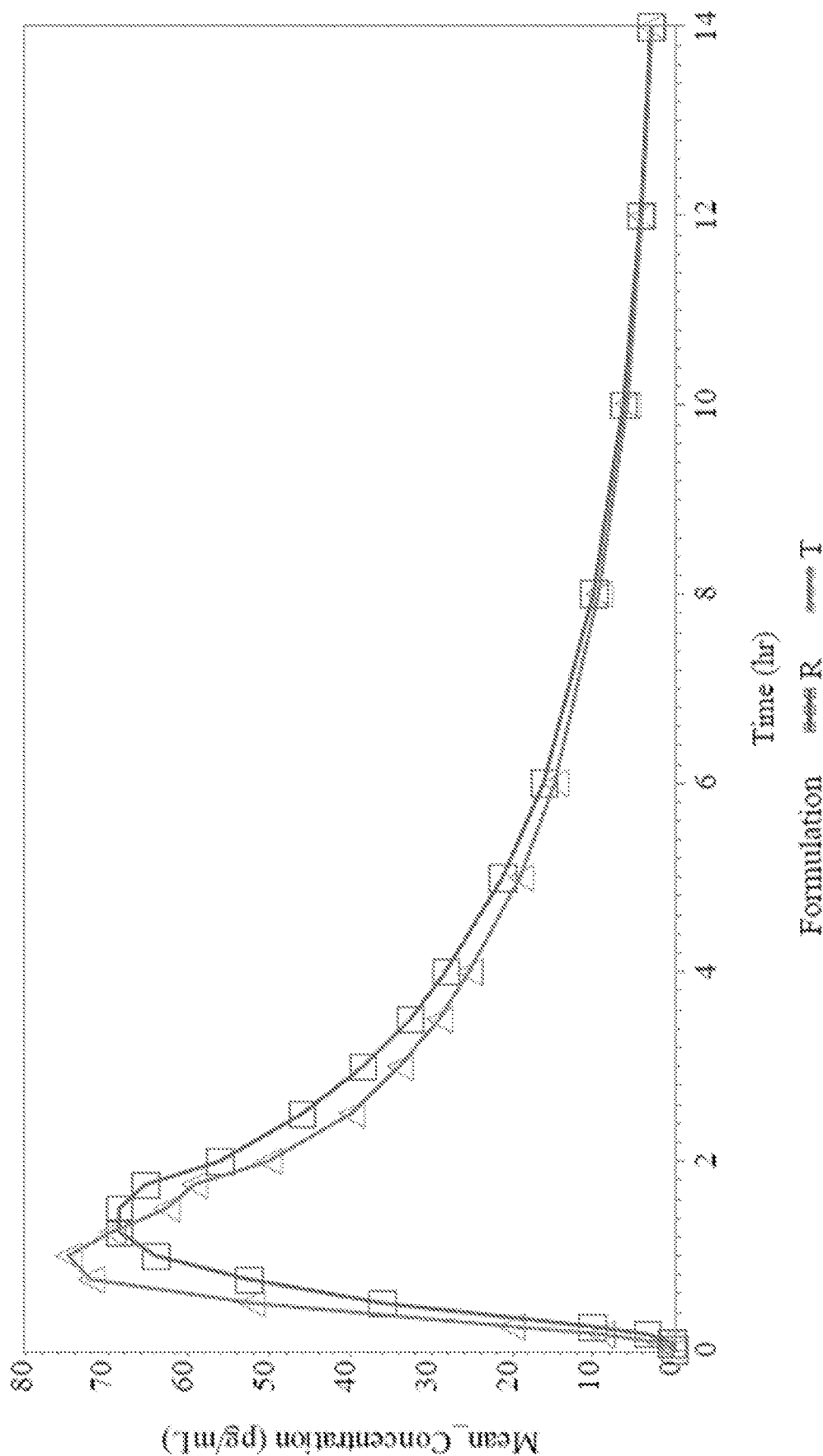

DESMOPRESSIN ORAL COMPOSITIONS

CROSS REFERENCE TO RELATED APPLICATIONS

This application claims the benefit of U.S. Provisional Patent Application No. 63/457,005, filed on Apr. 4, 2023, which is incorporated herein by reference in its entirety.

REFERENCE TO A SEQUENCE LISTING XML

This application contains a Sequence Listing which has been submitted electronically in XML format. The Sequence Listing XML is incorporated herein by reference. Said XML file, created on Aug. 15, 2024, is named 64483-703.201_SL.xml and is 3,032 bytes in size.

BACKGROUND

Desmopressin is a synthetic analogue of the natural pituitary hormone 8-arginine vasopressin (ADH), an antidiuretic hormone affecting renal water conservation, that has been modified by deamination of 1-cysteine and substitution of 8-L-arginine by 8-D-arginine. Desmopressin acetate is currently available in the United States in 0.10 mg and 0.20 mg tablets, and in nasal formulations. There remains a need for a desmopressin oral liquid formulation.

SUMMARY

In some aspects, disclosed herein is a liquid pharmaceutical composition comprising a) desmopressin free base or a pharmaceutically acceptable salt thereof in an amount of about 0.01 mg/mL to about 0.1 mg/mL; b) a two-component, dual-functional, preservative-buffer system; and c) water. In some embodiments, the liquid pharmaceutical composition is an oral solution. In some embodiments, the liquid pharmaceutical composition is stable after stored at room temperature for at least 2 months. In some embodiments, desmopressin free base or a pharmaceutically acceptable salt thereof is present in an amount of about 0.01 mg/mL to about 0.08 mg/mL, about 0.03 mg/mL to about 0.07 mg/mL, or about 0.04 mg/mL to about 0.06 mg/mL. In some embodiments, desmopressin free base or a pharmaceutically acceptable salt thereof is present in an amount of about 0.05 mg/mL. In some embodiments, the pharmaceutically acceptable salt of desmopressin is desmopressin acetate. In some embodiments, desmopressin acetate is present in an amount of about 0.05 mg/mL. In some embodiments, desmopressin free base or a pharmaceutically acceptable salt thereof is present in an amount of about 0.05 mg/mL. In some embodiments, the pharmaceutically acceptable salt of desmopressin is desmopressin acetate. In some embodiments, desmopressin acetate is present in an amount of about 0.05 mg/mL. In some embodiments, the two-component, dual-functional, preservative-buffer system comprises an acidic preservative and a salt of the acidic preservative (e.g., a sodium salt or a potassium salt). In some embodiments, the salt comprises a sodium salt or a potassium salt. In some embodiments, the acidic preservative and the salt of the acidic preservative are in a weight ratio of from about 1:50 to about 50:1, from about 1:40 to about 20:1, from about 1:30 to about 1:1, from about 1:20 to about 1:5, from about 1:15 to about 1:5, or from about 1:10 to about 1:6. In some embodiments, the two-component, dual-functional, preservative-buffer system is selected from sorbic acid/sorbate, benzoic acid/benzoate, propionic acid/propionate, citric acid/citrate, acetic acid/acetate, lactic acid/lactate, formic acid/formate, and ascorbic acid/ascorbate. In some embodiments, the two-component, dual-functional, preservative-buffer system is sorbic acid/sorbate or benzoic acid/benzoate. In some embodiments, two-component, dual-functional, preservative-buffer system is benzoic acid and sodium benzoate. In some embodiments, benzoic acid and sodium benzoate are present in an amount of from about 0.01% w/v to about 0.6% w/v, about 0.01% w/v to about 0.5% w/v, about 0.05% w/v to about 0.45% w/v, about 0.08% w/v to about 0.4% w/v, about 0.1% w/v to about 0.35% w/v, about 0.15% w/v to about 0.32% w/v, or about 0.18% w/v to about 0.32% w/v. In some embodiments, benzoic acid and sodium benzoate are present in an amount of from 0.01% w/v to about 0.4% w/v, about 0.08% w/v to about 0.32% w/v, about 0.1% w/v to about 0.3% w/v, about 0.15% w/v to about 0.25% w/v, or about 0.16% w/v to about 0.22% w/v. In some embodiments, the two-component, dual-functional, preservative-buffer system is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.3% w/v or less, or about 0.2% w/v or less. In some embodiments, the two-component, dual-functional, preservative-buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D. In some embodiments, benzoic acid and sodium benzoate are present in an amount of about 0.18% w/v to about 0.32% w/v and provide a pH that is from about 4.0 to about 6.0, about 4.5 to about 5.5, about 4.5 to about 5.0, or about 5.0. In some embodiments, benzoic acid and sodium benzoate are present in an amount of about 0.18% w/v to about 0.22% w/v and provide a pH that is from about 4.0 to about 6.0, about 4.5 to about 5.5, or about 5.0. In some embodiments, the liquid pharmaceutical composition is ready-to-use without dilution or addition of any further components to the liquid pharmaceutical composition.

In some aspects, disclosed herein is a liquid pharmaceutical composition comprising a) desmopressin free base or a pharmaceutically acceptable salt thereof in an amount of about 0.01 mg/mL to about 0.1 mg/mL; b) a buffer system in an amount of about 0.6% w/v or less; and c) water. In some embodiments, the liquid pharmaceutical composition comprises a) desmopressin free base or a pharmaceutically acceptable salt thereof in an amount of about 0.01 mg/mL to about 0.1 mg/mL; b) a buffer system in an amount of about 0.32% w/v or less; and c) water. In some embodiments, the liquid pharmaceutical composition is an oral solution. In some embodiments, the buffer system also functions as a preservative. In some embodiments, the liquid pharmaceutical composition is stable after stored at room temperature for at least 2 months. In some embodiments, desmopressin free base or a pharmaceutically acceptable salt thereof is present in an amount of about 0.01 mg/mL to about 0.08 mg/mL, about 0.03 mg/mL to about 0.07 mg/mL, or about 0.04 mg/mL to about 0.06 mg/mL. In some embodiments, the buffer system comprises an acid (e.g., a weak acid) and its conjugate base. In some embodiments, the acid is an acidic preservative. In some embodiments, the buffer system comprises the acidic preservative and a salt of the acidic preservative (e.g., a sodium salt or a potassium salt) or a combination thereof. In some embodiments, the salt comprises a sodium salt or a potassium salt. In some embodiments, the buffer system comprises a combination of the acidic preservative and the salt of the acidic preservative in a weight ratio of from about 1:50 to about 1:1, from about 1:40 to about 1:1, from about 1:30 to about 1:4, from about 1:20 to about 1:5, from about 1:15 to about 1:5, or from about 1:10 to about 1:6. In some embodiments, the buffer system comprises a combination of the acidic preservative and the salt of the acidic preservative in a weight ratio of from about 1:50 to about 1:1, from about 1:40 to about 1:1, from about 1:30 to about 1:4, from about 1:20 to about 1:5, from about 1:15 to about 1:5, or from about 1:10 to about 1:6, from about 1:6 to about 1:1, from about 1:3 to about 1:1, or from about 1:2 to about 1:1. In some embodiments, the buffer system comprises sorbic acid, sorbate salts, benzoic acid, benzoate salts, propionic acid, propionate salts, citric acid, citrate salts, acetic acid, acetate salts, lactic acid, lactate salts, formic acid, formate salts, ascorbic acid, ascorbate salts or any combination thereof. In some embodiments, the buffer system comprises benzoic acid, a benzoate salt (e.g., sodium benzoate), or a combination thereof. In some embodiments, the buffer system comprises benzoic acid and sodium benzoate, and optionally. In some embodiments, benzoic acid and sodium benzoate are present in an amount of about 0.08% w/v to about 0.32% w/v, about 0.1% w/v to about 0.3% w/v, about 0.15% w/v to about 0.25% w/v, or about 0.16% w/v to about 0.22% w/v. In some embodiments, benzoic acid and sodium benzoate are present in an amount of about 0.08% w/v to about 0.6% w/v, about 0.1% w/v to about 0.5% w/v, about 0.15% w/v to about 0.4% w/v, or about 0.16% w/v to about 0.32% w/v. In some embodiments, the buffer system is present in an amount of about 0.6% w/v or less, about 0.5% w/v or less, about 0.4% w/v or less, or about 0.32% w/v or less. In some embodiments, the buffer system is present in an amount of about 0.3% w/v or less, about 0.25% w/v or less, or about 0.2% w/v or less. In some embodiments, the buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D. In some embodiments, benzoic acid and sodium benzoate are present in an amount of about 0.18% w/v to about 0.22% w/v and provide a pH that is from about 4.0 to about 6.0, about 4.5 to about 5.5, or about 5.0. In some embodiments, benzoic acid and sodium benzoate are present in an amount of about 0.18% w/v to about 0.32% w/v and provide a pH that is from about 4.0 to about 6.0, about 4.5 to about 5.5, about 4.5 to about 5.0, or about 5.0.

In some aspects, disclosed herein is a liquid pharmaceutical composition, comprising a) desmopressin acetate; b) sodium benzoate; c) benzoic acid; and d) water. In some embodiments, the liquid pharmaceutical composition is an oral solution. In some embodiments, the liquid pharmaceutical composition comprises a) desmopressin acetate in an amount of about 0.01 to about 0.1 mg/mL; b) sodium benzoate in an amount of about 0.18% w/v to about 0.4% w/v; c) benzoic acid in an amount of about 0.03% w/v to about 0.04% w/v; and d) water. In some embodiments, the liquid pharmaceutical composition comprises a) desmopressin acetate in an amount of about 0.025 to about 0.075 mg/mL; b) sodium benzoate in an amount of about 0.2% w/v to about 0.35% w/v; c) benzoic acid in an amount of about 0.03% w/v to about 0.04% w/v; and d) water. In some embodiments, the liquid pharmaceutical composition comprises a) desmopressin acetate in an amount of about 0.05 mg/mL; b) sodium benzoate in an amount of about 0.25% w/v to about 0.3% w/v; c) benzoic acid in an amount of about 0.034% w/v; and d) water. In some embodiments, the liquid pharmaceutical composition comprises a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition consists essentially of a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition consists of a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition comprises a) desmopressin acetate in an amount of about 0.01 to about 0.05 mg/mL; b) sodium benzoate in an amount of about 0.08% w/v to about 0.25% w/v; c) benzoic acid in an amount of about 0.01% w/v to about 0.03% w/v; and d) water. In some embodiments, the liquid pharmaceutical composition comprises a) desmopressin acetate in an amount of about 0.05 mg/mL; b) sodium benzoate in an amount of about 0.16% w/v to about 0.2% w/v; c) benzoic acid in an amount of about 0.02% w/v; and d) water. In some embodiments, the liquid pharmaceutical composition consists essentially of a) desmopressin acetate in an amount of about 0.05 mg/mL; b) sodium benzoate in an amount of about 0.16% w/v to about 0.2% w/v; c) benzoic acid in an amount of about 0.02% w/v; and d) water. In some embodiments, the liquid pharmaceutical composition consists of a) desmopressin acetate in an amount of about 0.05 mg/mL; b) sodium benzoate in an amount of about 0.16% w/v to about 0.2% w/v; c) benzoic acid in an amount of about 0.02% w/v; and d) water. In some embodiments, the liquid pharmaceutical composition is ready-to-use without dilution or addition of any further components to the liquid pharmaceutical composition.

In some aspects, disclosed herein is a liquid pharmaceutical composition comprising desmopressin free base or a pharmaceutically acceptable salt thereof in an amount of about 0.01 mg/mL to about 0.1 mg/mL and wherein the liquid pharmaceutical composition does not comprise malic acid or malate. In some embodiments, the liquid pharmaceutical composition is an oral solution that is ready-to-use without dilution or addition of any further components for administration in pediatric population. In some embodiments, the liquid pharmaceutical composition is stable after stored at room temperature for at least 2 months.

In any one of the foregoing or related aspects, the liquid pharmaceutical composition further comprises a sweetener. In some embodiments, the sweetener is a sugar (e.g., glucose, fructose, sucrose, lactose, maltose) or sugar alcohol (e.g., xylitol, mannitol, lactitol, maltitol, or sorbitol). In some embodiments, the sweetener comprises glucose, fructose, sucrose, xylitol, tagatose, sucralose, maltitol, isomaltulose, hydrogenated isomaltulose, lactitol, sorbitol, erythritol, trehalose, maltodextrin, or polydextrose. In some embodiments, the sweetener comprises sorbitol or maltitol, or a combination thereof.

In some aspects, disclosed herein is a liquid pharmaceutical composition comprising desmopressin free base or a pharmaceutically acceptable salt thereof in an amount of about 0.01 mg/mL to about 0.1 mg/mL and wherein the liquid pharmaceutical composition does not comprise a sweetener. In some embodiments, the liquid pharmaceutical composition is an oral solution that is ready-to-use without dilution or addition of any further components for administration in pediatric population. In some embodiments, the liquid pharmaceutical composition is stable after stored at room temperature for at least 2 months. In some embodiments, the liquid pharmaceutical composition comprises malic acid or malate.

In any one of the foregoing or related aspects, desmopressin free base or a pharmaceutically acceptable salt thereof is present in an amount of about 0.01 mg/mL to about 0.08 mg/mL, about 0.03 mg/mL to about 0.07 mg/mL, or about 0.04 mg/mL to about 0.06 mg/mL. In some embodiments, desmopressin free base or a pharmaceutically acceptable salt thereof is present in an amount of about 0.05 mg/mL. In some embodiments, the pharmaceutically acceptable salt of desmopressin is desmopressin acetate. In some embodiments, desmopressin acetate is present in an amount of about 0.05 mg/mL.

In any one of the foregoing or related aspects, the liquid pharmaceutical composition comprises water and optionally further comprises a liquid carrier. In some embodiments, water is present in the liquid pharmaceutical composition in an amount of about 10% to about 99.9% w/v, about 20% to about 99.9% w/v, about 40% to about 99.9% w/v, about 60% to about 99.9% w/v, about 80% to about 99.9% w/v, about 90% to about 99.9% w/v, or about 95% to about 99.9% w/v. In some embodiments, the liquid carrier is aqueous. In some embodiments, the liquid carrier is non-aqueous. In some embodiments, the liquid pharmaceutical composition further comprises the liquid carrier the liquid carrier comprises polyethers, lower polyhydroxy alcohols, ethanol, propylene glycol, isosorbide dimethyl ether, di(ethylene glycol) ethyl ether, glycols, glycerin, polyethylene glycol (PEG), sugar alcohols (e.g., sorbitol), or a combination thereof. In some embodiments, the liquid carrier is present in an amount of from about 0.01% w/v to about 90% w/v, from about 1% w/v to about 80% w/v, from about 1% w/v to about 70% w/v, from about 1% w/v to about 60% w/v, from about 1% w/v to about 50% w/v, from about 1% w/v to about 40% w/v, from about 1% w/v to about 30% w/v, from about 1% w/v to about 20% w/v, from about 3% w/v to about 10% w/v, from about 3% w/v to about 7% w/v, or about 5% w/v. In some embodiments, the liquid carrier comprises propylene glycol. In some embodiments, propylene glycol is present in an amount of from about 3% w/v to about 10% w/v, from about 3% w/v to about 7% w/v, or about 5% w/v.

In any one of the foregoing or related aspects, the liquid pharmaceutical composition comprises a buffer system. In some embodiments, the buffer system comprises benzoic acid, benzoate, citric acid, citrate, acetic acid, acetate, sorbic acid, sorbate, propionic acid, propionate, carbonate, bicarbonate, glycine/glycine HCl, monobasic/dibasic phosphate, tartaric acid, tartrate, fumaric acid, ascorbic acid, ascorbate, formic acid, formate, phosphoric acid, phosphate, lactic acid, lactate, gluconates, aspartic acid, aspartate, glutamic acid, glutamate, maleic acid, maleate, succinic acid, or succinate, or a combination thereof. In some embodiments, the buffer system comprises benzoic acid, a benzoate salt (e.g., sodium benzoate), or a combination thereof. In some embodiments, the buffer system comprises benzoic acid and sodium benzoate. In some embodiments, benzoic acid and sodium benzoate are present in an amount of from 0.01% w/v to about 0.4% w/v, about 0.08% w/v to about 0.32% w/v, about 0.1% w/v to about 0.3% w/v, about 0.15% w/v to about 0.25% w/v, or about 0.16% w/v to about 0.22% w/v. In some embodiments, benzoic acid and sodium benzoate are present in an amount of from about 0.01% w/v to about 0.6% w/v, about 0.01% w/v to about 0.5% w/v, about 0.05% w/v to about 0.45% w/v, about 0.08% w/v to about 0.4% w/v, about 0.1% w/v to about 0.35% w/v, about 0.15% w/v to about 0.32% w/v, or about 0.18% w/v to about 0.32% w/v. In some embodiments, the buffer system is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.3% w/v or less, or about 0.2% w/v or less. In some embodiments, the buffer system is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.35% w/v or less, or about 0.32% w/v or less. In some embodiments, the buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D. In some embodiments, benzoic acid and sodium benzoate are present in an amount of about 0.18% w/v to about 0.22% w/v and provide a pH that is from about 4.0 to about 6.0, about 4.5 to about 5.5, or about 5.0. In some embodiments, benzoic acid is present in an amount of from about 0.005% w/v to about 0.1% w/v, about 0.01% w/v to about 0.08% w/v, about 0.015% w/v to about 0.07% w/v, about 0.015% w/v to about 0.06% w/v, about 0.02% w/v to about 0.05% w/v, about 0.03% w/v to about 0.04% w/v, or about 0.034% w/v. In some embodiments, sodium benzoate is present in an amount of from about 0.01% w/v to about 0.6% w/v, about 0.01% w/v to about 0.5% w/v, about 0.05% w/v to about 0.45% w/v, about 0.08% w/v to about 0.4% w/v, about 0.1% w/v to about 0.35% w/v, about 0.15% w/v to about 0.32% w/v, about 0.18% w/v to about 0.32% w/v, about 0.25% w/v to about 0.3% w/v, or about 0.285% w/v. In some embodiments, benzoic acid and sodium benzoate are present in an amount of from about 0.25% w/v to about 0.35% w/v, about 0.28% w/v to about 0.33% w/v, or about 0.32% w/v, and provide a pH that is from about 4.0 to about 6.0, about 4.5 to about 5.5, or about 5.0.

In any one of the foregoing or related aspects, the liquid pharmaceutical composition comprises a preservative. In some embodiments, the preservative comprises an antimicrobial agent, a chelating agent, an antioxidant, or a combination thereof. In some embodiments, the preservative comprises a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof. In some embodiments, paraben or the mixture of parabens comprises methyl paraben, ethyl paraben, or propyl paraben, or a combination thereof. In some embodiments, the mixture of parabens is present in an amount of from about 0.01% to about 0.5% w/v, from about 0.15 to about 0.25% w/v, or about 0.2% w/v. In some embodiments, the preservative comprises disodium ethylenediaminetetraacetic acid, polyphosphates, citric acid, calcium disodium edetate, ethylenediaminetetraacetic acid (EDTA), or a combination thereof. In some embodiments, EDTA is present in an amount of from about 0.01% to about 0.5% w/v, from about 0.05% to about 0.2% w/v, or about 0.1% w/v. In some embodiments, the preservative comprises an antioxidant, e.g., vitamin A, monothioglycerol, ascorbic acid, sodium bisulfite, sodium sulfite, α-Tocopherol acetate (vitamin E), butylated hydroxyanisole (BHA), butylated hydroxytoluene (BHT), propyl gallate, vitamin E, hydroquinone, hydroxycoumarins, ethanolamine, lecithin, cephalin, ascorbic acid, sorbitol, phosphoric acid, bisulfite, sodium metabisulfite, thiodipropionic acid and its esters, and dithiocarbamates or a combination thereof. In some embodiments, the antioxidant comprises BHA, BHT, or any combination thereof, and optionally. In some embodiments, the antioxidant is present in an amount of from about 0.001% to about 0.1% w/v, or about 0.01% w/v. In some embodiments, the preservative comprises benzyl alcohol, benzoic acid, sorbic acid, sodium benzoate, sodium sorbate, EDTA and its salts, parabens (such as methylparaben, ethylparaben, propylparaben, butylparaben and their salts), potassium sorbate, antibacterial agents such as halogenated diphenyl ether (e.g., triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, or any combination thereof. In some embodiments, the preservative comprises benzoic acid, or sodium benzoate, or a combination thereof. In some embodiments, the preservative is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.32% w/v or less, about 0.3% w/v or less, or about 0.2% w/v or less.

In any one of the foregoing or related aspects, the liquid pharmaceutical composition further comprises a flavoring agent. In some embodiments, the liquid pharmaceutical composition further comprises a flavoring agent and the flavoring agent comprises a natural flavoring agent, an artificial flavoring agent, or a combination thereof. In some embodiments, the flavoring agent comprises 4-hydroxy-3-methoxybenzaldehyde, methyl anthranilate, 3,5-dimethyl-1,2-cyclopentadione, maltol, 4-(4-hydroxyphenyl)butan-2-one, ethyl maltol, or ethyl propionate.

In any one of the foregoing or related aspects, the liquid pharmaceutical composition has a pH of from about 3.5 to about 6.0, about 4.0 to about 6.0, about 4.5 to about 5.5, about 4.75 to about 5.25, or about 5.0. In some embodiments, the liquid pharmaceutical composition has a pH of about 5.0.

In any one of the foregoing or related aspects, the liquid pharmaceutical composition contains no more than 5% wt of total impurities and not more than 1% wt of each of the following impurities: [Asp$^5$]desmopressin, [Glu$^4$]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at about 2° C. to about 8° C. for 3, 6, 9, 12, 18, 24, 30, or 36 months. In some embodiments, the liquid pharmaceutical composition contains no more than 5% wt of total impurities and not more than 1% wt of each of the following impurities: [Asp$^5$] desmopressin, [Glu$^4$]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at room temperature for 3 months. In some embodiments, the liquid pharmaceutical composition contains no more than 5% wt of total impurities and not more than 1% wt of each of the following impurities: [Asp5] desmopressin, [Glu4]desmopressin, [Gly$^9$OH]desmopressin, [L-Arg$^8$]desmopressin, [Gln$^4$(Acm)]desmopressin, [Asn$^5$(Acm)]desmopressin, [Gly$^9$N(CH$_3$)$_2$]desmopressin, after stored at room temperature for 6, 9, 12, 18, or 24 months. In some embodiments, the liquid pharmaceutical composition contains no more than 5% wt of total impurities and not more than 1% wt of each of the following impurities: [Asp5]desmopressin, [Glu4]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at about 40° C.±2° C. for 1 months. In some embodiments, the liquid pharmaceutical composition contains no more than 5% wt of total impurities and not more than 1% wt of each of the following impurities: [Asp5] desmopressin, [Glu4]desmopressin, [Gly$^9$OH]desmopressin, [L-Arg$^8$]desmopressin, [Gln$^4$(Acm)]desmopressin, [Asn$^5$(Acm)]desmopressin, [Gly$^9$N(CH$_3$)$_2$]desmopressin, after stored at about 40° C.±2° C. for 2, 3, or 6 months. In some embodiments, the liquid pharmaceutical composition contains no more than 3% wt of total impurities and not more than 1% wt of each of the following impurities: [Asp5]desmopressin, [Glu4]desmopressin, [Gly$^9$OH]desmopressin, [L-Arg$^8$]desmopressin, [Gln$^4$(Acm)]desmopressin, [Asn$^5$(Acm)]desmopressin, [Gly$^9$N(CH$_3$)$_2$]desmopressin, after stored at about 2° C. to about 8° C. for 3, 6, 9, 12, 18, 24, 30, or 36 months. In some embodiments, the liquid pharmaceutical composition contains no more than 3% wt of total impurities and not more than 1% wt of each of the following impurities: [Asp5]desmopressin, [Glu4]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at room temperature for 3, 6, 9, 12, 18, or 24 months. In some embodiments, the liquid pharmaceutical composition contains no more than 3% wt of total impurities and not more than 1% wt of each of the following impurities: [Asp5]desmopressin, [Glu4]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at about 40° C.±2° C. for 1, 2, 3, or 6 months. In some embodiments, the total impurities are determined according to High-performance liquid chromatography (HPLC) method. In some embodiments, the liquid pharmaceutical composition retains at least 90% wt of the initial desmopressin acetate amount after stored at about 2° C. to about 8° C. for 3, 6, 9, 12, 18, 24, 30, or 36 months. In some embodiments, the liquid pharmaceutical composition retains at least 90% wt of the initial desmopressin acetate amount after stored at room temperature for 3 months. In some embodiments, the liquid pharmaceutical composition retains at least 90% wt of the initial desmopressin acetate amount after stored at room temperature for 6, 9, 12, 18, or 24 months. In some embodiments, the liquid pharmaceutical composition retains at least 90% wt of the initial desmopressin acetate amount after stored at about 40° C.±2° C. for 1 month. In some embodiments, the liquid pharmaceutical composition retains at least 90% wt of the initial desmopressin acetate amount after stored at about 40° C.±2° C. for 2, 3, or 6 months. In some embodiments, the liquid pharmaceutical composition retains at least 95% wt of the initial desmopressin acetate amount after stored at about 2° C. to about 8° C. for 3, 6, 9, 12, 18, 24, 30, or 36 months. In some embodiments, the liquid pharmaceutical composition retains at least 95% wt of the initial desmopressin acetate amount after stored at room temperature for 3, 6, 9, 12, 18, or 24 months. In some embodiments, the liquid pharmaceutical composition retains at least 95% wt of the initial desmopressin acetate amount after stored at about 40° C.±2° C. for 1, 2, 3, or 6 months. In some embodiments, desmopressin acetate amount is determined according to HPLC method. In some embodiments, the liquid pharmaceutical composition remains stable after stored at about 2° C. to about 8° C. for at least 3, 6, 9, 12, 18, or 24 months. In some embodiments, the liquid pharmaceutical composition remains stable after stored at room temperature for at least 3, 6, 9, 12, 18, or 24 months. In some embodiments, the liquid pharmaceutical composition remains stable after stored at about 40° C.±2° C. for at least 1, 2, 3, or 6 months.

In any one of the foregoing or related aspects, the liquid pharmaceutical composition exhibits a bioavailability that is bioequivalent to a reference pharmaceutical composition that comprises desmopressin acetate, when measured as the total area under the curve (AUC) after oral administration or when measured as $C_{max}$ after oral administration. In some embodiments, the reference pharmaceutical composition is an oral tablet sold under the trade name DDAVP.

In any one of the foregoing or related aspects, the liquid pharmaceutical composition exhibits a bioavailability that is from 80% to 125% relative to a bioavailability of a reference pharmaceutical composition that comprises desmopressin acetate with a 90% confidence interval, when measured as the total area under the curve (AUC) after oral administration or when measured as Cmax after oral administration. In some embodiments, the reference pharmaceutical composition is an oral tablet sold under the trade name DDAVP.

In some aspects, disclosed herein is a direct dosing device comprising liquid pharmaceutical compositions described herein. In some embodiments, the direct dosing device is a measuring device with graduations. In some embodiments, the direct dosing device is an oral syringe.

In some aspects, disclosed herein is a method of treating a disease or condition, or symptoms thereof, comprising administering liquid pharmaceutical compositions described herein to a subject in need thereof. In some embodiments, the liquid pharmaceutical composition is administered to the subject orally or through a nasogastric, jejunostomy, or gastrostomy tube. In some embodiments, the disease or condition, or symptoms thereof is selected from diabetes insipidus, bedwetting, hemophilia A, von willebrand disease, polyurea, and high blood urea levels. In some embodiments, the disease or condition, or symptoms thereof is selected from central diabetes insipidus, primary nocturnal enuresis, nocturia, polydipsia, nocturnal polyuria, hypothalamic injury-induced obesity (HIO), bleeding in subjects with Hemophilia A and/or with von Wilebrand-Jürgens disease, and postoperative bleeding. In some embodiments, the liquid pharmaceutical composition is administered in a therapeutically effective amount. In some embodiments, the administered amount of desmopressin acetate is 90%-110%, 95%-105%, or 100% relative to a dose required for delivering a therapeutically relevant exposure of desmopressin acetate in the fasted state using a desmopressin acetate oral tablet formulation. In some embodiments, the desmopressin acetate oral tablet formulation is sold under the trade name DDAVP. In some embodiments, the administration of the liquid pharmaceutical composition to the subject is made via a direct dosing device described herein. In some embodiments, the administration of the liquid pharmaceutical composition to the subject does not involve dilution and/or addition of any further components to the liquid pharmaceutical composition.

In some aspects, disclosed herein is use of a liquid pharmaceutical compositions described herein as a medicament for the treatment of a disease or a condition.

In some aspects, disclosed herein is use of a liquid pharmaceutical compositions described herein for the manufacture of a medicament for the treatment of a disease or a condition.

In some aspects, disclosed herein is a liquid pharmaceutical compositions described herein for use in treating a disease or a condition.

In some aspects, disclosed herein is a method for administering desmopressin free base or a pharmaceutically acceptable salt thereof to a subject in need thereof, the method comprising orally administering liquid pharmaceutical compositions described herein without dilution or addition of any further components to the liquid pharmaceutical composition. In some embodiments, the administration of the liquid pharmaceutical composition to the subject is made via a direct dosing device described herein. In some embodiments, the method comprises a reduced risk of microbial contamination as compared to a method of orally administering a desmopressin composition that involves dilution and/or addition of any further components to such desmopressin composition prior to administration to the subject. In some embodiments, the method comprises an increased accuracy of dosing as compared to a method of orally administering a desmopressin composition that involves dilution and/or addition of any further components to such desmopressin composition prior to administration to the subject. In some embodiments, the subject has an age of less than 18 years old.

In some aspects, disclosed herein is a method of making liquid pharmaceutical compositions described herein. In some embodiments, the method comprises mixing desmopressin free base or a pharmaceutically acceptable salt thereof with water, thereby forming a solution of desmopressin. In some embodiments, the method comprises adding a buffer system into the solution of desmopressin. In some embodiments, the method comprises adding a two-component, dual-functional, preservative-buffer system into the solution of desmopressin. In some embodiments, the buffer system is added to water before mixing desmopressin free base or a pharmaceutically acceptable salt thereof with water. In some embodiments, the two-component, dual-functional, preservative-buffer system is added to water before mixing desmopressin free base or a pharmaceutically acceptable salt thereof with water.

In some aspects, disclosed herein is a kit comprising a package enclosing liquid pharmaceutical compositions described herein or a direct dosing device described herein. In some embodiments, the kit comprises instructions for use of the liquid pharmaceutical composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 shows the mean of the plasma concentrations of desmopressin acetate (y-axis) in all subjects tested at each time point (x-axis), after the subject received either a single oral dose of the reference product, desmopressin acetate tablet (referred to as "R") (0.2 mg×3 tablets) or a single oral dose of the test product, desmopressin oral solution (referred to as "T") 0.6 mg (12 ml×0.05 mg/ml).

DETAILED DESCRIPTION

Desmopressin is a vasopressin analogue of the natural pituitary hormone 8-arginine vasopressin (ADH). Desmopressin contains a basic arginine sidechain, and is capable of salt formation with acid species. Desmopressin's acetate salt, desmopressin acetate, is chemically defined as 1-(3-mercaptopropionic acid)-8-D-arginine vasopressin monoacetate (salt) trihydrate, and has the below structural formula:

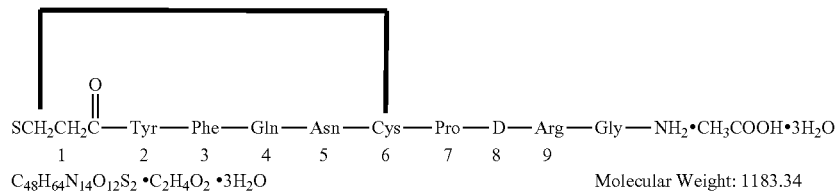

$C_{48}H_{64}N_{14}O_{12}S_2 \cdot C_2H_4O_2 \cdot 3H_2O$

Molecular Weight: 1183.34

Desmopressin Acetate

Desmopressin acetate is indicated antidiuretic replacement therapy and in the management of various medical conditions including diabetes insipidus, enuresis, hemophilia A, von willebrand disease and high blood urea levels.

The dosage of desmopressin is generally determined for each individual patient and adjusted according to their pattern of response. Desmopressin is typically administered for adults and pediatric patients at a dose of 0.05 mg two times a day, and the dose is individually adjusted to achieve the patient's optimum therapeutic dose. Because small changes in desmopressin dose can provide a large change in response, it is therefore necessary to titrate dosages in small increments. Current practice for administering liquid low doses (<0.05 mg) to patients requires first dispersing the commercial tablet in liquid media and then further diluting the suspension if necessary, before administration. This process often results in inaccurate dosing due to dilution or administration variations/errors, for example errors resulting from non-uniformity of both the particles of the crushed tablet, and their non-uniform distribution within the suspension. The inaccuracy of this process is especially problematic for low doses, e.g., <0.05 mg, where the foregoing disadvantages of diluting a suspension are enhanced. Further, the process of crushing and dispersing the tablet form provides opportunity for microbial contamination during the crushing and suspending process.

Furthermore, certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking. Many patients are unable to swallow a solid dosage form, which requires these medications to be administered in an oral liquid form. The populations unable to swallow solid dosage forms are in need of liquid formulations include pediatric patients, older patients with dysphagia, ICU patients and patients on enteral nutrition. In addition, the patient populations would benefit from a liquid formulation with a longer shelf-life that can be left at room temperature without a need to store the medication in refrigerated condition.

Currently, in the United States, the lowest solid dose that can be administered is 0.05 mg, which is obtained by splitting a 0.1 mg tablet in half. With currently marketed tablets, patients are started on doses of 0.05 mg two times a day and the dose are individually adjusted to their optimum therapeutic dose. In pediatric populations, the dose of desmopressin acetate to be given to children is calculated according to the child's weight. When the calculated dose is different than the amount present in one or more intact solid dosage forms, the solid dosage form must be divided to provide the correct dose. This leads to inaccurate dosing when solid dosages forms, such as tablets, are compounded to prepare other formulations for children. The current method of making a liquid formulation is for a compounding pharmacist to crush the desmopressin acetate tablets into powder via mortar and pestle and reconstitute the powder in some liquid form, such as an oral suspension. However, forming a desmopressin acetate oral liquid in this fashion has significant drawbacks including large variability in the actual dosage, incomplete solubilizing of the desmopressin acetate tablet in the liquid, rapid instability, inconsistent formulation methods per compounding pharmacy, and a number of other potential issues. This process is tedious and often results in inaccurate dosing due to dilution or administration variations/errors, which is disadvantageous in view of the need to titrate dosages in small increments discussed above. There also is the potential for microbial contamination during the crushing and suspending process. The crushed tablet liquid formulation may also be potentially unsafe due to contamination with residual drugs and other substances from the mortar and pestle or other crushing agents. In addition, such crushed tablet liquid formulations generally have a short in-use stability that is limited to 60 days or at most 90 days after opening even when the formulations are stored under refrigerated condition.

The Enupresol 360 and Desmirin 360 µg/mL desmopressin acetate products require significantly more dilution to achieve low dosages. Thus, they might not be able to titrate down to the lower end of the desmopressin dosage ranges, particularly for pediatric patients. Moreover, increasing the amount of dilution will ultimately lead to errors, and result in an inaccurate volume administered, which can be problematic for pediatric patients. The present disclosure, in some aspects, provides compositions that are ready-to-use and contain the desmopressin active at a relatively low concentration, and do not have these deficiencies.

These disadvantages are removed by the compositions of the present disclosure, which are solutions, and therefore do not suffer from the inaccuracies inherent in a suspension. In addition, the present compositions are used as-is, and being relatively low-concentration solutions, typically do not require dilution to achieve even low desired dosages. For example, the present compositions having a desmopressin acetate concentration of 0.05 mg/mL can accurately provide dosages of as little as 0.005 mg, for example by using a direct dosing device as described herein, e.g., an oral syringe with graduated marking for dispensing 0.1 mL of liquid. Moreover, even if dilution were required, the present compositions, being solutions, can be accurately diluted, thus affording even lower dosages.

Additionally, desmopressin acetate is chemically unstable in water, and non-tablet formulations (e.g., nasal sprays) often require refrigerated storage conditions. For example, certain nasal formulations need to be stored under refrigerated conditions. Furthermore, such nasal formulations cannot be directly used for oral administration due to many reasons, one of which include the use of certain excipients, for example, the preservatives used in such nasal formulations are not suitable for oral use.

There exists an ongoing need for more efficacious delivery of desmopressin, and in particular, a need for orally administering doses of desmopressin of less than 0.1 mg dose to patients, and particularly to pediatric patients, and also a need for stable oral liquid desmopressin formulations at such dosages that provide more accurate dosing and avoidance of potential contamination, even when stored at room temperature.

The present embodiments provide a safe and effective oral administration of desmopressin acetate for the treatment of primary nocturnal enuresis and other disorders. In particular, the embodiments provide stable desmopressin oral liquid formulations. The present embodiments also provide desmopressin oral liquid formulations as ready-to-use liquid preparations, even in pediatric populations that require a lower dose of desmopressin. Furthermore, present embodiments provide desmopressin oral liquid formulations that are stable for storage at room temperature or ambient conditions for at least 24 months, which provides significant benefits over other formulations that requires refrigerated storage conditions. In some aspect, present embodiments provide a simple formulation for desmopressin oral liquid formulations that uses a two-component, dual-functional, preservative-buffer system. Utilizing the same excipients for both buffer and preservative, while not required, can afford many benefits, such as lower manufacturing cost, reduced risk to patients posed by the use of certain excipients (e.g., attributed to lower amount of preservatives intake), convenience, and reducing the number of ionic species present in the composition which provide improved stability for the composition. The improvement in stability becomes significant for small dosages of desmopressin, where, due to the low concentration, desmopressin free base or a pharmaceutically acceptable salt thereof (e.g., desmopressin acetate), ionic species can potentially interfere with the stability of the composition.

As used herein, the term "ready-to-use" means that the composition is administered to the patient without dilution and/or the addition of any further components to the composition.

In one aspect, provided herein are desmopressin oral liquid formulations. These desmopressin oral liquid formulations described herein are useful for the treatment of diseases, conditions, or symptoms thereof, such as diabetes insipidus, bedwetting, hemophilia A, von willebrand disease, polyurea, and high blood urea levels. The formulations can be advantageous over conventional solid dosage administration of desmopressin acetate in many aspects, including ease of administration, accuracy of dosing, accessibility to additional patient populations such as to children and the elderly, and an increased patient compliance to medication.

In some aspects, the present embodiments provide desmopressin oral liquid formulations that offer the benefit of having reduced medication errors and/or increased the accuracy of dosing during administration to a patient, such as by using a direct dosing device as described herein or by not diluting and/or adding of any further components to the liquid pharmaceutical compositions.

In some embodiments, the desmopressin used in the formulations described herein is desmopressin free base or a pharmaceutically acceptable salt thereof. In some embodiments, the desmopressin used in the formulations described herein is desmopressin acetate. In some embodiments, the desmopressin used in the formulations described herein is desmopressin free base.

Desmopressin Oral Liquid Compositions

Oral liquids include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution.

In one aspect, liquid formulations described herein comprise desmopressin free base or a pharmaceutically acceptable salt thereof. In some embodiments, the liquid pharmaceutical composition comprises desmopressin free base or a pharmaceutically acceptable salt thereof in an amount of about 0.01 mg/mL to about 0.1 mg/mL. In some embodiments, the liquid pharmaceutical composition described herein is an oral solution. In some embodiments, the liquid pharmaceutical composition is stable after stored at room temperature for at least 2 months.

In some embodiments, desmopressin free base or a pharmaceutically acceptable salt thereof, is present in oral liquid formulations described herein in an amount of about 0.01 mg/mL to about 0.08 mg/mL, about 0.03 mg/mL to about 0.07 mg/mL, or about 0.04 mg/mL to about 0.06 mg/mL. In some embodiments, desmopressin free base or a pharmaceutically acceptable salt thereof, is present in the oral liquid formulation in an amount of about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, or about 0.1 mg/mL. In some embodiments, desmopressin free base or a pharmaceutically acceptable salt thereof, is present in the oral liquid formulation in an amount of about 0.01 mg/mL. In some embodiments, desmopressin free base or a pharmaceutically acceptable salt thereof, is present in the oral liquid formulation in an amount of about 0.05 mg/mL. In some embodiments, desmopressin free base or a pharmaceutically acceptable salt thereof is present in an amount of about 0.02 mg/mL. In some embodiments, desmopressin free base or a pharmaceutically acceptable salt thereof is present in an amount of about 0.025 mg/mL. In some embodiments, desmopressin free base or a pharmaceutically acceptable salt thereof is present in an amount of about 0.03 mg/mL. In some embodiments, desmopressin free base or a pharmaceutically acceptable salt thereof is present in an amount of about 0.04 mg/mL. In some embodiments, desmopressin free base or a pharmaceutically acceptable salt thereof is present in an amount of about 0.05 mg/mL. In some embodiments, desmopressin free base or a pharmaceutically acceptable salt thereof is present in an amount of about 0.1 mg/mL. In some embodiments, pharmaceutically acceptable salt of desmopressin is desmopressin acetate. In some embodiments, desmopressin acetate is present in an amount of about 0.01 mg/mL to about 0.08 mg/mL, about 0.03 mg/mL to about 0.07 mg/mL, or about 0.04 mg/mL to about 0.06 mg/mL. In some embodiments, desmopressin acetate is present in the oral liquid formulation in an amount of about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, or about 0.1 mg/mL. In some embodiments, desmopressin acetate is present in an amount of about 0.01 mg/mL to about 0.08 mg/mL. In some embodiments, desmopressin acetate is present in an amount of about 0.03 mg/mL to about 0.07 mg/mL. In some embodiments, desmopressin acetate is present in an amount of about 0.04 mg/mL to about 0.06 mg/mL. In some embodiments, desmopressin acetate is present in an amount of about 0.01 mg/mL. In some embodiments, desmopressin acetate is present in an amount of about 0.02 mg/mL. In some embodiments, desmopressin acetate is present in an amount of about 0.025 mg/mL. In some embodiments, desmopressin acetate is present in an amount of about 0.03 mg/mL. In some embodiments, desmopressin acetate is present in an amount of about 0.4 mg/mL. In some embodiments, desmopressin acetate is present in an amount of about 0.05 mg/mL. In some embodiments, desmopressin acetate is present in an amount of about 0.1 mg/mL.

In other embodiments, liquid formulations described herein are suitable for desmopressin free base or a pharmaceutically acceptable salt thereof at a higher strength than described above. For example, desmopressin free base or a pharmaceutically acceptable salt thereof is present in about 0.1 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, about 0.5 mg/mL, about 0.55 mg/mL, about 0.6 mg/mL, about 0.65 mg/mL, about 0.7 mg/mL, about 0.75 mg/mL, about 0.8 mg/mL, about 0.85 mg/mL, about 0.9 mg/mL, about 0.95 mg/mL, about 1 mg/mL, about 2 mg/mL, about 3 mg/mL, about 4 mg/mL, or about 5 mg/mL in the liquid oral formulation. In some embodiments, desmopressin free base or a pharmaceutically acceptable salt thereof is present in about 0.2 mg/ml in the oral liquid formulation. In some embodiments, desmopressin free base or a pharmaceutically acceptable salt thereof is present in about 0.5 mg/ml in the oral liquid formulation. some embodiments, desmopressin free base or a pharmaceutically acceptable salt thereof is present in about 1 mg/ml in the oral liquid formulation. In some embodiments, desmopressin free base or a pharmaceutically acceptable salt thereof is present in the oral liquid formulation in an amount of about 1 to about 5 mg/ml. In some embodiments, desmopressin free base a pharmaceutically acceptable salt thereof is present in about 2 mg/ml in the oral liquid formulation. In some embodiments, desmopressin free base a pharmaceutically acceptable salt thereof is present in about 5 mg/ml in the oral liquid formulation.

In some embodiments, desmopressin free base or a pharmaceutically acceptable salt thereof, is present in the liquid pharmaceutical composition in an amount of about 0.001% weight by volume (w/v) to about 1% w/v. In other embodiments, desmopressin free base or a pharmaceutically acceptable salt thereof, is present in the liquid pharmaceutical composition in an amount of about 0.001% w/v to about 0.005% w/v, about 0.002% w/v to about 0.008% w/v, about 0.003% w/v to about 0.007% w/v, about 0.004% w/v to about 0.006% w/v, about 0.005% w/v to about 0.01% w/v, about 0.01% w/v to about 0.05% w/v, about 0.05% w/v to about 0.1% w/v, about 0.1% w/v to about 0.2% w/v, about 0.2% w/v to about 0.5% w/v, or about 0.5% w/v to about 1% w/v. In some embodiments, desmopressin free base or a pharmaceutically acceptable salt thereof is present in the liquid pharmaceutical composition in an amount of about 0.001% w/v. In some embodiments, desmopressin free base or a pharmaceutically acceptable salt thereof is present in the liquid pharmaceutical composition in an amount of about 0.005% w/v. In some embodiments, desmopressin free base or a pharmaceutically acceptable salt thereof is present in the liquid pharmaceutical composition in an amount of about 0.01% w/v. In some embodiments, desmopressin free base or a pharmaceutically acceptable salt thereof is present in the liquid pharmaceutical composition in an amount of about 0.02% w/v. In some embodiments, desmopressin free base or a pharmaceutically acceptable salt thereof is present in the liquid pharmaceutical composition in an amount of about 0.05% w/v.

In some aspects, provided herein is a liquid pharmaceutical composition comprising desmopressin free base or a pharmaceutically acceptable salt thereof and a two-component, dual-functional, preservative-buffer system.

In some aspects, provided herein is a liquid pharmaceutical composition comprising desmopressin free base or a pharmaceutically acceptable salt thereof and a buffer system. In some embodiments, the buffer system is present in an amount of about 0.32% w/v or less. In some embodiments, the buffer system also functions as a preservative. In some embodiments, the buffer system comprises two components. In some embodiments, the buffer system comprises three or more components.

In some aspects, provided herein is a liquid pharmaceutical composition, comprising desmopressin acetate and water. In some embodiments, the liquid pharmaceutical composition comprises sodium benzoate. In some embodiments, the liquid pharmaceutical composition comprises benzoic acid. In some embodiments, the liquid pharmaceutical composition is an oral solution. In some embodiments, the liquid pharmaceutical composition comprises desmopressin acetate in an amount of about 0.01 to about 0.5 mg/mL. In some embodiments, the liquid pharmaceutical composition comprises desmopressin acetate in an amount of about 0.01 to about 0.1 mg/mL. In some embodiments, the liquid pharmaceutical composition comprises desmopressin acetate in an amount of about 0.01 to about 0.05 mg/mL. In some embodiments, the liquid pharmaceutical composition comprises desmopressin acetate in an amount of about 0.05 mg/mL. In some embodiments, the liquid pharmaceutical composition comprises sodium benzoate in an amount of about 0.05% w/v to about 0.3% w/v. In some embodiments, the liquid pharmaceutical composition comprises sodium benzoate in an amount of about 0.2% w/v to about 0.3% w/v. In some embodiments, the liquid pharmaceutical composition comprises sodium benzoate in an amount of about 0.25% w/v to about 0.3% w/v. In some embodiments, the liquid pharmaceutical composition comprises sodium benzoate in an amount of about 0.285% w/v. In some embodiments, the liquid pharmaceutical composition comprises sodium benzoate in an amount of about 0.08% w/v to about 0.25% w/v. In some embodiments, the liquid pharmaceutical composition comprises sodium benzoate in an amount of about 0.1% w/v to about 0.22% w/v. In some embodiments, the liquid pharmaceutical composition comprises sodium benzoate in an amount of about 0.15% w/v to about 0.22% w/v. In some embodiments, the liquid pharmaceutical composition comprises sodium benzoate in an amount of about 0.16% w/v to about 0.2% w/v. In some embodiments, the liquid pharmaceutical composition comprises sodium benzoate in an amount of about 0.19% w/v. In some embodiments, the liquid pharmaceutical composition comprises sodium benzoate in an amount of about 0.17% w/v. In some embodiments, the liquid pharmaceutical composition comprises sodium benzoate in an amount of about 0.18% w/v. In some embodiments, the liquid pharmaceutical composition comprises sodium benzoate in an amount of about 0.19% w/v. In some embodiments, the liquid pharmaceutical composition comprises benzoic acid in an amount of about 0.005% w/v to about 0.05% w/v. In some embodiments, the liquid pharmaceutical composition comprises benzoic acid in an amount of about 0.01% w/v to about 0.05% w/v. In some embodiments, the liquid pharmaceutical composition comprises benzoic acid in an amount of about 0.01% w/v to about 0.04% w/v. In some embodiments, the liquid pharmaceutical composition comprises benzoic acid in an amount of about 0.02% w/v to about 0.04% w/v. In some embodiments, the liquid pharmaceutical composition comprises benzoic acid in an amount of about 0.03% w/v to about 0.04% w/v. In some embodiments, the liquid pharmaceutical composition comprises benzoic acid in an amount of about 0.034% w/v. In some embodiments, the liquid pharmaceutical composition comprises benzoic acid in an amount of about 0.01% w/v to about 0.03% w/v. In some embodiments, the liquid pharmaceutical composition comprises benzoic acid in an amount of about 0.015% w/v to about 0.025% w/v. In some embodiments, the liquid pharmaceutical composition comprises benzoic acid in an amount of about 0.02% w/v. In some embodiments, the liquid pharmaceutical composition comprises a) desmopressin acetate in an amount of about 0.01 to about 0.1 mg/mL; b) sodium benzoate in an amount of about 0.18% w/v to about 0.4% w/v; c) benzoic acid in an amount of about 0.03% w/v to about 0.04% w/v; and d) water. In some embodiments, the liquid pharmaceutical composition comprises a) desmopressin acetate in an amount of about 0.025 to about 0.075 mg/mL; b) sodium benzoate in an amount of about 0.2% w/v to about 0.35% w/v; c) benzoic acid in an amount of about 0.03% w/v to about 0.04% w/v; and d) water. In some embodiments, the liquid pharmaceutical composition comprises a) desmopressin acetate in an amount of about 0.05 mg/mL; b) sodium benzoate in an amount of about 0.25% w/v to about 0.3% w/v; c) benzoic acid in an amount of about 0.03% w/v to about 0.035% w/v; and d) water. In some embodiments, the liquid pharmaceutical composition comprises a) desmopressin acetate in an amount of about 0.05 mg/mL; b) sodium benzoate in an amount of about 0.25% w/v to about 0.3% w/v; c) benzoic acid in an amount of about 0.034% w/v; and d) water. In some embodiments, the liquid pharmaceutical composition comprises a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition consists essentially of a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition consists of a) desmopressin acetate in an amount of about 0.05 mg/mL; b) sodium benzoate in an amount of about 0.285% w/v; c) benzoic acid in an amount of about 0.034% w/v; and d) water. In some embodiments, the liquid pharmaceutical composition comprises a) desmopressin acetate in an amount of about 0.01 to about 0.05 mg/mL; b) sodium benzoate in an amount of about 0.08% w/v to about 0.25% w/v; c) benzoic acid in an amount of about 0.01% w/v to about 0.03% w/v; and d) water. In some embodiments, the liquid pharmaceutical composition comprises a) desmopressin acetate in an amount of about 0.05 mg/mL; b) sodium benzoate in an amount of about 0.16% w/v to about 0.2% w/v; c) benzoic acid in an amount of about 0.02% w/v; and d) water. In some embodiments, the liquid pharmaceutical composition consists essentially of a) desmopressin acetate in an amount of about 0.05 mg/mL; b) sodium benzoate in an amount of about 0.16% w/v to about 0.2% w/v; c) benzoic acid in an amount of about 0.02% w/v; and d) water. In some embodiments, the liquid pharmaceutical composition consists of a) desmopressin acetate in an amount of about 0.05 mg/mL; b) sodium benzoate in an amount of about 0.16% w/v to about 0.2% w/v; c) benzoic acid in an amount of about 0.02% w/v; and d) water.

In some aspects, provided herein is a liquid pharmaceutical composition that is ready-to-use. In some embodiments, the liquid pharmaceutical composition is ready-to-use in pediatric population. In some embodiments, the liquid pharmaceutical composition is ready-to-use without dilution in pediatric population. In some embodiments, the liquid pharmaceutical composition is ready-to-use without addition of any further components for administration in pediatric population. In some embodiments, the liquid pharmaceutical composition is ready-to-use without dilution and/or addition of any further components for administration in pediatric population. In some embodiments, a liquid pharmaceutical composition described herein does not comprise malic acid or malate. In some embodiments, a liquid pharmaceutical composition described herein does not comprise a sweetener.

In some embodiments, a liquid pharmaceutical composition described herein comprises desmopressin free base. In some embodiments, a liquid pharmaceutical composition described herein comprises a pharmaceutically acceptable salt of desmopressin. In some embodiments, a pharmaceutically acceptable salt of desmopressin is desmopressin acetate. Pharmaceutically acceptable salts of desmopressin can include acid addition salts with organic and inorganic acids, for example, hydrochloric (i.e., hydrochloride), sulfuric (i.e., sulfate and bisulfate), phosphoric (i.e., mono- or dibasic phosphate), carbonic (i.e., carbonate or bicarbonate), carboxylic acids e.g., acetic acid and trifluoroacetic acid (i.e., acetate and trifluoroacetate), citric acid (i.e., citrate), tartaric acid (i.e., tartrate), malic acid (i.e., malate); maleic acid (i.e., maleate); fumaric acid (i.e., fumarate); ascorbic acid (i.e., ascorbate); lactic acid (i.e., lactate); glutamic acid (i.e., glutamate) and succinic acid (i.e., succinate). In some embodiments, a liquid pharmaceutical composition described herein comprises desmopressin acetate.

In some embodiments, liquid pharmaceutical compositions described herein has a pH of from about 3.5 to about 6.0, about 4.0 to about 6.0, about 4.5 to about 5.5, about 4.75 to about 5.25, or about 5.0. In some embodiments, liquid pharmaceutical compositions described herein has a pH of from about 3.5 to about 6.0. In some embodiments, liquid pharmaceutical compositions described herein has a pH of from about 4.0 to about 6.0. In some embodiments, liquid pharmaceutical compositions described herein has a pH of from about 4.5 to about 5.5. In some embodiments, liquid pharmaceutical compositions described herein has a pH of from about 4.75 to about 5.25. In some embodiments, liquid pharmaceutical compositions described herein has a pH of from about 5.0. In some embodiments, the pH of the liquid pharmaceutical composition is adjusted with an acid or base to achieve a pH of from about 3.5 to about 6.0. In some embodiments, the pH of the liquid pharmaceutical composition is adjusted with an acid or base to achieve a pH of from about 4.5 to about 5.5. In some embodiments, the pH of the liquid pharmaceutical composition is adjusted with an acid or base to achieve a pH of about 5.0. The pH adjustment can be made with a strong acid (e.g., hydrochloric acid, sulfuric acid, phosphoric acid, nitric acid, etc.) or a strong base (sodium hydroxide, potassium hydroxide, etc.), or any suitable acids and/or bases described herein, during the preparation of the liquid pharmaceutical composition. In some embodiments, buffer systems described herein (e.g., a buffer system, a buffer system that also functions as a preservative, or a two-component, dual-functional, preservative-buffer system) and any desmopressin acid addition salts within a liquid pharmaceutical composition described herein maintains the pH of the liquid pharmaceutical composition during storage (e.g., maintains the pH of from about 4.5 to about 5.5).

In some embodiments, a liquid pharmaceutical composition described herein comprises water. In some embodiments, water is present in the liquid pharmaceutical composition in an amount of about 10% to about 99.9% w/v, about 20% to about 99.9% w/v, about 30% to about 99.9% w/v, about 40% to about 99.9% w/v, about 50% to about 99.9% w/v, about 60% to about 99.9% w/v, or about 70% to about 99.9% w/v. In some embodiments, water is present in the liquid pharmaceutical composition in an amount of about 10% to about 99.9% w/v. In some embodiments, water is present in the liquid pharmaceutical composition in an amount of about 20% to about 99.9% w/v. In some embodiments, water is present in the liquid pharmaceutical composition in an amount of about 30% to about 99.9% w/v. In some embodiments, water is present in the liquid pharmaceutical composition in an amount of about 40% to about 99.9% w/v. In some embodiments, water is present in the liquid pharmaceutical composition in an amount of about 50% to about 99.9% w/v. In some embodiments, water is present in the liquid pharmaceutical composition in an amount of about 60% to about 99.9% w/v. In some embodiments, water is present in the liquid pharmaceutical composition in an amount of about 70% to about 99.9% w/v. In some embodiments, water is present in the liquid pharmaceutical composition in an amount of about 10% w/v to about 15% w/v, about 15% w/v to about 20% w/v, about 20% w/v to about 30% w/v, about 30% w/v to about 40% w/v, about 40% w/v to about 50% w/v, about 50% w/v to about 60% w/v, about 60% w/v to about 70% w/v, about 70% w/v to about 80% w/v, about 80% w/v to about 90% w/v, about 90% w/v to about 95% w/v, about 95% w/v to about 98% w/v, about 98% w/v to about 99% w/v, or about 99% w/v to about 99.9% w/v. In some embodiments, water is present in the liquid pharmaceutical composition in an amount of about 80% to about 99.9% w/v, about 90% to about 99.9% w/v, or about 95% to about 99.9% w/v. In some embodiments, water is present in the liquid pharmaceutical composition in an amount of about 95% to about 99.9% w/v. In some embodiments, water is present in the liquid pharmaceutical composition in an amount of about 80% to about 99.9% w/v. In some embodiments, water is present in the liquid pharmaceutical composition in an amount of about 90% to about 99.9% w/v. In some embodiments, water is present in the liquid pharmaceutical composition in an amount of about 95% w/v. In some embodiments, water is present in the liquid pharmaceutical composition in an amount of about 99% w/v. In some embodiments, water is present in the liquid pharmaceutical composition in an amount of about 99.8% w/v.

In some embodiments, a liquid pharmaceutical composition described herein exhibits a bioavailability that is bioequivalent to a reference pharmaceutical composition that comprises desmopressin acetate. In some embodiments, the bioavailability is measured as the total area under the curve (AUC) after oral administration In some embodiments, the bioavailability is measured as $C_{max}$ after oral administration. In some embodiments, the reference pharmaceutical composition is an oral tablet sold under the trade name DDAVP. In some embodiments, the liquid pharmaceutical composition exhibits a bioavailability that is from 90% to 105% relative to a reference pharmaceutical composition that comprises desmopressin acetate when measured as AUC after oral administration. In some embodiments, the liquid pharmaceutical composition exhibits a bioavailability that is from 93% to 100% relative to a reference pharmaceutical composition that comprises desmopressin acetate when measured as AUC after oral administration. In some embodiments, the liquid pharmaceutical composition exhibits a bioavailability that is from 94% to 96% relative to a reference pharmaceutical composition that comprises desmopressin acetate when measured as AUC after oral administration. In some embodiments, the liquid pharmaceutical composition exhibits a bioavailability that is 95% relative to a reference pharmaceutical composition that comprises desmopressin acetate when measured as AUC after oral administration. In some embodiments, the liquid pharmaceutical composition exhibits a bioavailability that is from 95% to 105% relative to a reference pharmaceutical composition that comprises desmopressin acetate when measured as $C_{max}$ after oral administration. In some embodiments, the liquid pharmaceutical composition exhibits a bioavailability that is from 98% to 103% relative to a reference pharmaceutical composition that comprises desmopressin acetate when measured as $C_{max}$ after oral administration. In some embodiments, the liquid pharmaceutical composition exhibits a bioavailability that is from 100% to 102% relative to a reference pharmaceutical composition that comprises desmopressin acetate when measured as $C_{max}$ after oral administration. In some embodiments, the liquid pharmaceutical composition exhibits a bioavailability that is 100.5% relative to a reference pharmaceutical composition that comprises desmopressin acetate when measured as $C_{max}$ after oral administration. The term "bioequivalent" as used herein when referring to two pharmaceutical compositions means the two pharmaceutical compositions are considered equal in rate or extent to which the active pharmaceutical ingredient becomes available at the site of drug action according to the standards set forth by the US. Food and Drug Administration.

In some embodiments, a liquid pharmaceutical composition described herein exhibits a bioavailability that is from 80% to 125% relative to a bioavailability of a reference pharmaceutical composition that comprises desmopressin acetate with a 90% confidence interval. In some embodiments, the bioavailability is measured as the total area under the curve (AUC) after oral administration. In some embodiments, the bioavailability is measured as Cmax after oral administration. In some embodiments, the reference pharmaceutical composition is an oral tablet. In some embodiments, the reference pharmaceutical composition is an oral tablet sold under the trade name DDAVP. In some embodiments, the liquid pharmaceutical composition exhibits a bioavailability that is from 80% to 125% relative to a bioavailability of a reference pharmaceutical composition that comprises desmopressin acetate with a 90% confidence interval when measured as AUC after oral administration. In some embodiments, the liquid pharmaceutical composition exhibits a bioavailability that is from 80% to 120% relative to a bioavailability of a reference pharmaceutical composition that comprises desmopressin acetate with a 90% confidence interval when measured as AUC after oral administration. In some embodiments, the liquid pharmaceutical composition exhibits a bioavailability that is from 80% to 115% relative to a bioavailability of a reference pharmaceutical composition that comprises desmopressin acetate with a 90% confidence interval when measured as AUC after oral administration. In some embodiments, the liquid pharmaceutical composition exhibits a bioavailability that is from 83% to 110% relative to a bioavailability of a reference pharmaceutical composition that comprises desmopressin acetate with a 90% confidence interval when measured as AUC after oral administration. In some embodiments, the liquid pharmaceutical composition exhibits a bioavailability that is from 84% to 108% relative to a bioavailability of a reference pharmaceutical composition that comprises desmopressin acetate with a 90% confidence interval when measured as AUC after oral administration. In some embodiments, the liquid pharmaceutical composition exhibits a bioavailability that is from 80% to 125% relative to a bioavailability of a reference pharmaceutical composition that comprises desmopressin acetate with a 90% confidence interval when measured as Cmax after oral administration. In some embodiments, the liquid pharmaceutical composition exhibits a bioavailability that is from 80% to 120% relative to a bioavailability of a reference pharmaceutical composition that comprises desmopressin acetate with a 90% confidence interval when measured as Cmax after oral administration. In some embodiments, the liquid pharmaceutical composition exhibits a bioavailability that is from 85% to 120% relative to a bioavailability of a reference pharmaceutical composition that comprises desmopressin acetate with a 90% confidence interval when measured as Cmax after oral administration. In some embodiments, the liquid pharmaceutical composition exhibits a bioavailability that is from 85% to 118% relative to a bioavailability of a reference pharmaceutical composition that comprises desmopressin acetate with a 90% confidence interval when measured as Cmax after oral administration. In some embodiments, the liquid pharmaceutical composition exhibits a bioavailability that is from 87% to 115% relative to a bioavailability of a reference pharmaceutical composition that comprises desmopressin acetate with a 90% confidence interval when measured as Cmax after oral administration.

Stability

In some embodiments, desmopressin oral liquid formulations described herein are stable or shelf-stable in various storage conditions including refrigerated conditions, ambient conditions, room temperature, and accelerated conditions. Stable or shelf stable as used herein refer to desmopressin oral liquid formulations having about 90% wt or greater of initial desmopressin (e.g., desmopressin acetate) amount and about 5% wt or less total impurities or related substances and not more than 1% wt of each of the following impurities: [Asp$^5$]desmopressin, [Glu$^4$]desmopressin, [Gly$^9$OH]desmopressin, [L-Arg$^8$]desmopressin, [Gln$^4$(Acm)]desmopressin, [Asn$^5$(Acm)]desmopressin, [Gly$^9$N(CH$_3$)$_2$]desmopressin (collectively "peptide related impurities" as used hereinafter) at the end of a given storage period. Alternatively, stable or shelf stable as used herein refer to desmopressin oral liquid formulations having about 95% or greater of the initial desmopressin (e.g., desmopressin acetate) amount and about 3% wt or less total impurities or related substances and not more than 1% wt of each of the peptide related impurities: at the end of a given storage period. In some embodiments, the desmopressin oral liquid formulations are stored in an unopened container, such as an unopened bottle.

The percentage of impurities can be calculated from the amount of impurities relative to the amount of desmopressin acetate. The percentage of impurities can be assessed by any suitable HPLC methods or any other known testing method. In some embodiments, a stable desmopressin oral liquid composition contains no more than about 10% wt, about 5% wt, about 4% wt, about 3% wt, about 2.5% wt, about 2% wt, about 1.5% wt, about 1% wt, or about 0.5% wt total impurities or related substances. In other embodiments, a stable desmopressin oral liquid composition contains no more than about 10% wt total impurities or related substances. In other embodiments, a stable desmopressin oral liquid composition contains no more than about 5% wt total impurities or related substances. In yet other embodiments, a stable desmopressin oral liquid composition contains no more than about 4% wt total impurities or related substances. In yet other embodiments, a stable desmopressin oral liquid composition contains no more than about 3% wt total impurities or related substances. In yet other embodiments, a stable desmopressin oral liquid composition contains no more than about 2% wt total impurities or related substances. In yet other embodiments, a stable desmopressin oral liquid composition contains no more than about 1% wt total impurities or related substances. In some embodiments, a stable desmopressin oral liquid composition contains not more than 1% wt of each of the peptide related impurities. In some embodiments, a stable desmopressin oral liquid composition contains not more than 1.0%, 0.9%, 0.8%, 0.7%, 0.6%, 0.5% wt of each of the peptide related impurities.

The percentage of desmopressin free base or a pharmaceutically acceptable salt thereof (e.g., desmopressin acetate) retained can be calculated from the amount of desmopressin acetate in the composition at a certain time point relative to the initial amount of desmopressin acetate. Assay or desmopressin acetate content can be assessed by any suitable HPLC methods or any other known testing method. In some embodiments, a stable desmopressin oral liquid composition retains at least about 90% wt, about 91% wt, about 92% wt, about 93% wt, about 94% wt, about 95% wt, about 96% wt, about 97% wt, about 98% wt, about 99% wt, about 99.5% wt, or about 99.9% wt of the initial desmopressin amount (e.g., desmopressin acetate). In yet other embodiments, a stable desmopressin oral liquid composition retains at least about 90% wt of the initial desmopressin acetate amount. In yet other embodiments, a stable desmopressin oral liquid composition retains at least about 91% wt of the initial desmopressin acetate amount. In yet other embodiments, a stable desmopressin oral liquid composition retains at least about 92% wt of the initial desmopressin acetate amount. In yet other embodiments, a stable desmopressin oral liquid composition retains at least about 93% wt of the initial desmopressin acetate amount. In yet other embodiments, a stable desmopressin oral liquid composition retains at least about 94% wt of the initial desmopressin acetate amount. In yet other embodiments, a stable desmopressin oral liquid composition retains at least about 95% wt of the initial desmopressin acetate amount. In yet other embodiments, a stable desmopressin oral liquid composition retains at least about % % wt of the initial desmopressin acetate amount. In yet other embodiments, a stable desmopressin oral liquid composition retains at least about 97% wt of the initial desmopressin acetate amount. In yet other embodiments, a stable desmopressin oral liquid composition retains at least about 98% wt of the initial desmopressin acetate amount. In yet other embodiments, a stable desmopressin oral liquid composition retains at least about 99% wt of the initial desmopressin acetate amount. In yet other embodiments, a stable desmopressin oral liquid composition retains at least about 99.5% wt of the initial desmopressin acetate amount. In yet other embodiments, a stable desmopressin oral liquid composition retains at least about 99.8% wt of the initial desmopressin acetate amount.

In some embodiments, desmopressin oral liquid formulations described herein are stable when stored at refrigerated conditions for at least 1 month, at least 2 months, at least 3 months, at least 6 months, at least 9 months, at least 12 months, at least 15 months, at least 18 months, at least 24 months, at least 30 months, or at least 36 months. In some embodiments, the desmopressin oral liquid formulations described herein are stable when stored at about 2° C. to about 8° C. for at least 1 month, at least 2 months, at least 3 months, at least 6 months, at least 9 months, at least 12 months, at least 15 months, at least 18 months, at least 24 months, at least 30 months, or at least 36 months.

In some embodiments, a desmopressin oral liquid composition described herein contains no more than 5% wt of total impurities and not more than 1% wt of each of the peptide related impurities after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the desmopressin oral liquid composition contains no more than 5% wt of total impurities and not more than 1% wt of each of the peptide related impurities after stored at about 2° C. to about 8° C. for 3 months. In some embodiments, the desmopressin oral liquid composition contains no more than 5% wt of total impurities and not more than 1% wt of each of the peptide related impurities after stored at about 2° C. to about 8° C. for 6 months. In some embodiments, the desmopressin oral liquid composition contains no more than 5% wt of total impurities and not more than 1% wt of each of the peptide related impurities after stored at about 2° C. to about 8° C. for 9 months. In some embodiments, the desmopressin oral liquid composition contains no more than 5% wt of total impurities and not more than 1% wt of each of the peptide related impurities after stored at about 2° C. to about 8° C. for 12 months. In some embodiments, the desmopressin oral liquid composition contains no more than 5% wt of total impurities and not more than 1% wt of each of the peptide related impurities after stored at about 2° C. to about 8° C. for 15 months. In some embodiments, the desmopressin oral liquid composition contains no more than 5% wt of total impurities and not more than 1% wt of each of the peptide related impurities after stored at about 2° C. to about 8° C. for 18 months. In some embodiments, the desmopressin oral liquid composition contains no more than 5% wt of total impurities and not more than 1% wt of each of the peptide related impurities after stored at about 2° C. to about 8° C. for 24 months. In some embodiments, the desmopressin oral liquid composition contains no more than 5% wt of total impurities and not more than 1% wt of each of the peptide related impurities after stored at about 2° C. to about 8° C. for 30 months. In some embodiments, the desmopressin oral liquid composition contains no more than 5% wt of total impurities and not more than 1% wt of each of the peptide related impurities after stored at about 2° C. to about 8° C. for 36 months.

In some embodiments, a desmopressin oral liquid composition contains no more than 3% wt of total impurities and not more than 1% wt of each of the peptide related impurities after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the desmopressin oral liquid composition contains no more than 3% wt of total impurities and not more than 1% wt of each of the peptide related impurities after stored at about 2° C. to about 8° C. for 3 months. In some embodiments, the desmopressin oral liquid composition contains no more than 3% wt of total impurities and not more than 1% wt of each of the peptide related impurities after stored at about 2° C. to about 8° C. for 6 months. In some embodiments, the desmopressin oral liquid composition contains no more than 3% wt of total impurities and not more than 1% wt of each of the peptide related impurities after stored at about 2° C. to about 8° C. for 9 months. In some embodiments, the desmopressin oral liquid composition contains no more than 3% wt of total impurities and not more than 1% wt of each of the peptide related impurities after stored at about 2° C. to about 8° C. for 12 months. In some embodiments, the desmopressin oral liquid composition contains no more than 3% wt of total impurities and not more than 1% wt of each of the peptide related impurities after stored at about 2° C. to about 8° C. for 15 months. In some embodiments, the desmopressin oral liquid composition contains no more than 3% wt of total impurities and not more than 1% wt of each of the peptide related impurities after stored at about 2° C. to about 8° C. for 18 months. In some embodiments, the desmopressin oral liquid composition contains no more than 3% wt of total impurities and not more than 1% wt of each of the peptide related impurities after stored at about 2° C. to about 8° C. for 24 months. In some embodiments, the desmopressin oral liquid composition contains no more than 3% wt of total impurities and not more than 1% wt of each of the peptide related impurities after stored at about 2° C. to about 8° C. for 30 months. In some embodiments, the desmopressin oral liquid composition contains no more than 3% wt of total impurities and not more than 1% wt of each of the peptide related impurities after stored at about 2° C. to about 8° C. for 36 months.

In some embodiments, a desmopressin oral liquid composition described herein retains at least 90% wt of the initial desmopressin acetate amount after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the desmopressin oral liquid composition retains at least 90% wt of the initial desmopressin acetate amount after stored at about 2° C. to about 8° C. for 3 months. In some embodiments, the desmopressin oral liquid composition retains at least 90% wt of the initial desmopressin acetate amount after stored at about 2° C. to about 8° C. for 6 months. In some embodiments, the desmopressin oral liquid composition retains at least 90% wt of the initial desmopressin acetate amount after stored at about 2° C. to about 8° C. for 9 months. In some embodiments, the desmopressin oral liquid composition retains at least 90% wt of the initial desmopressin acetate amount after stored at about 2° C. to about 8° C. for 12 months. In some embodiments, the desmopressin oral liquid composition retains at least 90% wt of the initial desmopressin acetate amount after stored at about 2° C. to about 8° C. for 15 months. In some embodiments, the desmopressin oral liquid composition retains at least 90% wt of the initial desmopressin acetate amount after stored at about 2° C. to about 8° C. for 18 months. In some embodiments, the desmopressin oral liquid composition retains at least 90% wt of the initial desmopressin acetate amount after stored at about 2° C. to about 8° C. for 24 months. In some embodiments, the desmopressin oral liquid composition retains at least 90% wt of the initial desmopressin acetate amount after stored at about 2° C. to about 8° C. for 30 months. In some embodiments, the desmopressin oral liquid composition retains at least 90% wt of the initial desmopressin acetate amount after stored at about 2° C. to about 8° C. for 36 months.

In some embodiments, a desmopressin oral liquid composition described herein at least 95% wt of the initial desmopressin acetate amount after stored at about 2° C. to about 8° C. for at least 3 months, at least 6 months, at least 9 months, at least 12 months, at least 15 months, at least 18 months, at least 24 months, at least 30 months, or at least 36 months. In some embodiments, the desmopressin oral liquid composition retains at least 95% wt of the initial desmopressin acetate amount after stored at about 2° C. to about 8° C. for 3 months. In some embodiments, the desmopressin oral liquid composition retains at least 95% wt of the initial desmopressin acetate amount after stored at about 2° C. to about 8° C. for 6 months. In some embodiments, the desmopressin oral liquid composition retains at least 95% wt of the initial desmopressin acetate amount after stored at about 2° C. to about 8° C. for 9 months. In some embodiments, the desmopressin oral liquid composition retains at least 95% wt of the initial desmopressin acetate amount after stored at about 2° C. to about 8° C. for 12 months. In some embodiments, the desmopressin oral liquid composition retains at least 95% wt of the initial desmopressin acetate amount after stored at about 2° C. to about 8° C. for 15 months. In some embodiments, the desmopressin oral liquid composition retains at least 95% wt of the initial desmopressin acetate amount after stored at about 2° C. to about 8° C. for 18 months. In some embodiments, the desmopressin oral liquid composition retains at least 95% wt of the initial desmopressin acetate amount after stored at about 2° C. to about 8° C. for 24 months. In some embodiments, the desmopressin oral liquid composition retains at least 95% wt of the initial desmopressin acetate amount after stored at about 2° C. to about 8° C. for 30 months. In some embodiments, the desmopressin oral liquid composition retains at least 95% wt of the initial desmopressin acetate amount after stored at about 2° C. to about 8° C. for 36 months.

In some embodiments, a desmopressin oral liquid composition described herein contains no more than 5% wt of total impurities and not more than 1% wt of each of the peptide related impurities after stored at refrigerated conditions for at least 3 months, at least 6 months, at least 9 months, at least 12 months, at least 15 months, at least 18 months, at least 24 months, at least 30 months, or at least 36 months. In some embodiments, the desmopressin oral liquid composition contains no more than 5% wt of total impurities and not more than 1% wt of each of the peptide related impurities after stored at refrigerated conditions for 3 months. In some embodiments, the desmopressin oral liquid composition contains no more than 5% wt of total impurities and not more than 1% wt of each of the peptide related impurities after stored at refrigerated conditions for 6 months. In some embodiments, the desmopressin oral liquid composition contains no more than 5% wt of total impurities and not more than 1% wt of each of the peptide related impurities after stored at refrigerated conditions for 9 months. In some embodiments, the desmopressin oral liquid composition contains no more than 5% wt of total impurities and not more than 1% wt of each of the peptide related impurities after stored at refrigerated conditions for 12 months. In some embodiments, the desmopressin oral liquid composition contains no more than 5% wt of total impurities and not more than 1% wt of each of the peptide related impurities after stored at refrigerated conditions for 15 months. In some embodiments, the desmopressin oral liquid composition contains no more than 5% wt of total impurities and not more than 1% wt of each of the peptide related impurities after stored at refrigerated conditions for 18 months. In some embodiments, the desmopressin oral liquid composition contains no more than 5% wt of total impurities and not more than 1% wt of each of the peptide related impurities after stored at refrigerated conditions for 24 months. In some embodiments, the desmopressin oral liquid composition contains no more than 5% wt of total impurities and not more than 1% wt of each of the peptide related impurities after stored at refrigerated conditions for 30 months. In some embodiments, the desmopressin oral liquid composition contains no more than 5% wt of total impurities and not more than 1% wt of each of the peptide related impurities after stored at refrigerated conditions for 36 months.

In some embodiments, a desmopressin oral liquid composition contains no more than 3% wt of total impurities and not more than 1% wt of each of the peptide related impurities after stored at refrigerated conditions for at least 3 months, at least 6 months, at least 9 months, at least 12 months, at least 15 months, at least 18 months, at least 24 months, at least 30 months, or at least 36 months. In some embodiments, the desmopressin oral liquid composition contains no more than 3% wt of total impurities and not more than 1% wt of each of the peptide related impurities after stored at refrigerated conditions for 3 months. In some embodiments, the desmopressin oral liquid composition contains no more than 3% wt of total impurities and not more than 1% wt of each of the peptide related impurities after stored at refrigerated conditions for 6 months. In some embodiments, the desmopressin oral liquid composition contains no more than 3% wt of total impurities and not more than 1% wt of each of the peptide related impurities after stored at refrigerated conditions for 9 months. In some embodiments, the desmopressin oral liquid composition contains no more than 3% wt of total impurities and not more than 1% wt of each of the peptide related impurities after stored at refrigerated conditions for 12 months. In some embodiments, the desmopressin oral liquid composition contains no more than 3% wt of total impurities and not more than 1% wt of each of the peptide related impurities after stored at refrigerated conditions for 15 months. In some embodiments, the desmopressin oral liquid composition contains no more than 3% wt of total impurities and not more than 1% wt of each of the peptide related impurities after stored at refrigerated conditions for 18 months. In some embodiments, the desmopressin oral liquid composition contains no more than 3% wt of total impurities and not more than 1% wt of each of the peptide related impurities after stored at refrigerated conditions for 24 months. In some embodiments, the desmopressin oral liquid composition contains no more than 3% wt of total impurities and not more than 1% wt of each of the peptide related impurities after stored at refrigerated conditions for 30 months. In some embodiments, the desmopressin oral liquid composition contains no more than 3% wt of total impurities and not more than 1% wt of each of the peptide related impurities after stored at refrigerated conditions for 36 months.

In some embodiments, a desmopressin oral liquid composition described herein retains at least 90% wt of the initial desmopressin acetate amount after stored at refrigerated conditions for at least 3 months, at least 6 months, at least 9 months, at least 12 months, at least 15 months, at least 18 months, at least 24 months, at least 30 months, or at least 36 months. In some embodiments, the desmopressin oral liquid composition retains at least 90% wt of the initial desmopressin acetate amount after stored at refrigerated conditions for 3 months. In some embodiments, the desmopressin oral liquid composition retains at least 90% wt of the initial desmopressin acetate amount after stored at refrigerated conditions for 6 months. In some embodiments, the desmopressin oral liquid composition retains at least 90% wt of the initial desmopressin acetate amount after stored at refrigerated conditions for 9 months. In some embodiments, the desmopressin oral liquid composition retains at least 90% wt of the initial desmopressin acetate amount after stored at refrigerated conditions for 12 months. In some embodiments, the desmopressin oral liquid composition retains at least 90% wt of the initial desmopressin acetate amount after stored at refrigerated conditions for 15 months. In some embodiments, the desmopressin oral liquid composition retains at least 90% wt of the initial desmopressin acetate amount after stored at refrigerated conditions for 18 months. In some embodiments, the desmopressin oral liquid composition retains at least 90% wt of the initial desmopressin acetate amount after stored at refrigerated conditions for 24 months. In some embodiments, the desmopressin oral liquid composition retains at least 90% wt of the initial desmopressin acetate amount after stored at refrigerated conditions for 30 months. In some embodiments, the desmopressin oral liquid composition retains at least 90% wt of the initial desmopressin acetate amount after stored at refrigerated conditions for 36 months.

In some embodiments, a desmopressin oral liquid composition described herein at least 95% wt of the initial desmopressin acetate amount after stored at refrigerated conditions for at least 3 months, at least 6 months, at least 9 months, at least 12 months, at least 15 months, at least 18 months, at least 24 months, at least 30 months, or at least 36 months. In some embodiments, the desmopressin oral liquid composition retains at least 95% wt of the initial desmopressin acetate amount after stored at refrigerated conditions for 3 months. In some embodiments, the desmopressin oral liquid composition retains at least 95% wt of the initial desmopressin acetate amount after stored at refrigerated conditions for 6 months. In some embodiments, the desmopressin oral liquid composition retains at least 95% wt of the initial desmopressin acetate amount after stored at refrigerated conditions for 9 months. In some embodiments, the desmopressin oral liquid composition retains at least 95% wt of the initial desmopressin acetate amount after stored at refrigerated conditions for 12 months. In some embodiments, the desmopressin oral liquid composition retains at least 95% wt of the initial desmopressin acetate amount after stored at refrigerated conditions for 15 months. In some embodiments, the desmopressin oral liquid composition retains at least 95% wt of the initial desmopressin acetate amount after stored at refrigerated conditions for 18 months. In some embodiments, the desmopressin oral liquid composition retains at least 95% wt of the initial desmopressin acetate amount after stored at refrigerated conditions for 24 months. In some embodiments, the desmopressin oral liquid composition retains at least 95% wt of the initial desmopressin acetate amount after stored at refrigerated conditions for 30 months. In some embodiments, the desmopressin oral liquid composition retains at least 95% wt of the initial desmopressin acetate amount after stored at refrigerated conditions for 36 months.

In some embodiments, desmopressin acetate liquid compositions described herein are stable after stored at ambient or room temperature conditions for at least 1 month, at least 2 months, at least 3 months, at least 6 months, at least 9 months, at least 12 months, at least 15 months, at least 18 months, and at least 24 months. In some embodiments, temperature excursions are permitted when the desmopressin acetate liquid compositions are stored at room temperature conditions. In some embodiments, temperature excursions for room temperature conditions are permitted up to 30° C. In some embodiments, the desmopressin oral liquid formulations described herein are stable after stored at ambient or room temperature conditions with temperature excursions permitted up to 30° C. for at least 1 month, at least 2 months, at least 3 months, at least 6 months, at least 9 months, at least 12 months, at least 15 months, at least 18 months, and at least 24 months.

In some embodiments, the desmopressin oral liquid composition described herein contains no more than 5% wt of total impurities and not more than 1% wt of each of the peptide related impurities after stored at about 15° C. to about 25° C. for at least 3 months, at least 6 months, at least 9 months, at least 12 months, at least 15 months, at least 18 months, or at least 24 months. In some embodiments, the desmopressin oral liquid composition contains no more than 5% wt of total impurities and not more than 1% wt of each of the peptide related impurities after stored at about 15° C. to about 25° C. for 3 months. In some embodiments, the desmopressin oral liquid composition contains no more than 5% wt of total impurities and not more than 1% wt of each of the peptide related impurities after stored at about 15° C. to about 25° C. for 6 months. In some embodiments, the desmopressin oral liquid composition contains no more than 5% wt of total impurities and not more than 1% wt of each of the peptide related impurities after stored at about 15° C. to about 25° C. for 9 months. In some embodiments, the desmopressin oral liquid composition contains no more than 5% wt of total impurities and not more than 1% wt of each of the peptide related impurities after stored at about 15° C. to about 25° C. for 12 months. In some embodiments, the desmopressin oral liquid composition contains no more than 5% wt of total impurities and not more than 1% wt of each of the peptide related impurities after stored at about 15° C. to about 25° C. for 15 months. In some embodiments, the desmopressin oral liquid composition contains no more than 5% wt of total impurities and not more than 1% wt of each of the peptide related impurities after stored at about 15° C. to about 25° C. for 18 months. In some embodiments, the desmopressin oral liquid composition contains no more than 5% wt of total impurities and not more than 1% wt of each of the peptide related impurities after stored at about 15° C. to about 25° C. for 24 months.

In some embodiments, a desmopressin oral liquid composition contains no more than 3% wt of total impurities and not more than 1% wt of each of the peptide related impurities after stored at about 15° C. to about 25° C. for at least 3 months, at least 6 months, at least 9 months, at least 12 months, at least 15 months, at least 18 months, or at least 24 months. In some embodiments, the desmopressin oral liquid composition contains no more than 3% wt of total impurities and not more than 1% wt of each of the peptide related impurities after stored at about 15° C. to about 25° C. for 3 months. In some embodiments, the desmopressin oral liquid composition contains no more than 3% wt of total impurities and not more than 1% wt of each of the peptide related impurities after stored at about 15° C. to about 25° C. for 6 months. In some embodiments, the desmopressin oral liquid composition contains no more than 3% wt of total impurities and not more than 1% wt of each of the peptide related impurities after stored at about 15° C. to about 25° C. for 9 months. In some embodiments, the desmopressin oral liquid composition contains no more than 3% wt of total impurities and not more than 1% wt of each of the peptide related impurities after stored at about 15° C. to about 25° C. for 12 months. In some embodiments, the desmopressin oral liquid composition contains no more than 3% wt of total impurities and not more than 1% wt of each of the peptide related impurities after stored at about 15° C. to about 25° C. for 15 months. In some embodiments, the desmopressin oral liquid composition contains no more than 3% wt of total impurities and not more than 1% wt of each of the peptide related impurities after stored at about 15° C. to about 25° C. for 18 months. In some embodiments, the desmopressin oral liquid composition contains no more than 3% wt of total impurities and not more than 1% wt of each of the peptide related impurities after stored at about 15° C. to about 25° C. for 24 months.

In some embodiments, a desmopressin oral liquid composition described herein retains at least 90% wt of the initial desmopressin acetate amount after stored at about 15° C. to about 25° C. for at least 3 months, at least 6 months, at least 9 months, at least 12 months, at least 15 months, at least 18 months, or at least 24 months. In some embodiments, the desmopressin oral liquid composition retains at least 90% wt of the initial desmopressin acetate amount after stored at about 15° C. to about 25° C. for 3 months. In some embodiments, the desmopressin oral liquid composition retains at least 90% wt of the initial desmopressin acetate amount after stored at about 15° C. to about 25° C. for 6 months. In some embodiments, the desmopressin oral liquid composition retains at least 90% wt of the initial desmopressin acetate amount after stored at about 15° C. to about 25° C. for 9 months. In some embodiments, the desmopressin oral liquid composition retains at least 90% wt of the initial desmopressin acetate amount after stored at about 15° C. to about 25° C. for 12 months. In some embodiments, the desmopressin oral liquid composition retains at least 90% wt of the initial desmopressin acetate amount after stored at about 15° C. to about 25° C. for 15 months. In some embodiments, the desmopressin oral liquid composition retains at least 90% wt of the initial desmopressin acetate amount after stored at about 15° C. to about 25° C. for 18 months. In some embodiments, the desmopressin oral liquid composition retains at least 90% wt of the initial desmopressin acetate amount after stored at about 15° C. to about 25° C. for 24 months.

In some embodiments, a desmopressin oral liquid composition described herein retains at least 95% wt of the initial desmopressin acetate amount after stored at about 15° C. to about 25° C. for at least 3 months, at least 6 months, at least 9 months, at least 12 months, at least 15 months, at least 18 months, or at least 24 months. In some embodiments, the desmopressin oral liquid composition retains at least 95% wt of the initial desmopressin acetate amount after stored at about 15° C. to about 25° C. for 3 months. In some embodiments, the desmopressin oral liquid composition retains at least 95% wt of the initial desmopressin acetate amount after stored at about 15° C. to about 25° C. for 6 months. In some embodiments, the desmopressin oral liquid composition retains at least 95% wt of the initial desmopressin acetate amount after stored at about 15° C. to about 25° C. for 9 months. In some embodiments, the desmopressin oral liquid composition retains at least 95% wt of the initial desmopressin acetate amount after stored at about 15° C. to about 25° C. for 12 months. In some embodiments, the desmopressin oral liquid composition retains at least 95% wt of the initial desmopressin acetate amount after stored at about 15° C. to about 25° C. for 15 months. In some embodiments, the desmopressin oral liquid composition retains at least 95% wt of the initial desmopressin acetate amount after stored at about 15° C. to about 25° C. for 18 months. In some embodiments, the desmopressin oral liquid composition retains at least 95% wt of the initial desmopressin acetate amount after stored at about 15° C. to about 25° C. for 24 months.

In some embodiments, a desmopressin oral liquid composition described herein contains no more than 5% wt of total impurities and not more than 1% wt of each of the peptide related impurities after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 3 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 6 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 9 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 12 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 15 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 18 months. In some embodiments, the desmopressin oral liquid composition contains no more than 5% wt of total impurities and not more than 1% wt of each of the peptide related impurities after stored at about 15° C. to about 25° C., with temperature excursions permitted up to 30° C., for 24 months.

In some embodiments, a desmopressin oral liquid composition described herein contains no more than 3% wt of total impurities and not more than 1% wt of each of the peptide related impurities after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 3 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 6 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 9 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 12 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 15 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 18 months. In some embodiments, the desmopressin oral liquid composition contains no more than 3% wt of total impurities and not more than 1% wt of each of the peptide related impurities after stored at about 15° C. to about 25° C., with temperature excursions permitted up to 30° C., for 24 months.

In some embodiments, a desmopressin oral liquid composition described herein retains at least 90% wt of the initial desmopressin acetate amount after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the desmopressin oral liquid composition retains at least 90% wt of the initial desmopressin acetate amount after stored at about 15° C. to about 25° C., with temperature excursions permitted up to 30° C., for 3 months. In some embodiments, the desmopressin oral liquid composition retains at least 90% wt of the initial desmopressin acetate amount after stored at about 15° C. to about 25° C., with temperature excursions permitted up to 30° C., for 6 months. In some embodiments, the desmopressin oral liquid composition retains at least 90% wt of the initial desmopressin acetate amount after stored at about 15° C. to about 25° C., with temperature excursions permitted up to 30° C., for 12 months. In some embodiments, the desmopressin oral liquid composition retains at least 90% wt of the initial desmopressin acetate amount after stored at about 15° C. to about 25° C., with temperature excursions permitted up to 30° C., for 15 months. In some embodiments, the desmopressin oral liquid composition retains at least 90% wt of the initial desmopressin acetate amount after stored at about 15° C. to about 25° C., with temperature excursions permitted up to 30° C., for 18 months. In some embodiments, the desmopressin oral liquid composition retains at least 90% wt of the initial desmopressin acetate amount after stored at about 15° C. to about 25° C., with temperature excursions permitted up to 30° C., for 24 months.

In some embodiments, a desmopressin oral liquid composition described herein retains at least 95% wt of the initial desmopressin acetate amount after stored at about 15° C. to about 25° C., with temperature excursions permitted up to 30° C., for at least 3 months, at least 6 months, at least 9 months, at least 12 months, at least 15 months, at least 18 months, or at least 24 months. In some embodiments, the desmopressin oral liquid composition retains at least 95% wt of the initial desmopressin acetate amount after stored at about 15° C. to about 25° C., with temperature excursions permitted up to 30° C., for 3 months. In some embodiments, the desmopressin oral liquid composition retains at least 95% wt of the initial desmopressin acetate amount after stored at about 15° C. to about 25° C., with temperature excursions permitted up to 30° C., for 6 months. In some embodiments, the desmopressin oral liquid composition retains at least 95% wt of the initial desmopressin acetate amount after stored at about 15° C. to about 25° C., with temperature excursions permitted up to 30° C., for 9 months. In some embodiments, the desmopressin oral liquid composition retains at least 95% wt of the initial desmopressin acetate amount after stored at about 15° C. to about 25° C., with temperature excursions permitted up to 30° C., for 12 months. In some embodiments, the desmopressin oral liquid composition retains at least 95% wt of the initial desmopressin acetate amount after stored at about 15° C. to about 25° C., with temperature excursions permitted up to 30° C., for 15 months. In some embodiments, the desmopressin oral liquid composition retains at least 95% wt of the initial desmopressin acetate amount after stored at about 15° C. to about 25° C., with temperature excursions permitted up to 30° C., for 18 months. In some embodiments, the desmopressin oral liquid composition retains at least 95% wt of the initial desmopressin acetate amount after stored at about 15° C. to about 25° C., with temperature excursions permitted up to 30° C., for 24 months.

In some embodiments, the desmopressin oral liquid composition described herein contains no more than 5% wt of total impurities and not more than 1% wt of each of the peptide related impurities after stored at about 15° C. to about 30° C. for at least 3 months, at least 6 months, at least 9 months, at least 12 months, at least 15 months, at least 18 months, or at least 24 months. In some embodiments, the desmopressin oral liquid composition contains no more than 5% wt of total impurities and not more than 1% wt of each of the peptide related impurities after stored at about 15° C. to about 30° C. for 3 months. In some embodiments, the desmopressin oral liquid composition contains no more than 5% wt of total impurities and not more than 1% wt of each of the peptide related impurities after stored at about 15° C. to about 30° C. for 6 months. In some embodiments, the desmopressin oral liquid composition contains no more than 5% wt of total impurities and not more than 1% wt of each of the peptide related impurities after stored at about 15° C. to about 30° C. for 9 months. In some embodiments, the desmopressin oral liquid composition contains no more than 5% wt of total impurities and not more than 1% wt of each of the peptide related impurities after stored at about 15° C. to about 30° C. for 12 months. In some embodiments, the desmopressin oral liquid composition contains no more than 5% wt of total impurities and not more than 1% wt of each of the peptide related impurities after stored at about 15° C. to about 30° C. for 15 months. In some embodiments, the desmopressin oral liquid composition contains no more than 5% wt of total impurities and not more than 1% wt of each of the peptide related impurities after stored at about 15° C. to about 30° C. for 18 months. In some embodiments, the desmopressin oral liquid composition contains no more than 5% wt of total impurities and not more than 1% wt of each of the peptide related impurities after stored at about 15° C. to about 30° C. for 24 months.

In some embodiments, a desmopressin oral liquid composition contains no more than 3% wt of total impurities and not more than 1% wt of each of the peptide related impurities after stored at about 15° C. to about 30° C. for at least 3 months, at least 6 months, at least 9 months, at least 12 months, at least 15 months, at least 18 months, or at least 24 months. In some embodiments, the desmopressin oral liquid composition contains no more than 3% wt of total impurities and not more than 1% wt of each of the peptide related impurities after stored at about 15° C. to about 30° C. for 3 months. In some embodiments, the desmopressin oral liquid composition contains no more than 3% wt of total impurities and not more than 1% wt of each of the peptide related impurities after stored at about 15° C. to about 30° C. for 6 months. In some embodiments, the desmopressin oral liquid composition contains no more than 3% wt of total impurities and not more than 1% wt of each of the peptide related impurities after stored at about 15° C. to about 30° C. for 9 months. In some embodiments, the desmopressin oral liquid composition contains no more than 3% wt of total impurities and not more than 1% wt of each of the peptide related impurities after stored at about 15° C. to about 30° C. for 12 months. In some embodiments, the desmopressin oral liquid composition contains no more than 3% wt of total impurities and not more than 1% wt of each of the peptide related impurities after stored at about 15° C. to about 30° C. for 15 months. In some embodiments, the desmopressin oral liquid composition contains no more than 3% wt of total impurities and not more than 1% wt of each of the peptide related impurities after stored at about 15° C. to about 30° C. for 18 months. In some embodiments, the desmopressin oral liquid composition contains no more than 3% wt of total impurities and not more than 1% wt of each of the peptide related impurities after stored at about 15° C. to about 30° C. for 24 months.

In some embodiments, a desmopressin oral liquid composition described herein retains at least 90% wt of the initial desmopressin acetate amount after stored at about 15° C. to about 30° C. for at least 3 months, at least 6 months, at least 9 months, at least 12 months, at least 15 months, at least 18 months, or at least 24 months. In some embodiments, the desmopressin oral liquid composition retains at least 90% wt of the initial desmopressin acetate amount after stored at about 15° C. to about 30° C. for 3 months. In some embodiments, the desmopressin oral liquid composition retains at least 90% wt of the initial desmopressin acetate amount after stored at about 15° C. to about 30° C. for 6 months. In some embodiments, the desmopressin oral liquid composition retains at least 90% wt of the initial desmopressin acetate amount after stored at about 15° C. to about 30° C. for 9 months. In some embodiments, the desmopressin oral liquid composition retains at least 90% wt of the initial desmopressin acetate amount after stored at about 15° C. to about 30° C. for 12 months. In some embodiments, the desmopressin oral liquid composition retains at least 90% wt of the initial desmopressin acetate amount after stored at about 15° C. to about 30° C. for 15 months. In some embodiments, the desmopressin oral liquid composition retains at least 90% wt of the initial desmopressin acetate amount after stored at about 15° C. to about 30° C. for 18 months. In some embodiments, the desmopressin oral liquid composition retains at least 90% wt of the initial desmopressin acetate amount after stored at about 15° C. to about 30° C. for 24 months.

In some embodiments, a desmopressin oral liquid composition described herein retains at least 95% wt of the initial desmopressin acetate amount after stored at about 15° C. to about 30° C. for at least 3 months, at least 6 months, at least 9 months, at least 12 months, at least 15 months, at least 18 months, or at least 24 months. In some embodiments, the desmopressin oral liquid composition retains at least 95% wt of the initial desmopressin acetate amount after stored at about 15° C. to about 30° C. for 3 months. In some embodiments, the desmopressin oral liquid composition retains at least 95% wt of the initial desmopressin acetate amount after stored at about 15° C. to about 30° C. for 6 months. In some embodiments, the desmopressin oral liquid composition retains at least 95% wt of the initial desmopressin acetate amount after stored at about 15° C. to about 30° C. for 9 months. In some embodiments, the desmopressin oral liquid composition retains at least 95% wt of the initial desmopressin acetate amount after stored at about 15° C. to about 30° C. for 12 months. In some embodiments, the desmopressin oral liquid composition retains at least 95% wt of the initial desmopressin acetate amount after stored at about 15° C. to about 30° C. for 15 months. In some embodiments, the desmopressin oral liquid composition retains at least 95% wt of the initial desmopressin acetate amount after stored at about 15° C. to about 30° C. for 18 months. In some embodiments, the desmopressin oral liquid composition retains at least 95% wt of the initial desmopressin acetate amount after stored at about 15° C. to about 30° C. for 24 months.

In some embodiments, a desmopressin oral liquid composition described herein contains no more than 5% wt of total impurities and not more than 1% wt of each of the peptide related impurities after stored at room temperature for at least 3 months, at least 6 months, at least 9 months, at least 12 months, at least 15 months, at least 18 months, or at least 24 months. In some embodiments, the desmopressin oral liquid composition contains no more than 5% wt of total impurities and not more than 1% wt of each of the peptide related impurities after stored at room temperature for 3 months. In some embodiments, the desmopressin oral liquid composition contains no more than 5% wt of total impurities and not more than 1% wt of each of the peptide related impurities after stored at room temperature for 6 months. In some embodiments, the desmopressin oral liquid composition contains no more than 5% wt of total impurities and not more than 1% wt of each of the peptide related impurities after stored at room temperature for 9 months. In some embodiments, the desmopressin oral liquid composition contains no more than 5% wt of total impurities and not more than 1% wt of each of the peptide related impurities after stored at room temperature for 12 months. In some embodiments, the desmopressin oral liquid composition contains no more than 5% wt of total impurities and not more than 1% wt of each of the peptide related impurities after stored at room temperature for 15 months. In some embodiments, the desmopressin oral liquid composition contains no more than 5% wt of total impurities and not more than 1% wt of each of the peptide related impurities after stored at room temperature for 18 months. In some embodiments, the desmopressin oral liquid composition contains no more than 5% wt of total impurities and not more than 1% wt of each of the peptide related impurities after stored at room temperature for 24 months.

In some embodiments, a desmopressin oral liquid composition described herein contains no more than 3% wt of total impurities and not more than 1% wt of each of the peptide related impurities after stored at room temperature for at least 3 months, at least 6 months, at least 9 months, at least 12 months, at least 15 months, at least 18 months, or at least 24 months. In some embodiments, the desmopressin oral liquid composition contains no more than 3% wt of total impurities and not more than 1% wt of each of the peptide related impurities after stored at room temperature for 3 months. In some embodiments, the desmopressin oral liquid composition contains no more than 3% wt of total impurities and not more than 1% wt of each of the peptide related impurities after stored at room temperature for 6 months. In some embodiments, the desmopressin oral liquid composition contains no more than 3% wt of total impurities and not more than 1% wt of each of the peptide related impurities after stored at room temperature for 9 months. In some embodiments, the desmopressin oral liquid composition contains no more than 3% wt of total impurities and not more than 1% wt of each of the peptide related impurities after stored at room temperature for 12 months. In some embodiments, the desmopressin oral liquid composition contains no more than 3% wt of total impurities and not more than 1% wt of each of the peptide related impurities after stored at room temperature for 15 months. In some embodiments, the desmopressin oral liquid composition contains no more than 3% wt of total impurities and not more than 1% wt of each of the peptide related impurities after stored at room temperature for 18 months. In some embodiments, the desmopressin oral liquid composition contains no more than 3% wt of total impurities and not more than 1% wt of each of the peptide related impurities after stored at room temperature for 24 months.

In some embodiments, a desmopressin oral liquid composition described herein retains at least 90% wt of the initial desmopressin acetate amount after stored at room temperature for at least 3 months, at least 6 months, at least 9 months, at least 12 months, at least 15 months, at least 18 months, or at least 24 months. In some embodiments, the desmopressin oral liquid composition retains at least 90% wt of the initial desmopressin acetate amount after stored at room temperature for 3 months. In some embodiments, the desmopressin oral liquid composition retains at least 90% wt of the initial desmopressin acetate amount after stored at room temperature for 6 months. In some embodiments, the desmopressin oral liquid composition retains at least 90% wt of the initial desmopressin acetate amount after stored at room temperature for 9 months. In some embodiments, the desmopressin oral liquid composition retains at least 90% wt of the initial desmopressin acetate amount after stored at room temperature for 12 months. In some embodiments, the desmopressin oral liquid composition retains at least 90% wt of the initial desmopressin acetate amount after stored at room temperature for 15 months. In some embodiments, the desmopressin oral liquid composition retains at least 90% wt of the initial desmopressin acetate amount after stored at room temperature for 18 months. In some embodiments, the desmopressin oral liquid composition retains at least 90% wt of the initial desmopressin acetate amount after stored at room temperature for 24 months.

In some embodiments, a desmopressin oral liquid composition described herein retains at least 95% wt of the initial desmopressin acetate amount after stored at room temperature for at least 3 months, at least 6 months, at least 9 months, at least 12 months, at least 15 months, at least 18 months, or at least 24 months. In some embodiments, the desmopressin oral liquid composition retains at least 95% wt of the initial desmopressin acetate amount after stored at room temperature for 3 months. In some embodiments, the desmopressin oral liquid composition retains at least 95% wt of the initial desmopressin acetate amount after stored at room temperature for 6 months. In some embodiments, the desmopressin oral liquid composition retains at least 95% wt of the initial desmopressin acetate amount after stored at room temperature for 9 months. In some embodiments, the desmopressin oral liquid composition retains at least 95% wt of the initial desmopressin acetate amount after stored at room temperature for 12 months. In some embodiments, the desmopressin oral liquid composition retains at least 95% wt of the initial desmopressin acetate amount after stored at room temperature for 15 months. In some embodiments, the desmopressin oral liquid composition retains at least 95% wt of the initial desmopressin acetate amount after stored at room temperature for 18 months. In some embodiments, the desmopressin oral liquid composition retains at least 95% wt of the initial desmopressin acetate amount after stored at room temperature for 24 months.

In some embodiments, a desmopressin oral liquid composition described herein contains no more than 5% wt of total impurities and not more than 1% wt of each of the peptide related impurities after stored at ambient conditions for at least 3 months, at least 6 months, at least 9 months, at least 12 months, at least 15 months, at least 18 months, or at least 24 months. In some embodiments, the desmopressin oral liquid composition contains no more than 5% wt of total impurities and not more than 1% wt of each of the peptide related impurities after stored at ambient conditions for 3 months. In some embodiments, the desmopressin oral liquid composition contains no more than 5% wt of total impurities and not more than 1% wt of each of the peptide related impurities after stored at ambient conditions for 6 months. In some embodiments, the desmopressin oral liquid composition contains no more than 5% wt of total impurities and not more than 1% wt of each of the peptide related impurities after stored at ambient conditions for 9 months. In some embodiments, the desmopressin oral liquid composition contains no more than 5% wt of total impurities and not more than 1% wt of each of the peptide related impurities after stored at ambient conditions for 12 months. In some embodiments, the desmopressin oral liquid composition contains no more than 5% wt of total impurities and not more than 1% wt of each of the peptide related impurities after stored at ambient conditions for 15 months. In some embodiments, the desmopressin oral liquid composition contains no more than 5% wt of total impurities and not more than 1% wt of each of the peptide related impurities after stored at ambient conditions for 18 months. In some embodiments, the desmopressin oral liquid composition contains no more than 5% wt of total impurities and not more than 1% wt of each of the peptide related impurities after stored at ambient conditions for 24 months.

In some embodiments, a desmopressin oral liquid composition described herein contains no more than 3% wt of total impurities and not more than 1% wt of each of the peptide related impurities after stored at ambient conditions for at least 3 months, at least 6 months, at least 9 months, at least 12 months, at least 15 months, at least 18 months, or at least 24 months. In some embodiments, the desmopressin oral liquid composition contains no more than 3% wt of total impurities and not more than 1% wt of each of the peptide related impurities after stored at ambient conditions for 3 months. In some embodiments, the desmopressin oral liquid composition contains no more than 3% wt of total impurities and not more than 1% wt of each of the peptide related impurities after stored at ambient conditions for 6 months. In some embodiments, the desmopressin oral liquid composition contains no more than 3% wt of total impurities and not more than 1% wt of each of the peptide related impurities after stored at ambient conditions for 9 months. In some embodiments, the desmopressin oral liquid composition contains no more than 3% wt of total impurities and not more than 1% wt of each of the peptide related impurities after stored at ambient conditions for 12 months. In some embodiments, the desmopressin oral liquid composition contains no more than 3% wt of total impurities and not more than 1% wt of each of the peptide related impurities after stored at ambient conditions for 15 months. In some embodiments, the desmopressin oral liquid composition contains no more than 3% wt of total impurities and not more than 1% wt of each of the peptide related impurities after stored at ambient conditions for 18 months. In some embodiments, the desmopressin oral liquid composition contains no more than 3% wt of total impurities and not more than 1% wt of each of the peptide related impurities after stored at ambient conditions for 24 months.

In some embodiments, a desmopressin oral liquid composition described herein retains at least 90% wt of the initial desmopressin acetate amount after stored at ambient conditions for at least 3 months, at least 6 months, at least 9 months, at least 12 months, at least 15 months, at least 18 months, or at least 24 months. In some embodiments, the desmopressin oral liquid composition retains at least 90% wt of the initial desmopressin acetate amount after stored at ambient conditions for 3 months. In some embodiments, the desmopressin oral liquid composition retains at least 90% wt of the initial desmopressin acetate amount after stored at ambient conditions for 6 months. In some embodiments, the desmopressin oral liquid composition retains at least 90% wt of the initial desmopressin acetate amount after stored at ambient conditions for 9 months. In some embodiments, the desmopressin oral liquid composition retains at least 90% wt of the initial desmopressin acetate amount after stored at ambient conditions for 12 months. In some embodiments, the desmopressin oral liquid composition retains at least 90% wt of the initial desmopressin acetate amount after stored at ambient conditions for 15 months. In some embodiments, the desmopressin oral liquid composition retains at least 90% wt of the initial desmopressin acetate amount after stored at ambient conditions for 18 months. In some embodiments, the desmopressin oral liquid composition retains at least 90% wt of the initial desmopressin acetate amount after stored at ambient conditions for 24 months.

In some embodiments, a desmopressin oral liquid composition described herein retains at least 95% wt of the initial desmopressin acetate amount after stored at ambient conditions for at least 3 months, at least 6 months, at least 9 months, at least 12 months, at least 15 months, at least 18 months, or at least 24 months. In some embodiments, the desmopressin oral liquid composition retains at least 95% wt of the initial desmopressin acetate amount after stored at ambient conditions for 3 months. In some embodiments, the desmopressin oral liquid composition retains at least 95% wt of the initial desmopressin acetate amount after stored at ambient conditions for 6 months. In some embodiments, the desmopressin oral liquid composition retains at least 95% wt of the initial desmopressin acetate amount after stored at ambient conditions for 9 months. In some embodiments, the desmopressin oral liquid composition retains at least 95% wt of the initial desmopressin acetate amount after stored at ambient conditions for 12 months. In some embodiments, the desmopressin oral liquid composition retains at least 95% wt of the initial desmopressin acetate amount after stored at ambient conditions for 15 months. In some embodiments, the desmopressin oral liquid composition retains at least 95% wt of the initial desmopressin acetate amount after stored at ambient conditions for 18 months. In some embodiments, the desmopressin oral liquid composition retains at least 95% wt of the initial desmopressin acetate amount after stored at ambient conditions for 24 months.

In some embodiments, desmopressin oral liquid formulations described herein are stable after stored at accelerated conditions, for at least 1 month, at least 2 months, at least 3 months, at least 4 months, at least 5 months, at least 6 months, at least 7 months, at least 8 months, at least 9 months, at least 10 months, at least 11 months or at least 12 months. In some embodiments, the desmopressin oral liquid formulations described herein are stable after stored at about 40° C.±2° C., for at least 1 month, at least 2 months, at least 3 months, at least 4 months, at least 5 months, at least 6 months, at least 7 months, at least 8 months, at least 9 months, at least 10 months, at least 11 months or at least 12 months.

In some embodiments, a desmopressin oral liquid composition described herein contains no more than 5% wt of total impurities and not more than 1% wt of each of the peptide related impurities after stored at about 40° C.±2° C. for at least 3 months, at least 6 months, at least 9 months, or at least 12 months. In some embodiments, the desmopressin oral liquid composition contains no more than 5% wt of total impurities and not more than 1% wt of each of the peptide related impurities after stored at about 40° C.±2° C. for 3 months. In some embodiments, the desmopressin oral liquid composition contains no more than 5% wt of total impurities and not more than 1% wt of each of the peptide related impurities after stored at about 40° C.±2° C. for 6 months. In some embodiments, the desmopressin oral liquid composition contains no more than 5% wt of total impurities and not more than 1% wt of each of the peptide related impurities after stored at about 40° C.±2° C. for 9 months. In some embodiments, the desmopressin oral liquid composition contains no more than 5% wt of total impurities and not more than 1% wt of each of the peptide related impurities after stored at about 40° C.±2° C. for 12 months.

In some embodiments, a desmopressin oral liquid composition described herein contains no more than 3% wt of total impurities and not more than 1% wt of each of the peptide related impurities after stored at about 40° C.±2° C. for at least 3 months, at least 6 months, at least 9 months, at or least 12 months. In some embodiments, the desmopressin oral liquid composition contains no more than 3% wt of total impurities and not more than 1% wt of each of the peptide related impurities after stored at about 40° C.±2° C. for 3 months. In some embodiments, the desmopressin oral liquid composition contains no more than 3% wt of total impurities and not more than 1% wt of each of the peptide related impurities after stored at about 40° C.±2° C. for 6 months. In some embodiments, the desmopressin oral liquid composition contains no more than 3% wt of total impurities and not more than 1% wt of each of the peptide related impurities after stored at about 40° C.±2° C. for 9 months. In some embodiments, the desmopressin oral liquid composition contains no more than 3% wt of total impurities and not more than 1% wt of each of the peptide related impurities after stored at about 40° C.±2° C. for 12 months.

In some embodiments, a desmopressin oral liquid composition described herein retains at least 90% wt of the initial desmopressin acetate amount after stored at about 40° C.±2° C. for at least 3 months, at least 6 months, at least 9 months, or at least 12 months. In some embodiments, the desmopressin oral liquid composition retains at least 90% wt of the initial desmopressin acetate amount after stored at about 40° C.±2° C. for 3 months. In some embodiments, the desmopressin oral liquid composition retains at least 90% wt of the initial desmopressin acetate amount after stored at about 40° C.±2° C. for 6 months. In some embodiments, the desmopressin oral liquid composition retains at least 90% wt of the initial desmopressin acetate amount after stored at about 40° C.±2° C. for 9 months. In some embodiments, the desmopressin oral liquid composition retains at least 90% wt of the initial desmopressin acetate amount after stored at about 40° C.±2° C. for 12 months.

In some embodiments, a desmopressin oral liquid composition described herein retains at least 95% wt of the initial desmopressin acetate amount after stored at about 40° C.±2° C. for at least 3 months, at least 6 months, at least 9 months, or at least 12 months. In some embodiments, the desmopressin oral liquid composition retains at least 95% wt of the initial desmopressin acetate amount after stored at about 40° C.±2° C. for 3 months. In some embodiments, the desmopressin oral liquid composition retains at least 95% wt of the initial desmopressin acetate amount after stored at about 40° C.±2° C. for 6 months. In some embodiments, the desmopressin oral liquid composition retains at least 95% wt of the initial desmopressin acetate amount after stored at about 40° C.±2° C. for 9 months. In some embodiments, the desmopressin oral liquid composition retains at least 95% wt of the initial desmopressin acetate amount after stored at about 40° C.±2° C. for 12 months.

In some embodiments, a desmopressin oral liquid composition described herein contains no more than 5% wt of total impurities and not more than 1% wt of each of the peptide related impurities after stored at accelerated conditions for at least 3 months, at least 6 months, at least 9 months, or at least 12 months. In some embodiments, the desmopressin oral liquid composition contains no more than 5% wt of total impurities and not more than 1% wt of each of the peptide related impurities after stored at accelerated conditions for 3 months. In some embodiments, the desmopressin oral liquid composition contains no more than 5% wt of total impurities and not more than 1% wt of each of the peptide related impurities after stored at accelerated conditions for 6 months. In some embodiments, the desmopressin oral liquid composition contains no more than 5% wt of total impurities and not more than 1% wt of each of the peptide related impurities after stored at accelerated conditions for 9 months. In some embodiments, the desmopressin oral liquid composition contains no more than 5% wt of total impurities and not more than 1% wt of each of the peptide related impurities after stored at accelerated conditions for 12 months.

In some embodiments, a desmopressin oral liquid composition described herein contains no more than 3% wt of total impurities and not more than 1% wt of each of the peptide related impurities after stored at accelerated conditions for at least 3 months, at least 6 months, at least 9 months, at or least 12 months. In some embodiments, the desmopressin oral liquid composition contains no more than 3% wt of total impurities and not more than 1% wt of each of the peptide related impurities after stored at accelerated conditions for 3 months. In some embodiments, the desmopressin oral liquid composition contains no more than 3% wt of total impurities and not more than 1% wt of each of the peptide related impurities after stored at accelerated conditions for 6 months. In some embodiments, the desmopressin oral liquid composition contains no more than 3% wt of total impurities and not more than 1% wt of each of the peptide related impurities after stored at accelerated conditions for 9 months. In some embodiments, the desmopressin oral liquid composition contains no more than 3% wt of total impurities and not more than 1% wt of each of the peptide related impurities after stored at accelerated conditions for 12 months.

In some embodiments, a desmopressin oral liquid composition described herein retains at least 90% wt of the initial desmopressin acetate amount after stored at accelerated conditions for at least 3 months, at least 6 months, at least 9 months, or at least 12 months. In some embodiments, the desmopressin oral liquid composition retains at least 90% wt of the initial desmopressin acetate amount after stored at accelerated conditions for 3 months. In some embodiments, the desmopressin oral liquid composition retains at least 90% wt of the initial desmopressin acetate amount after stored at accelerated conditions for 6 months. In some embodiments, the desmopressin oral liquid composition retains at least 90% wt of the initial desmopressin acetate amount after stored at accelerated conditions for 9 months. In some embodiments, the desmopressin oral liquid composition retains at least 90% wt of the initial desmopressin acetate amount after stored at accelerated conditions for 12 months.

In some embodiments, a desmopressin oral liquid composition described herein retains at least 95% wt of the initial desmopressin acetate amount after stored at accelerated conditions for at least 3 months, at least 6 months, at least 9 months, or at least 12 months. In some embodiments, the desmopressin oral liquid composition retains at least 95% wt of the initial desmopressin acetate amount after stored at accelerated conditions for 3 months. In some embodiments, the desmopressin oral liquid composition retains at least 95% wt of the initial desmopressin acetate amount after stored at accelerated conditions for 6 months. In some embodiments, the desmopressin oral liquid composition retains at least 95% wt of the initial desmopressin acetate amount after stored at accelerated conditions for 9 months. In some embodiments, the desmopressin oral liquid composition retains at least 95% wt of the initial desmopressin acetate amount after stored at accelerated conditions for 12 months.

In some embodiments, a desmopressin oral liquid composition described herein retains at least 95% wt of the initial desmopressin acetate amount after stored at 40° C.±2° C. and 75±5% RH for at least 6 months. In some embodiments, a desmopressin oral liquid composition described herein retains at least 96% wt of the initial desmopressin acetate amount after stored at 40° C.±2° C. and 75±5% RH for at least 6 months. In some embodiments, a desmopressin oral liquid composition described herein retains at least 97% wt of the initial desmopressin acetate amount after stored at 40° C.±2° C. and 75±5% RH for at least 6 months. In some embodiments, a desmopressin oral liquid composition described herein contains no more than 4% wt of total impurities and not more than 1% wt of each of the peptide related impurities after stored at 40° C.±2° C. and 75±5% RH for at least 6 months. In some embodiments, a desmopressin oral liquid composition described herein contains no more than 3.5% wt of total impurities and not more than 0.9% wt of each of the peptide related impurities after stored at 40° C.±2° C. and 75±5% RH for at least 6 months. In some embodiments, a desmopressin oral liquid composition described herein contains no more than 3% wt of total impurities and not more than 0.8% wt of each of the peptide related impurities after stored at 40° C.±2° C. and 75±5% RH for at least 6 months. In some embodiments, a desmopressin oral liquid composition described herein contains no more than 2.5% wt of total impurities and not more than 0.8% wt of each of the peptide related impurities after stored at 40° C.±2° C. and 75±5% RH for at least 6 months. In some embodiments, a desmopressin oral liquid composition described herein contains no more than 0.5% wt of [Gly$^9$OH]desmopressin after stored at 40° C.±2° C. and 75±5% RH for at least 6 months. In some embodiments, a desmopressin oral liquid composition described herein contains no more than 0.4% wt of [Asp$^5$]desmopressin after stored at 40° C.±2° C. and 75±5% RH for at least 6 months. In some embodiments, a desmopressin oral liquid composition described herein contains no more than 0.5% wt of [Glu$^4$]desmopressin after stored at 40° C.±2° C. and 75±5% RH for at least 6 months. In some embodiments, a desmopressin oral liquid composition described herein contains no more than 0.1% wt of [L-Arg$^9$]desmopressin after stored at 40° C.±2° C. and 75±5% RH for at least 6 months. In some embodiments, a desmopressin oral liquid composition described herein contains no more than 0.1% wt of [Asn$^5$(Acm)]desmopressin after stored at 40° C.±2° C. and 75±5% RH for at least 6 months. In some embodiments, a desmopressin oral liquid composition described herein has a pH of about 5.0 after stored at 40° C.±2° C. and 75±5% RH for at least 6 months. In some embodiments, a desmopressin oral liquid composition described herein maintains a pH of 5.0 after stored at 40° C.±2° C. and 75±5% RH for at least 6 months.

In some embodiments, desmopressin oral liquid formulations described herein are stable or shelf-stable when in use after stored in various conditions including refrigerated conditions, room temperature, ambient conditions, and accelerated conditions. Stable or shelf stable as used herein refer to desmopressin oral liquid formulations having about 95% or greater of the initial desmopressin acetate amount, no more than 3% wt of total impurities, and no more than 1% w/w of each of the peptide related impurities at the end of a given storage period. Alternatively, stable or shelf stable as used herein refer to desmopressin oral liquid formulations having about 90% wt or greater of initial desmopressin acetate amount, no more than 5% wt total impurities, and no more than 1% w/w of each of the peptide related impurities at the end of a given storage period. In some embodiments, the desmopressin oral liquid formulations are in use when stored in an opened container.

In some embodiments, a desmopressin oral liquid composition described herein are stable when in use after stored at room temperature or ambient conditions for at least 15 days, 30 days, 60 days, 90 days, or 120 days.

In some embodiments, a desmopressin liquid pharmaceutical composition described herein contains no more than 3% wt of total impurities and not more than 1% wt of each of the peptide related impurities when in use after stored at room temperature or ambient conditions for at least 15 days, 30 days, 60 days, 90 days, or 120 days. In some embodiments, the desmopressin liquid pharmaceutical composition contains no more than 3% wt of total impurities and not more than 1% wt of each of the peptide related impurities when in use after stored at room temperature or ambient conditions for at least 15 days. In some embodiments, the desmopressin liquid pharmaceutical composition contains no more than 3% wt of total impurities and not more than 1% wt of each of the peptide related impurities when in use after stored at room temperature or ambient conditions for at least 30 days. In some embodiments, the desmopressin liquid pharmaceutical composition contains no more than 3% wt of total impurities and not more than 1% wt of each of the peptide related impurities when in use after stored at room temperature or ambient conditions for at least 60 days. In some embodiments, the desmopressin liquid pharmaceutical composition contains no more than 3% wt of total impurities and not more than 1% wt of each of the peptide related impurities when in use after stored at room temperature or ambient conditions for at least 90 days. In some embodiments, the desmopressin liquid pharmaceutical composition contains no more than 3% wt of total impurities and not more than 1% wt of each of the peptide related impurities when in use after stored at room temperature or ambient conditions for at least 120 days.

In some embodiments, a desmopressin liquid pharmaceutical composition described herein contains no more than 5% wt of total impurities and not more than 1% wt of each of the peptide related impurities when in use after stored at room temperature or ambient conditions for at least 15 days, 30 days, 60 days, 90 days, or 120 days. In some embodiments, the desmopressin liquid pharmaceutical composition contains no more than 5% wt of total impurities and not more than 1% wt of each of the peptide related impurities when in use after stored at room temperature or ambient conditions for at least 15 days. In some embodiments, the desmopressin liquid pharmaceutical composition contains no more than 5% wt of total impurities and not more than 1% wt of each of the peptide related impurities when in use after stored at room temperature or ambient conditions for at least 30 days. In some embodiments, the desmopressin liquid pharmaceutical composition contains no more than 5% wt of total impurities and not more than 1% wt of each of the peptide related impurities when in use after stored at room temperature or ambient conditions for at least 60 days. In some embodiments, the desmopressin liquid pharmaceutical composition contains no more than 5% wt of total impurities and not more than 1% wt of each of the peptide related impurities when in use after stored at room temperature or ambient conditions for at least 90 days. In some embodiments, the desmopressin liquid pharmaceutical composition contains no more than 5% wt of total impurities and not more than 1% wt of each of the peptide related impurities when in use after stored at room temperature or ambient conditions for at least 120 days.

In some embodiments, a desmopressin liquid pharmaceutical composition described herein retains at least 95% wt of the initial desmopressin amount when in use after stored at room temperature or ambient conditions for at least 15 days, 30 days, 60 days, 90 days, or 120 days. In some embodiments, the desmopressin liquid pharmaceutical composition retains at least 95% wt of the initial desmopressin amount when in use after stored at room temperature or ambient conditions for at least 15 days. In some embodiments, the desmopressin liquid pharmaceutical composition retains at least 95% wt of the initial desmopressin amount when in use after stored at room temperature or ambient conditions for at least 30 days. In some embodiments, the desmopressin liquid pharmaceutical composition retains at least 95% wt of the initial desmopressin amount when in use after stored at room temperature or ambient conditions for at least 60 days. In some embodiments, the desmopressin liquid pharmaceutical composition retains at least 95% wt of the initial desmopressin amount when in use after stored at room temperature or ambient conditions for at least 90 days. In some embodiments, the desmopressin liquid pharmaceutical composition retains at least 95% wt of the initial desmopressin amount when in use after stored at room temperature or ambient conditions for at least 120 days.

In some embodiments, a desmopressin liquid pharmaceutical composition described herein retains at least 90% wt of the initial desmopressin amount when in use after stored at room temperature or ambient conditions for at least 15 days, 30 days, 60 days, 90 days, or 120 days. In some embodiments, the desmopressin liquid pharmaceutical composition retains at least 90% wt of the initial desmopressin amount when in use after stored at room temperature or ambient conditions for at least 15 days. In some embodiments, the desmopressin liquid pharmaceutical composition retains at least 90% wt of the initial desmopressin amount when in use after stored at room temperature or ambient conditions for at least 30 days. In some embodiments, the desmopressin liquid pharmaceutical composition retains at least 90% wt of the initial desmopressin amount when in use after stored at room temperature or ambient conditions for at least 60 days. In some embodiments, the desmopressin liquid pharmaceutical composition retains at least 90% wt of the initial desmopressin amount when in use after stored at room temperature or ambient conditions for at least 90 days. In some embodiments, the desmopressin liquid pharmaceutical composition retains at least 90% wt of the initial desmopressin amount when in use after stored at room temperature or ambient conditions for at least 120 days.

Refrigerated Condition, Room Temperature, Accelerated Conditions, Temperature Excursions Refrigerated temperature, also as defined by the USP, is between 2 and 8 degrees Celsius, and is sometimes designated by the nominal value of 5 degrees Celsius. In some embodiments, refrigerated temperatures can be defined as 5 f 3° C. In each case, the formulations described in the present disclosure that were shown to be stable showed acceptable recovery of the expected desmopressin acetate from the dose, where acceptable is >95% or alternately >90% of the nominal or starting dose of desmopressin acetate, as well as maintaining acceptably constant therapeutic potential. Refrigerated conditions include temperature and/or relative humidity (RH) in typical refrigeration units (e.g., 5±3° C.). In some instances, a refrigerated condition is about 2° C., about 3° C., about 4° C., about 5° C., about 6° C., about 7° C., or about 8° C. In some instances, a refrigerated condition is about 2° C. to about 8° C.

As used herein, the term "room temperature," "ambient conditions," or "ambient temperature" refers to room temperature or "controlled room temperature." In some embodiments, the room temperatures are about 15° C. to about 25° C. In some embodiments, the room temperatures are about 15° C. to about 30° C. In some embodiments, the room temperatures are 25 f 5° C. In some embodiments, the controlled room temperatures are about 20° C. to about 25° C. In some embodiments, ambient conditions are about 15° C. to about 30° C. In some embodiments, ambient conditions are about 25 f 5° C. and 60 f 5% RH. In some embodiments, ambient conditions are about 25 f 2° C. and 60 f 5% RH. In some embodiments, the room temperature is about 25° C. and about 60% RH. In some instances, a room temperature or ambient temperature is at about 20° C., about 21° C., about 22° C., about 23° C., about 24° C., about 25° C., about 26° C., about 27° C., about 28° C., about 29° C., and about 30° C. In other instances, an ambient condition is about 55% RH, about 60% RH, or about 65% RH.

As used herein, the term "temperature excursions" or "temperature excursion" refers to a deviation from a predetermined condition, such as a deviation from a "controlled room temperature." In some instances, the deviation is about ±5° C., ±6° C., ±7° C., ±8° C., ±9° C., ±10° C. from the controlled room temperature. In some instances, the deviation is about ±5° C. from the controlled room temperature. In some instances, temperature excursion for controlled room temperature is about 15° C. to about 30° C. In some instances, the temperature excursion takes place less than 1%, 2%, 3%, 4%, 5%, 10%, 15%, 20%, 30%, 40%, or 50% of the time during the entire period when the liquid pharmaceutical composition is measured for stability.

Accelerated conditions for the desmopressin oral liquid formulations described herein include temperature and/or relative humidity (RH) that are at or above ambient levels or room temperature (e.g., 25±5° C.; 55±10% RH). In some instances, an accelerated condition is at about 30° C., about 35° C., about 40° C., about 45° C., about 50° C., about 55° C. or about 60° C. In other instances, an accelerated condition is above 55% RH, about 65% RH, about 70% RH, about 75% RH or about 80% RH. In further instances, an accelerated condition is about 40° C.±2° C. and 60 f 5% RH. In other instances, an accelerated condition is about 40° C.±2° C. and 65 f 5% RH. In yet further instances, an accelerated condition is about 40° C.±2° C. at 75±5% RH. In some cases, an accelerated condition is 40° C.±2° C. and 75±5% RH.

Buffer System in the Desmopressin Oral Liquid Formulations

In some aspects, pharmaceutical compositions of the present disclosure include a buffer system. The buffer system can provide protection from changes in pH ("pH shift") during storage. Buffer systems of the present disclosure can provide a pH of from about 4.0 to about 6.0, about 4.5 to about 5.5, or about 5.0 in the composition. Buffer systems can also be selected and employed at concentrations sufficient to resist a pH change of more than 0.5 pH units over a long term, such as over a period of two years. Buffer systems can maintain pH of desmopressin liquid pharmaceutical compositions described herein and can thereby provide stability of the desmopressin liquid pharmaceutical compositions over a long term, such as over a period of two years.

The buffer system and its concentration can be selected to provide a desired buffer capacity for the composition. Buffer capacity (0) is a unitless parameter that is defined as the number of moles of acid or base that must be added to one liter of the buffer solution (in this case the composition of the present disclosure) to decrease or increase the pH by one unit, and can be expressed by the equation:

$$\beta = n/\Delta pH$$

wherein:

β is buffer capacity;

n is the number of moles of an acid or base added to the composition of the present disclosure per liter of the composition; and ΔpH is the difference between the initial pH of the composition and the pH of the composition after the acid or base is added.

Exemplary calculations for determining buffer capacity for certain liquid pharmaceutical compositions are described in Example D. In some embodiments, the buffer capacity of liquid pharmaceutical compositions according to the present disclosure is at least about 0.001. In some embodiments, the buffer capacity is at least about 0.002. In some embodiments, the buffer capacity is at least about 0.003. In some embodiments, the buffer capacity is at least about 0.004. In some embodiments, the buffer capacity is at least about 0.005. In some embodiments, the buffer capacity is at least about 0.006. In some embodiments, the buffer capacity is at least about 0.007. In some embodiments, the buffer capacity is at least about 0.008. In some embodiments, the buffer capacity is at least about 0.009. In some embodiments, the buffer capacity is at least about 0.01. In some embodiments, the buffer capacity is from about 0.001 to about 0.02. In some embodiments, the buffer capacity is from about 0.001 to about 0.015. In some embodiments, the buffer capacity is from about 0.003 to about 0.015. In some embodiments, the buffer capacity is from about 0.003 to about 0.01. In some embodiments, the buffer capacity is from about 0.003 to about 0.008. In some embodiments, the buffer capacity is from about 0.005 to about 0.008. In some embodiments, the buffer capacity is from about 0.006 to about 0.007. In some embodiments, the buffer capacity is about any of the values listed in Table D. In some embodiments, the buffer capacity falls within a range that is established by any two values as listed in Table D.

The buffer system can comprise two components. The buffer system can comprise three components or more. In some embodiments, the buffer system comprises a weak acid and a conjugate salt thereof. The buffer system can also function as a preservative. The buffer system can be dual-functional. In some embodiments, the buffer system is a two-component, dual-functional, preservative-buffer system. The buffer system, in some cases, does not necessarily have a dual function. In other embodiments, the buffer system does not function as a preservative.

In some embodiments, a liquid pharmaceutical composition described herein comprises a two-component, dual-functional, preservative-buffer system. Employing a two-component, dual-functional, preservative-buffer system, while not required, offers a simple and elegant solution for maintaining good stability of desmopressin oral liquid formulations with a low strength of desmopressin while reducing the unnecessary intake of preservatives by patients. Utilizing the same species for both buffer and preservative, while not required, affords benefits of convenience and reducing the number of ionic species present in the composition. This becomes significant for small dosages of desmopressin, where, due to the low concentration, desmopressin free base or a pharmaceutically acceptable salt thereof (e.g., desmopressin acetate), ionic species can potentially interfere with the stability of the composition. In some embodiments, the two-component, dual-functional, preservative-buffer system comprises two components. In some embodiments, the two components are both dual-functional. In some embodiments, each of the two components is dual-functional. In some embodiments, each of the two components is both a preservative and a buffer system. In some embodiments, only one of the two components is dual-functional. In some embodiments, only one of the two components is both a preservative and a buffer system, thereby providing dual functions to the two-component, dual-functional, preservative-buffer system. In some embodiments, one of the two components is a preservative and the other component is a buffer agent (e.g., a weak acid), thereby providing dual functions to the two-component, dual-functional, preservative-buffer system. In some embodiments, the liquid pharmaceutical composition does not include an additional component for stabilizing or adjusting pH (e.g., an acid, its conjugate base, or a base) that is not within the two-component, dual-functional, preservative-buffer system. In some embodiments, the liquid pharmaceutical composition comprises an additional component for stabilizing or adjusting pH (e.g., an acid, its conjugate base, or a base) that is not within the two-component, dual-functional, preservative-buffer system.

In some embodiments, the two-component, dual-functional, preservative-buffer system comprises an acid. In some embodiments, the two-component, dual-functional, preservative-buffer system comprises a preservative. In some embodiments, the two-component, dual-functional, preservative-buffer system comprises an acidic preservative. In some embodiments, the two-component, dual-functional, preservative-buffer system comprises a conjugate base of the acidic preservative. In some embodiments, the two-component, dual-functional, preservative-buffer system comprises an acidic preservative and a salt of the acidic preservative. In some embodiments, the salt comprises a sodium salt or a potassium salt. In some embodiments, the acidic preservative comprises sorbic acid, benzoic acid, propionic acid, citric acid, acetic acid, lactic acid, formic acid, or ascorbic acid. In some embodiments, the acidic preservative is benzoic acid.

In some embodiments, the two-component, dual-functional, preservative-buffer system is selected from sorbic acid/sorbate, benzoic acid/benzoate, propionic acid/propionate, citric acid/citrate, acetic acid/acetate, lactic acid/lactate, formic acid/formate, and ascorbic acid/ascorbate. In some embodiments, the two-component, dual-functional, preservative-buffer system is sorbic acid/sorbate or benzoic acid/benzoate. In some embodiments, the two-component, dual-functional, preservative-buffer system is benzoic acid and benzoate. In some embodiments, the two-component, dual-functional, preservative-buffer system is benzoic acid and sodium benzoate.

In some embodiments, the two-component, dual-functional, preservative-buffer system is present in an amount of about 5% w/v or less. In some embodiments, the two-component, dual-functional, preservative-buffer system is present in an amount of about 3% w/v or less. In some embodiments, the two-component, dual-functional, preservative-buffer system is present in an amount of about 2% w/v or less. In some embodiments, the two-component, dual-functional, preservative-buffer system is present in an amount of about 1% w/v or less. In some embodiments, the two-component, dual-functional, preservative-buffer system is present in an amount of about 0.9% w/v or less. In some embodiments, the two-component, dual-functional, preservative-buffer system is present in an amount of about 0.8% w/v or less. In some embodiments, the two-component, dual-functional, preservative-buffer system is present in an amount of about 0.7% w/v or less. In some embodiments, the two-component, dual-functional, preservative-buffer system is present in an amount of about 0.6% w/v or less. In some embodiments, the two-component, dual-functional, preservative-buffer system is present in an amount of about 0.5% w/v or less. In some embodiments, the two-component, dual-functional, preservative-buffer system is present in an amount of about 0.4% w/v or less. In some embodiments, the two-component, dual-functional, preservative-buffer system is present in an amount of about 0.32% w/v or less. In some embodiments, the two-component, dual-functional, preservative-buffer system is present in an amount of about 0.3% w/v or less. In some embodiments, the two-component, dual-functional, preservative-buffer system is present in an amount of or about 0.2% w/v or less. In some embodiments, the two-component, dual-functional, preservative-buffer system is benzoic acid and sodium benzoate. In some embodiments, benzoic acid and sodium benzoate are present in an amount of from about 0.005% w/v to about 0.6% w/v. In some embodiments, benzoic acid and sodium benzoate are present in an amount of from about 0.01% w/v to about 0.4% w/v. In some embodiments, benzoic acid and sodium benzoate are present in an amount of from 0.01% w/v to about 0.4% w/v. In some embodiments, benzoic acid and sodium benzoate are present in an amount of from about 0.08% w/v to about 0.32% w/v. In some embodiments, benzoic acid and sodium benzoate are present in an amount of from about 0.1% w/v to about 0.3% w/v. In some embodiments, benzoic acid and sodium benzoate are present in an amount of from about 0.15% w/v to about 0.25% w/v. In some embodiments, benzoic acid and sodium benzoate are present in an amount of from or about 0.16% w/v to about 0.22% w/v.

In some embodiments, the two-component, dual-functional, preservative-buffer system provides a buffering capacity of at least about 0.001. In some embodiments, the two-component, dual-functional, preservative-buffer system provides a buffering capacity of at least about 0.002. In some embodiments, the two-component, dual-functional, preservative-buffer system provides a buffering capacity of at least about 0.003. In some embodiments, the two-component, dual-functional, preservative-buffer system provides a buffering capacity of at least about 0.004. In some embodiments, the two-component, dual-functional, preservative-buffer system provides a buffering capacity of at least about 0.005. In some embodiments, the two-component, dual-functional, preservative-buffer system provides a buffering capacity of at least about 0.006. In some embodiments, the two-component, dual-functional, preservative-buffer system provides a buffering capacity of at least about 0.007. In some embodiments, the two-component, dual-functional, preservative-buffer system provides a buffering capacity of at least about 0.008. In some embodiments, the two-component, dual-functional, preservative-buffer system provides a buffering capacity of at least about 0.009. In some embodiments, the two-component, dual-functional, preservative-buffer system provides a buffering capacity of at least about 0.01. In some embodiments, the two-component, dual-functional, preservative-buffer system provides a buffering capacity from about 0.001 to about 0.02. In some embodiments, the two-component, dual-functional, preservative-buffer system provides a buffering capacity from about 0.001 to about 0.015. In some embodiments, the two-component, dual-functional, preservative-buffer system provides a buffering capacity from about 0.003 to about 0.015. In some embodiments, the two-component, dual-functional, preservative-buffer system provides a buffering capacity from about 0.003 to about 0.01. In some embodiments, the two-component, dual-functional, preservative-buffer system provides a buffering capacity from about 0.003 to about 0.008. In some embodiments, the two-component, dual-functional, preservative-buffer system provides a buffer capacity from about 0.005 to about 0.008. In some embodiments, the two-component, dual-functional, preservative-buffer system provides a buffer capacity from about 0.006 to about 0.007. In some embodiments, the two-component, dual-functional, preservative-buffer system provides a buffering capacity that is about any of the values listed in Table D or that falls within a range that is established by any two values as listed in Table D.

In some embodiments, a liquid pharmaceutical composition described herein comprises a buffer system that also functions as a preservative. The buffer system can be two-components. The buffer system can comprise three components or more. In some embodiments, the buffer system comprises an acid and its conjugate base. In some embodiments, the acid is a weak acid. In some embodiments, the acid is an acidic preservative. In some embodiments, the acidic preservative comprises sorbic acid, benzoic acid, propionic acid, citric acid, acetic acid, lactic acid, formic acid, or ascorbic acid. In some embodiments, the acidic preservative is benzoic acid. In some embodiments, the buffer system comprises sorbic acid, sorbate salts, benzoic acid, benzoate salts, propionic acid, propionate salts, citric acid, citrate salts, acetic acid, acetate salts, lactic acid, lactate salts, formic acid, formate salts, ascorbic acid, ascorbate salts or any combination thereof.

In some embodiments, the two-component, dual-functional, preservative-buffer system comprises an acidic preservative and a salt of the acidic preservative (e.g., a sodium salt or a potassium salt). In some embodiments, the two-component, dual-functional, preservative-buffer system comprises an acidic preservative and a salt of the acidic preservative (e.g., a sodium salt or a potassium salt). In some embodiments, the acidic preservative and the salt of the acidic preservative are in a weight ratio of from about 1:50 to about 50:1. In some embodiments, the acidic preservative and the salt of the acidic preservative are in a weight ratio of from about 1:40 to about 20:1. In some embodiments, the acidic preservative and the salt of the acidic preservative are in a weight ratio of from about 1:30 to about 1:1. In some embodiments, the acidic preservative and the salt of the acidic preservative are in a weight ratio of from about 1:20 to about 1:5. In some embodiments, the acidic preservative and the salt of the acidic preservative are in a weight ratio of from about 1:15 to about 1:1. In some embodiments, the acidic preservative and the salt of the acidic preservative are in a weight ratio of from about 1:15 to about 1:5. In some embodiments, the acidic preservative and the salt of the acidic preservative are in a weight ratio of or from about 1:10 to about 1:1. In some embodiments, the acidic preservative and the salt of the acidic preservative are in a weight ratio of or from about 1:6 to about 1:1. In some embodiments, the acidic preservative and the salt of the acidic preservative are in a weight ratio of or from about 1:5 to about 1:1. In some embodiments, the acidic preservative and the salt of the acidic preservative are in a weight ratio of or from about 1:4 to about 1:1. In some embodiments, the acidic preservative and the salt of the acidic preservative are in a weight ratio of or from about 1:3 to about 1:1. In some embodiments, the acidic preservative and the salt of the acidic preservative are in a weight ratio of or from about 1:2 to about 1:1. In some embodiments, the acidic preservative and the salt of the acidic preservative are in a weight ratio of or from about 1:10 to about 1:3. In some embodiments, the acidic preservative and the salt of the acidic preservative are in a weight ratio of or from about 1:10 to about 1:5. In some embodiments, the acidic preservative and the salt of the acidic preservative are in a weight ratio of or from about 1:10 to about 1:6. In some embodiments, the acidic preservative and the salt of the acidic preservative are in a weight ratio of from about 1:10 to about 1:7. In some embodiments, the acidic preservative and the salt of the acidic preservative are in a weight ratio of from about 1:10 to about 1:8. In some embodiments, the acidic preservative and the salt of the acidic preservative are in a weight ratio of from about 1:9. In some embodiments, the acidic preservative and the salt of the acidic preservative are in a weight ratio of from about 1:8. In some embodiments, the acidic preservative and the salt of the acidic preservative are in a weight ratio of or from about 1:10 to about 1:6. In some embodiments, the acidic preservative and the salt of the acidic preservative are benzoic acid and sodium benzoate.

The buffer system can be weak acids and their conjugate base or salts thereof. In some embodiments, the buffer system does not necessarily have preservative function. In some embodiments, the buffer system comprises two components, three components, or more. In some embodiments, one or more components within the buffer system have preservative function. In some embodiments, one or more components within the buffer system do not have preservative function. In some embodiments, each of the components within the buffer system has preservative function. In some embodiments, none of the components within the buffer system have preservative function. In some embodiments, the buffer system comprises benzoic acid, benzoate, citric acid, citrate, acetic acid, acetate, sorbic acid, sorbate, propionic acid, propionate, carbonate, bicarbonate, glycine/glycine HCl, monobasic/dibasic phosphate, tartaric acid, tartrate, fumaric acid, ascorbic acid, ascorbate, formic acid, formate, phosphoric acid, phosphate, lactic acid, lactate, gluconates, aspartic acid, aspartate, glutamic acid, glutamate, maleic acid, maleate, succinic acid, or succinate, or a combination thereof. In some embodiments, the buffer system does not include malic acid/malate. In some embodiments, the buffer system does not comprise malic acid or malate. In other embodiments, the buffer system comprises malic acid or malate. In other embodiments, the buffer system comprises malic acid or malate and the pharmaceutical composition does not comprise a sweetener.

In some embodiments, the buffer system is present in an amount of about 5% w/v or less. In some embodiments, the buffer system is present in an amount of about 4% w/v or less. In some embodiments, the buffer system is present in an amount of about 3% w/v or less. In some embodiments, the buffer system is present in an amount of about 2% w/v or less. In some embodiments, the buffer system is present in an amount of about 1% w/v or less. In some embodiments, the buffer system is present in an amount of about 0.9% w/v or less. In some embodiments, the buffer system is present in an amount of about 0.8% w/v or less. In some embodiments, the buffer system is present in an amount of about 0.7% w/v or less. In some embodiments, the buffer system is present in an amount of about 0.6% w/v or less. In some embodiments, the buffer system is present in an amount of about 0.5% w/v or less. In some embodiments, the buffer system is present in an amount of about 0.4% w/v or less. In some embodiments, the buffer system is present in an amount of about 0.3% w/v or less. In some embodiments, the buffer system is present in an amount of about 0.32% w/v or less. In some embodiments, the buffer system is present in an amount of or about 0.2% w/v or less.

In some embodiments, the buffer system comprises benzoic acid and sodium benzoate. In some embodiments, the buffer system consists of benzoic acid and sodium benzoate. In some embodiments, benzoic acid and sodium benzoate are present in an amount of from about 0.005% w/v to about 0.6% w/v. In some embodiments, benzoic acid and sodium benzoate are present in an amount of from about 0.01% w/v to about 0.4% w/v. In some embodiments, benzoic acid and sodium benzoate are present in an amount of from about 0.1% w/v to about 0.4% w/v. In some embodiments, benzoic acid and sodium benzoate are present in an amount of from about 0.08% w/v to about 0.32% w/v. In some embodiments, benzoic acid and sodium benzoate are present in an amount of from about 0.1% w/v to about 0.3% w/v. In some embodiments, benzoic acid and sodium benzoate are present in an amount of from about 0.12% w/v to about 0.25% w/v. In some embodiments, benzoic acid and sodium benzoate are present in an amount of from about 0.15% w/v to about 0.22% w/v. In some embodiments, benzoic acid is present in an amount of from about 0.005% w/v to about 0.1% w/v. In some embodiments, benzoic acid is present in an amount of from about 0.008% w/v to about 0.05% w/v. In some embodiments, benzoic acid is present in an amount of from about 0.01% w/v to about 0.04% w/v. In some embodiments, benzoic acid is present in an amount of from about 0.015% w/v to about 0.03% w/v. In some embodiments, benzoic acid is present in an amount of from about 0.015% w/v to about 0.025% w/v. In some embodiments, benzoic acid is present in an amount of from about 0.02% w/v. In some embodiments, sodium benzoate is present in an amount of from about 0.05% w/v to about 0.3% w/v. In some embodiments, sodium benzoate is present in an amount of from about 0.1% w/v to about 0.25% w/v. In some embodiments, sodium benzoate is present in an amount of from about 0.12% w/v to about 0.22% w/v. In some embodiments, sodium benzoate is present in an amount of from about 0.16% w/v to about 0.2% w/v. In some embodiments, sodium benzoate is present in an amount of from about 0.18% w/v to about 0.2% w/v. In some embodiments, sodium benzoate is present in an amount of about 0.19% w/v.

In some embodiments, benzoic acid is present in the pharmaceutical composition of the present disclosure. In some embodiments, benzoic acid is present in an amount of from about 0.001% w/v to about 0.5% w/v. In some embodiments, benzoic acid is present in an amount of from about 0.1% w/v to about 0.5% w/v. In some embodiments, benzoic acid is present in an amount of from about 0.001% w/v to about 0.4% w/v. In some embodiments, benzoic acid is present in an amount of from about 0.005% w/v to about 0.3% w/v. In some embodiments, benzoic acid is present in an amount of from about 0.005% w/v to about 0.2% w/v. In some embodiments, benzoic acid is present in an amount of from about 0.005% w/v to about 0.1% w/v. In some embodiments, benzoic acid is present in an amount of from about 0.005% w/v to about 0.05% w/v. In some embodiments, benzoic acid is present in an amount of from about 0.01% w/v to about 0.05% w/v. In some embodiments, benzoic acid is present in an amount of from about 0.015% w/v to about 0.05% w/v. In some embodiments, benzoic acid is present in an amount of from about 0.015% w/v to about 0.04% w/v. In some embodiments, benzoic acid is present in an amount of from about 0.02% w/v to about 0.04% w/v. In some embodiments, benzoic acid is present in an amount of from about 0.03% w/v to about 0.04% w/v. In some embodiments, benzoic acid is present in an amount of from about 0.035% w/v to about 0.04% w/v. In some embodiments, benzoic acid is present in an amount of from about 0.03% w/v to about 0.035% w/v. In some embodiments, benzoic acid is present in an amount of from about 0.032% w/v to about 0.036% w/v. In some embodiments, benzoic acid is present in an amount of about 0.1% w/v. In some embodiments, benzoic acid is present in an amount of about 0.09% w/v. In some embodiments, benzoic acid is present in an amount of about 0.08% w/v. In some embodiments, benzoic acid is present in an amount of about 0.07% w/v. In some embodiments, benzoic acid is present in an amount of about 0.06% w/v. In some embodiments, benzoic acid is present in an amount of about 0.05% w/v. In some embodiments, benzoic acid is present in an amount of about 0.045% w/v. In some embodiments, benzoic acid is present in an amount of about 0.04% w/v. In some embodiments, benzoic acid is present in an amount of about 0.035% w/v. In some embodiments, benzoic acid is present in an amount of about 0.034% w/v. In some embodiments, benzoic acid is present in an amount of about 0.032% w/v. In some embodiments, benzoic acid is present in an amount of about 0.03% w/v. In some embodiments, benzoic acid is present in an amount of about 0.025% w/v. In some embodiments, benzoic acid is present in an amount of about 0.02% w/v. In some embodiments, benzoic acid is present in an amount of about 0.01% w/v.

In some embodiments, sodium benzoate is present in the pharmaceutical composition of the present disclosure. In some embodiments, sodium benzoate is present in an amount of from about 0.01% w/v to about 1.0% w/v. In some embodiments, sodium benzoate is present in an amount of from about 0.01% w/v to about 0.9% w/v. In some embodiments, sodium benzoate is present in an amount of from about 0.01% w/v to about 0.8% w/v. In some embodiments, sodium benzoate is present in an amount of from about 0.01% w/v to about 0.7% w/v. In some embodiments, sodium benzoate is present in an amount of from about 0.5% w/v to about 1.0% w/v. In some embodiments, sodium benzoate is present in an amount of from about 0.01% w/v to about 0.6% w/v. In some embodiments, sodium benzoate is present in an amount of from about 0.05% w/v to about 0.6% w/v. In some embodiments, sodium benzoate is present in an amount of from about 0.1% w/v to about 0.6% w/v. In some embodiments, sodium benzoate is present in an amount of from about 0.2% w/v to about 0.6% w/v. In some embodiments, sodium benzoate is present in an amount of from about 0.25% w/v to about 0.6% w/v. In some embodiments, sodium benzoate is present in an amount of from about 0.3% w/v to about 0.6% w/v. In some embodiments, sodium benzoate is present in an amount of from about 0.05% w/v to about 0.5% w/v. In some embodiments, sodium benzoate is present in an amount of from about 0.1% w/v to about 0.5% w/v. In some embodiments, sodium benzoate is present in an amount of from about 0.2% w/v to about 0.5% w/v. In some embodiments, sodium benzoate is present in an amount of from about 0.25% w/v to about 0.5% w/v. In some embodiments, sodium benzoate is present in an amount of from about 0.3% w/v to about 0.5% w/v. In some embodiments, sodium benzoate is present in an amount of from about 0.1% w/v to about 0.4% w/v. In some embodiments, sodium benzoate is present in an amount of from about 0.2% w/v to about 0.4% w/v. In some embodiments, sodium benzoate is present in an amount of from about 0.25% w/v to about 0.4% w/v. In some embodiments, sodium benzoate is present in an amount of from about 0.3% w/v to about 0.4% w/v. In some embodiments, sodium benzoate is present in an amount of from about 0.1% w/v to about 0.3% w/v. In some embodiments, sodium benzoate is present in an amount of from about 0.15% w/v to about 0.3% w/v. In some embodiments, sodium benzoate is present in an amount of from about 0.2% w/v to about 0.3% w/v. In some embodiments, sodium benzoate is present in an amount of from about 0.25% w/v to about 0.3% w/v. In some embodiments, sodium benzoate is present in an amount of from about 0.05% w/v to about 0.1% w/v. In some embodiments, sodium benzoate is present in an amount of from about 0.1% w/v to about 0.2% w/v. In some embodiments, sodium benzoate is present in an amount of about 0.1% w/v to about 0.3% w/v. In some embodiments, sodium benzoate is present in an amount of about 0.05% w/v. In some embodiments, sodium benzoate is present in an amount of about 0.1% w/v. In some embodiments, sodium benzoate is present in an amount of about 0.15% w/v. In some embodiments, sodium benzoate is present in an amount of about 0.2% w/v. In some embodiments, sodium benzoate is present in an amount of about 0.25% w/v. In some embodiments, sodium benzoate is present in an amount of about 0.285% w/v. In some embodiments, sodium benzoate is present in an amount of about 0.3% w/v. In some embodiments, sodium benzoate is present in an amount of about 0.35% w/v. In some embodiments, sodium benzoate is present in an amount of about 0.4% w/v. In some embodiments, sodium benzoate is present in an amount of about 0.425% w/v. In some embodiments, sodium benzoate is present in an amount of about 0.45% w/v. In some embodiments, sodium benzoate is present in an amount of about 0.5% w/v. In some embodiments, sodium benzoate is present in an amount of about 0.55% w/v. In some embodiments, sodium benzoate is present in an amount of about 0.6% w/v.

In some embodiments, benzoic acid and sodium benzoate are present in the pharmaceutical composition of the present disclosure. In some embodiments, benzoic acid and sodium benzoate are present in an amount of about 0.6% w/v or less. In some embodiments, benzoic acid and sodium benzoate are present in an amount of from about 0.01% w/v to about 0.6% w/v. In some embodiments, benzoic acid and sodium benzoate are present in an amount of from about 0.05% w/v to about 0.6% w/v. In some embodiments, benzoic acid and sodium benzoate are present in an amount of from about 0.1% w/v to about 0.6% w/v. In some embodiments, benzoic acid and sodium benzoate are present in an amount of from about 0.2% w/v to about 0.6% w/v. In some embodiments, benzoic acid and sodium benzoate are present in an amount of from about 0.3% w/v to about 0.6% w/v. In some embodiments, benzoic acid and sodium benzoate are present in an amount of from about 0.01% w/v to about 0.5% w/v. In some embodiments, benzoic acid and sodium benzoate are present in an amount of from about 0.1% w/v to about 0.5% w/v. In some embodiments, benzoic acid and sodium benzoate are present in an amount of from about 0.2% w/v to about 0.5% w/v. In some embodiments, benzoic acid and sodium benzoate are present in an amount of from about 0.3% w/v to about 0.5% w/v. In some embodiments, benzoic acid and sodium benzoate are present in an amount of from about 0.4% w/v to about 0.5% w/v. In some embodiments, benzoic acid and sodium benzoate are present in an amount of from about 0.05% w/v to about 0.45% w/v. In some embodiments, benzoic acid and sodium benzoate are present in an amount of from about 0.25% w/v to about 0.45% w/v. In some embodiments, benzoic acid and sodium benzoate are present in an amount of from about 0.05% w/v to about 0.4% w/v. In some embodiments, benzoic acid and sodium benzoate are present in an amount of from about 0.08% w/v to about 0.4% w/v In some embodiments, benzoic acid and sodium benzoate are present in an amount of from about 0.1% w/v to about 0.4% w/v. In some embodiments, benzoic acid and sodium benzoate are present in an amount of from about 0.2% w/v to about 0.4% w/v. In some embodiments, benzoic acid and sodium benzoate are present in an amount of from about 0.3% w/v to about 0.4% w/v. In some embodiments, benzoic acid and sodium benzoate are present in an amount of from about 0.1% w/v to about 0.35% w/v. In some embodiments, benzoic acid and sodium benzoate are present in an amount of from about 0.2% w/v to about 0.35% w/v. In some embodiments, benzoic acid and sodium benzoate are present in an amount of from about 0.25% w/v to about 0.35% w/v. In some embodiments, benzoic acid and sodium benzoate are present in an amount of from about 0.3% w/v to about 0.35% w/v. In some embodiments, benzoic acid and sodium benzoate are present in an amount of from about 0.15% w/v to about 0.32% w/v. In some embodiments, benzoic acid and sodium benzoate are present in an amount of from or about 0.18% w/v to about 0.32% w/v. In some embodiments, benzoic acid and sodium benzoate are present in an amount of from or about 0.25% w/v to about 0.32% w/v. In some embodiments, benzoic acid and sodium benzoate are present in an amount of from or about 0.3% w/v to about 0.32% w/v. In some embodiments, benzoic acid and sodium benzoate are present in an amount of from or about 0.18% w/v to about 0.32% w/v. In some embodiments, benzoic acid and sodium benzoate are present in an amount of about 0.32% w/v. In some embodiments, benzoic acid and sodium benzoate are present in an amount of about 0.35% w/v. In some embodiments, benzoic acid and sodium benzoate are present in an amount of about 0.4% w/v. In some embodiments, benzoic acid and sodium benzoate are present in an amount of about 0.45% w/v. In some embodiments, benzoic acid and sodium benzoate are present in an amount of about 0.5% w/v. In some embodiments, benzoic acid and sodium benzoate are present in an amount of about 0.525% w/v. In some embodiments, benzoic acid and sodium benzoate are present in an amount of about 0.55% w/v. In some embodiments, benzoic acid and sodium benzoate are present in an amount of about 0.6% w/v. In some embodiments, the benzoic acid and sodium benzoate provide a pH that is from about 4.0 to about 6.0. In some embodiments, the benzoic acid and sodium benzoate provide a pH that is from about 4.5 to about 5.5. In some embodiments, the benzoic acid and sodium benzoate provide a pH that is from about 4.5 to about 5.0. In some embodiments, the benzoic acid and sodium benzoate provide a pH that is from about 4.7 to about 5.0. In some embodiments, the benzoic acid and sodium benzoate provide a pH of about 4.5. In some embodiments, the benzoic acid and sodium benzoate provide a pH of about 4.7. In some embodiments, the benzoic acid and sodium benzoate provide a pH of about 4.75. In some embodiments, the benzoic acid and sodium benzoate provide a pH of about 4.8. In some embodiments, the benzoic acid and sodium benzoate provide a pH of about 4.9. In some embodiments, the benzoic acid and sodium benzoate provide a pH of about 5.0.

Preservative in the Desmopressin Oral Liquid Formulations

In some embodiments, desmopressin oral liquid formulations described herein comprise a preservative. Preservatives can include anti-microbials, antioxidants, chelating agents, and other agents that enhance sterility, such that a low bioburden is maintained in the formulation of the invention from preparation through storage, and during routine use by patients and clinicians. Exemplary preservatives include ascorbic acid, ascorbyl palmitate, BHA, BHT, citric acid, EDTA and its salts, erythorbic acid, fumaric acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, a preservative used in desmopressin oral liquid pharmaceutical compositions described herein has a dual function. In some embodiments, dual function includes function as preservative and as buffer system (e.g., two-component, dual-functional, preservative-buffer system or a buffer system that also functions as a preservative, as described herein). In some embodiments, utilizing dual functional preservatives that also functions as buffer systems, while not required, affords benefits of convenience and reducing the number of ionic species present in the composition. This becomes significant for small dosages of desmopressin, where, due to the low concentration, desmopressin free base or pharmaceutically acceptable salt thereof, ionic species can potentially interfere with the stability of the composition. In some embodiments, a preservative used in desmopressin oral liquid pharmaceutical compositions described herein does not have a dual function. In some embodiments, desmopressin oral liquid pharmaceutical compositions described herein comprises a dual functional preservative. In some embodiments, desmopressin oral liquid pharmaceutical compositions described herein comprises a preservative that is not dual functional. In some embodiments, desmopressin oral liquid pharmaceutical compositions described herein comprises both a dual functional preservative and a preservative that is not dual functional.

In some embodiments, the preservative comprises an antimicrobial agent, a chelating agent, an antioxidant, or a combination thereof. In some embodiments, the preservative comprises an antimicrobial agent. In some embodiments, the preservative comprises a chelating agent. In some embodiments, the preservative comprises an antioxidant. In some embodiments, the preservative comprises an antimicrobial agent and an antioxidant. In some embodiments, the preservative comprises an antimicrobial agent, a chelating agent, and an antioxidant.

In some embodiments, the preservative comprises benzyl alcohol, benzoic acid, sorbic acid, sodium benzoate, sodium sorbate, EDTA and its salts, parabens (such as methylparaben, ethylparaben, propylparaben, butylparaben and their salts), potassium sorbate, antibacterial agents such as halogenated diphenyl ether (e.g., triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, or any combination thereof. In some embodiments, the preservative comprises benzoic acid, or sodium benzoate, or a combination thereof. In some embodiments, the preservative is present in the liquid pharmaceutical composition in an amount of about 0.01% to about 30% w/v. In some embodiments, the preservative is present in the liquid pharmaceutical composition in an amount of about 0.01% to about 0.1% w/v, about 0.1% to about 0.5% w/v, about 0.5% to about 1% w/v, about 1% to about 5% w/v, about 5% to about 10% w/v, about 10% to about 15% w/v, about 15% to about 20% w/v, about 20% to about 25% w/v, or about 25% to about 30% w/v. In some embodiments, the preservative is present in the liquid pharmaceutical composition in an amount of about 0.05% to about 1% w/v. In some embodiments, the preservative is present in the liquid pharmaceutical composition in an amount of about 0.1% to about 0.5% w/v. In some embodiments, the preservative is present in the liquid pharmaceutical composition in an amount of about 0.2% to about 0.25% w/v. In some embodiments, the preservative is present in the liquid pharmaceutical composition in an amount of about 0.1% w/v. In some embodiments, the preservative is present in the liquid pharmaceutical composition in an amount of about 0.01% w/v.

In some embodiments, the preservative comprises benzoic acid, or sodium benzoate, or a combination thereof. In some embodiments, the preservatives also function as buffer systems. some embodiments, the preservatives are dual functional. In some embodiments, the preservative comprises benzoic acid and sodium benzoate. In some embodiments, the preservative is present in an amount of about 1% w/v or less. In some embodiments, the preservative is present in an amount of about 0.9% w/v or less. In some embodiments, the preservative is present in an amount of about 0.8% w/v or less. In some embodiments, the preservative is present in an amount of about 0.7% w/v or less. In some embodiments, the preservative is present in an amount of about 0.6% w/v or less. In some embodiments, the preservative is present in an amount of about 0.5% w/v or less. In some embodiments, the preservative is present in an amount of about 0.4% w/v or less. In some embodiments, the preservative is present in an amount of about 0.3% w/v or less. In some embodiments, the preservative is present in an amount of about 0.2% w/v or less. In some embodiments, sodium benzoate in an amount of about 0.16% w/v to about 0.2% w/v. In some embodiments, sodium benzoate in an amount of about 0.02% w/v.

In some embodiments, the preservative comprises an antimicrobial agent. In some embodiments, the antimicrobial agent is a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof. In some embodiments, the preservative is a paraben or a mixture of parabens. In some embodiments, the preservative is a paraben or a mixture of parabens. In some embodiments, the preservative is a paraben, such as methyl paraben, ethyl paraben, propyl paraben, or a combination thereof. In some embodiments, the preservative is methyl paraben. In some embodiments, the preservative is propyl paraben. In some embodiments, the preservative is a mixture of methyl paraben and propyl paraben. In some embodiments, an antimicrobial agent is present in the liquid pharmaceutical composition in an amount of about 0.01% to about 10% w/v. In some embodiments, the antimicrobial agent is present in the liquid pharmaceutical composition in an amount of about 0.01% to about 0.1% w/v, about 0.1% to about 0.5% w/v, about 0.5% to about 1% w/v, about 1% to about 5% w/v, or about 5% to about 10% w/v. In some embodiments, the antimicrobial agent is present in the liquid pharmaceutical composition in an amount of about 0.05% to about 1% w/v. In some embodiments, the antimicrobial agent is present in the liquid pharmaceutical composition in an amount of about 0.1% to about 0.5% w/v. In some embodiments, the antimicrobial agent is present in the liquid pharmaceutical composition in an amount of about 0.2% to about 0.25% w/v. In some embodiments, the antimicrobial agent is present in the liquid pharmaceutical composition in an amount of about 0.20% w/v. In some embodiments, the antimicrobial agent is a mixture of methyl paraben and propyl paraben. In some embodiments, the antimicrobial agent is a mixture of parabens or salts thereof.

In some embodiments, the mixture of parabens or salts thereof (e.g., methyl paraben and propyl paraben) is present in the liquid pharmaceutical composition in an amount of about 0.1% w/v to about 1% w/v. In some embodiments, the mixture of parabens or salts thereof (e.g., methyl paraben and propyl paraben) is present in the liquid pharmaceutical composition in an amount of about 0.1% w/v to about 0.15% w/v, about 0.15% w/v to about 0.2% w/v, about 0.2% w/v to about 0.25% w/v, about 0.25% w/v to about 0.3% w/v, about 0.3% w/v to about 0.5% w/v, or about 0.5% w/v to about 1% w/v. In some embodiments, the mixture of parabens is present in an amount of from about 0.01% to about 0.5% w/v. In some embodiments, the mixture of parabens is present in an amount of from about 0.15 to about 0.25% w/v. In some embodiments, the mixture of methyl paraben and propyl paraben is present in the liquid pharmaceutical composition in an amount of about 0.1% w/v to about 0.3% w/v. In some embodiments, the mixture of methyl paraben and propyl paraben is present in the liquid pharmaceutical composition in an amount of about 0.2% w/v. In some embodiments, methyl paraben is present in the liquid pharmaceutical composition in an amount of about 0.05% w/v to about 0.3% w/v. In other embodiments, methyl paraben is present in the liquid pharmaceutical composition in an amount of about 0.05% w/v to about 0.08% w/v, about 0.08% w/v to about 0.15% w/v, about 0.15% w/v to about 0.17% w/v, about 0.17% w/v to about 0.19% w/v, about 0.20% w/v to about 0.25% w/v, or about 0.25% to about 0.3% w/v. In some embodiments, propyl paraben is present in the liquid pharmaceutical composition in an amount of about 0.001% w/v to about 0.05% w/v. In other embodiments, propyl paraben is present in the liquid pharmaceutical composition in an amount of about 0.001% w/v to about 0.005% w/v, about 0.005% w/v to about 0.01% w/v, about 0.01% w/v to about 0.02% w/v, about 0.02% w/v to about 0.03% w/v, or about 0.03% w/v to about 0.05% w/v. In some embodiments, methyl paraben and propyl paraben are present in an amount sufficient to provide antimicrobial effectiveness to the desmopressin oral liquid composition described herein.

In some embodiments, the preservative comprises an antioxidant, for example, vitamin A, monothioglycerol, ascorbic acid, sodium bisulfite, sodium sulfite, α-Tocopherol acetate (vitamin E), butylated hydroxyanisole (BHA), butylated hydroxytoluene (BHT), or a combination thereof. In some embodiments, the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), propyl gallate, vitamin E, hydroquinone, hydroxycoumarins, ethanolamine, lecithin, cephalin, ascorbic acid, sorbitol, phosphoric acid, bisulfite, sodium metabisulfite, thiodipropionic acid and its esters, and dithiocarbamates or a combination thereof. In some embodiments, the antioxidant is butylated hydroxyanisole (BHA). In some embodiments, the antioxidant is butylated hydroxytoluene (BHT). In some embodiments, the antioxidant is butylated hydroxyanisole (BHA) and butylated hydroxytoluene (BHT).

In some embodiments, an antioxidant is present in the liquid pharmaceutical composition in an amount of about 0.001% w/v to about 0.5% w/v. In other embodiments, the antioxidant is present in the liquid pharmaceutical composition in an amount of about 0.001% w/v to about 0.005% w/v, about 0.005% w/v to about 0.007% w/v, about 0.007% w/v to about 0.01% w/v, about 0.01% w/v to about 0.011% w/v, about 0.011% w/v to about 0.015% w/v, about 0.015% w/v to about 0.02% w/v, about 0.02% w/v to about 0.03% w/v, about 0.03% w/v to about 0.05% w/v, about 0.05% w/v to about 0.1% w/v, or about 0.1% w/v to about 0.5% w/v. In some embodiments, the antioxidant is present in the liquid pharmaceutical composition in an amount of about 0.005% w/v to about 0.05% w/v. In some embodiments, the antioxidant is present in the liquid pharmaceutical composition in an amount of about 0.008% w/v to about 0.02% w/v. In some embodiments, the antioxidant is present in the liquid pharmaceutical composition in an amount of about 0.001% w/v to about 0.01% w/v. In some embodiments, the antioxidant is present in the liquid pharmaceutical composition in an amount of about 0.01% w/v. In some embodiments, the antioxidant is BHA. In some embodiments, the antioxidant is BHT.

In some embodiments, BHA or BHT or a combination thereof is present in the liquid pharmaceutical composition in an amount of about 0.001% w/v to about 0.5% w/v. In some embodiments, BHA or BHT or a combination thereof is present in the liquid pharmaceutical composition in an amount of about 0.001% w/v to about 0.005% w/v, about 0.005% w/v to about 0.008% w/v, about 0.008% w/v to about 0.01% w/v, about 0.01% w/v to about 0.015% w/v, about 0.015% w/v to about 0.02% w/v, about 0.02% w/v to about 0.03% w/v, about 0.03% w/v to about 0.05% w/v, about 0.05% w/v to about 0.1% w/v, or about 0.1% to about 0.5% w/v. In some embodiments, BHA or BHT or a combination thereof is present in the liquid pharmaceutical composition in an amount of about 0.005% w/v to about 0.05% w/v. In some embodiments, BHA or BHT or a combination thereof is present in the liquid pharmaceutical composition in an amount of about 0.01% w/v.

In some embodiments, the preservative comprises a chelating agent, such as disodium ethylenediaminetetraacetic acid, polyphosphates, citric acid, calcium disodium edetate, ethylenediaminetetraacetic acid (EDTA), or a combination thereof. In some embodiments, the preservative agent is EDTA. In some embodiments, a chelating agent is present in the liquid pharmaceutical composition in an amount of about 0.001% w/v to about 5% w/v. In other embodiments, the chelating agent is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, the chelating agent is present in the liquid pharmaceutical composition in an amount of about 0.005% w/v to about 0.5% w/v. In some embodiments, the chelating agent is present in the liquid pharmaceutical composition in an amount of about 0.01% w/v to about 0.2% w/v. In some embodiments, the chelating agent is present in the liquid pharmaceutical composition in an amount of about 0.05% w/v to about 0.2% w/v. In some embodiments, the chelating agent is present in the liquid pharmaceutical composition in an amount of about 0.1% w/v. In some embodiments, the chelating agent is EDTA. In some embodiments, EDTA is present in the liquid pharmaceutical composition in an amount of about 0.01% w/v to about 0.2% w/v. In some embodiments, EDTA is present in the liquid pharmaceutical composition in an amount of about 0.05% w/v to about 0.2% w/v. In some embodiments, EDTA is present in the liquid pharmaceutical composition in an amount of about 0.1% w/v.

Liquid Carrier in the Desmopressin Oral Liquid Formulations

In some embodiments, desmopressin oral liquid formulations described herein comprise water and a liquid carrier. In some embodiments, desmopressin oral liquid formulations described herein comprise a liquid carrier. The liquid carrier can be aqueous. The liquid carrier can be non-aqueous. The liquid carrier can include oils (e.g., edible vegetable oils or synthetic edible oils), propylene glycol, glycerin, polypropylene glycol, polyethylene glycol (PEG), alcohol (e.g., ethanol), sugar alcohols, or any combinations thereof. In some embodiments, the liquid carrier comprises polyethers, lower polyhydroxy alcohols, ethanol, propylene glycol, isosorbide dimethyl ether, di(ethylene glycol) ethyl ether, glycols, polyethylene glycols (PEGs), sugar alcohols (e.g., sorbitol and maltitol), or any combinations thereof. In some embodiments, the liquid carrier comprises propylene glycol or glycerin.

In some embodiments, the liquid carrier can include an edible vegetable oil, such as soybean oil, partially hydrogenated soybean oil, corn oil, sunflower oil, or peanut oil. In some instances, liquid carriers are commercially available synthetic edible oils that are equivalent to the vegetable oils. For example, the triglycerides of the $C_8$-$C_{10}$ fatty acids of fractionated coconut oil are available under the trade name of "Miglyol." Specifically, Miglyol is a triglyceride of capric and caprylic acids with glycerol. The oils can also include sugar fatty acids known as "Olestras."

In some embodiments, the liquid carrier comprises polyethers, lower polyhydroxy alcohols, ethanol, propylene glycol, isosorbide dimethyl ether, di(ethylene glycol) ethyl ether, glycols, glycerin, polyethylene glycol (PEG), sugar alcohols, or a combination thereof. In some embodiments, the liquid carrier comprises propylene glycol. In some embodiments, the liquid carrier is glycerin. In some embodiments, the liquid carrier comprises sugar alcohols (e.g., sorbitol). In some embodiments, the liquid carrier is alcohol, such as ethyl alcohol or ethanol. In some embodiments, the liquid carrier is PEG. In some embodiments, the PEG has an average molecular weight of about 200 to about 10,000 g/mol. In some embodiments, the PEG has an average molecular weight of about 200 to about 500 g/mol, about 500 to about 1000 g/mol, about 1000 to about 5000 g/mol, about 5000 to about 10,000 g/mol. In some embodiments, the PEG has an average molecular weight of about 200 to about 500 g/mol. In some embodiments, the PEG has an average molecular weight of about 300 to about 500 g/mol. In some embodiments, the PEG has an average molecular weight of about 350 to about 450 g/mol. In some embodiments, the PEG has an average molecular weight of about 400 g/mol. In some embodiments, the PEG has a number average molecular weight of about 200 to about 10,000 g/mol. In some embodiments, the PEG has a number average molecular weight of about 200 to about 500 g/mol, about 500 to about 1000 g/mol, about 1000 to about 5000 g/mol, about 5000 to about 10,000 g/mol. In some embodiments, the liquid carrier comprises a combination of alcohol (e.g., ethanol) and glycerin. In some embodiments, the liquid carrier comprises a combination of propylene glycol and glycerin. In some embodiments, the liquid carrier comprises a combination of propylene glycol and PEG.

In some embodiments, the liquid carrier is present in a liquid pharmaceutical composition described herein in an amount of about 0.01% w/v to about 0.1% w/v, about 0.1% w/v to about 1% w/v, about 1% w/v to about 5% w/v, about 5% w/v to about 10% w/v, about 10% w/v to about 15% w/v, about 15% w/v to about 20% w/v, about 20% w/v to about 30% w/v, about 30% w/v to about 40% w/v, about 40% w/v to about 50% w/v, about 50% w/v to about 60% w/v, about 60% w/v to about 70% w/v, about 70% w/v to about 80% w/v, about 80% w/v to about 90% w/v. In some embodiments, the liquid carrier is present in the liquid pharmaceutical composition in an amount of about 0.01% w/v to about 90% w/v. In some embodiments, the liquid carrier is present in the liquid pharmaceutical composition in an amount of about 1% w/v to about 80% w/v. In some embodiments, the liquid carrier is present in the liquid pharmaceutical composition in an amount of from about 1% w/v to about 70% w/v. In some embodiments, the liquid carrier is present in the liquid pharmaceutical composition in an amount of from about 1% w/v to about 60% w/v. In some embodiments, the liquid carrier is present in the liquid pharmaceutical composition in an amount of from about 1% w/v to about 50% w/v. In some embodiments, the liquid carrier is present in the liquid pharmaceutical composition in an amount of from about 1% w/v to about 40% w/v. In some embodiments, the liquid carrier is present in the liquid pharmaceutical composition in an amount of from about 1% w/v to about 30% w/v. In some embodiments, the liquid carrier is present in the liquid pharmaceutical composition in an amount of from about 1% w/v to about 20% w/v. In some embodiments, the liquid carrier is present in the liquid pharmaceutical composition in an amount of about 1% w/v to about 2% w/v. In some embodiments, the liquid carrier is present in the liquid pharmaceutical composition in an amount of about 2% w/v to about 3% w/v. In some embodiments, the liquid carrier is present in the liquid pharmaceutical composition in an amount of about 3% w/v to about 4% w/v. In some embodiments, the liquid carrier is present in the liquid pharmaceutical composition in an amount of about 4% w/v to about 5% w/v. In some embodiments, the liquid carrier is present in the liquid pharmaceutical composition in an amount of about 5% w/v to about 6% w/v. In some embodiments, the liquid carrier is present in the liquid pharmaceutical composition in an amount of about 6% w/v to about 7% w/v. In some embodiments, the liquid carrier is present in the liquid pharmaceutical composition in an amount of about 7% w/v to about 8% w/v. In some embodiments, the liquid carrier is present in the liquid pharmaceutical composition in an amount of about 8% w/v to about 9% w/v. In some embodiments, the liquid carrier is present in the liquid pharmaceutical composition in an amount of about 9% w/v to about 10% w/v. In some embodiments, the liquid carrier is present in the liquid pharmaceutical composition in an amount of about 10% w/v to about 15% w/v. In some embodiments, the liquid carrier is present in the liquid pharmaceutical composition in an amount of about 15% w/v to about 20% w/v. In some embodiments, the liquid carrier is present in the liquid pharmaceutical composition in an amount of about 20% w/v to about 25% w/v. In some embodiments, the liquid carrier is present in the liquid pharmaceutical composition in an amount of about 25% w/v to about 30% w/v. In some embodiments, the liquid carrier is present in the liquid pharmaceutical composition in an amount of about 30% w/v to about 35% w/v. In some embodiments, the liquid carrier is present in the liquid pharmaceutical composition in an amount of about 35% w/v to about 40% w/v. In some embodiments, the liquid carrier comprises propylene glycol. In some embodiments, the liquid carrier comprises sugar alcohol, such as sorbitol and maltitol.

In some embodiments, the liquid carrier is present in the liquid pharmaceutical composition in an amount of from about 3% w/v to about 10% w/v. In some embodiments, the liquid carrier is present in the liquid pharmaceutical composition in an amount of from about 3% w/v to about 7% w/v. In some embodiments, the liquid carrier is present in the liquid pharmaceutical composition in an amount of about 5% w/v. In some embodiments, the liquid carrier is present in the liquid pharmaceutical composition in an amount of about 10% w/v. In some embodiments, the liquid carrier is present in the liquid pharmaceutical composition in an amount of about 15% w/v. In some embodiments, the liquid carrier is present in the liquid pharmaceutical composition in an amount of about 20% w/v. In some embodiments, the liquid carrier comprises propylene glycol. In some embodiments, the liquid carrier comprises sugar alcohol, such as sorbitol and maltitol.

In some embodiments, the liquid carrier is propylene glycol. In some embodiments, propylene glycol is present in the liquid pharmaceutical composition in an amount of about 0.1% to about 20% w/v. In some embodiments, propylene glycol is present in the liquid pharmaceutical composition in an amount of about 0.1% to about 1% w/v, about 1% to about 2% w/v, about 2% to about 3% w/v, about 3% to about 4% w/v, about 4% to about 5% w/v, about 5% to about 6% w/v, about 6% to about 7% w/v, about 7% to about 10% w/v, about 10% to about 15% w/v, or about 15% to about 20% w/v. In some embodiments, propylene glycol is present in the liquid pharmaceutical composition in an amount of about 0.5% to about 10% w/v. In some embodiments, propylene glycol is present in an amount of from about 3% w/v to about 10% w/v, from about 3% w/v to about 7% w/v, or about 5% w/v. In some embodiments, propylene glycol is present in an amount of from about 3% w/v to about 10% w/v. In some embodiments, propylene glycol is present in an amount of from about 3% w/v to about 7% w/v. In some embodiments, propylene glycol is present in the liquid pharmaceutical composition in an amount of about 2% to about 8% w/v. In some embodiments, propylene glycol is present in the liquid pharmaceutical composition in an amount of about 4% to about 6% w/v. In some embodiments, propylene glycol is present in the liquid pharmaceutical composition in an amount of about 5% w/v. In some embodiments, propylene glycol is present in an amount of about 10% w/v.

Sweetener and Flavoring Agents in the Desmopressin Oral Liquid Formulations

In some embodiments, desmopressin oral liquid formulations described herein comprise a flavoring agent. The flavoring agent or flavorant can be used to enhance the flavor or aroma of the dose, and to improve general palatability of the dose, thus helping to mask any flavor of the active pharmaceutical ingredient, which patients may find unpleasant. In some embodiments, the amount of desmopressin in the liquid pharmaceutical compositions are so low that most patients do not taste any flavor. The flavoring agent can provide an improved experience for patients, such as in pediatric population, and better compliance with the drug regimen desired by clinicians. Suitable natural or artificial flavors can be selected from pharmaceutically acceptable options as described in standard pharmacy references which are known to those skilled in the art. Suitable natural or synthetic flavoring agents can be selected from standard reference books, such as Remington: The Science and Practice of Pharmacy (2000) and Fenaroli's Handbook of Flavor Ingredients (1994). Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available strawberry, orange, grape, cherry, vanilla, mint and citrus flavors and mixtures thereof. The amount of flavoring may depend on a number of factors, including the organoleptic effect desired. Flavors can present in any amount as desired by those of ordinary skill in the art.

In some embodiments, pharmaceutically acceptable flavors, such as (4-hydroxy-3-methoxybenzaldehyde (vanillin), methyl anthranilate (grape flavor), 3,5-Dimethyl-1,2-Cyclopentadione (caramel flavor), maltol, 4-(4-Hydroxyphenyl)butan-2-one (raspberry flavor), ethyl maltol, ethyl propionate (fruity flavor) and berry flavor, can be used to improve the flavor of desmopressin acetate and other excipients in the formulation, and to enhance palatability and thus compliance in a range of patient populations. Natural and synthetic flavors can be used and adapted to the palate of diverse patient populations, including but not limited to, age- and culturally related flavor preferences (for example bubble gum flavor for pediatric patients). Non-limiting examples of suitable natural flavors, some of which can be readily simulated with synthetic agents or combinations thereof, include almond, anise, apple, apricot, banana, blackberry, blackcurrant, blueberry, caramel, cherry, chocolate, cinnamon, cranberry, grape, lemon, lime, orange, peppermint, pineapple, raspberry, spearmint, strawberry, vanilla, etc. In some embodiments, the flavors include which can be readily simulated with synthetic agents or combinations thereof include fat, poultry, fish, beef, and other meats. In some embodiments, the flavoring agent comprises a natural flavoring agent, an artificial flavoring agent, or a combination thereof. In some embodiments, the flavoring agent comprises 4-hydroxy-3-methoxybenzaldehyde, methyl anthranilate, 3,5-dimethyl-1,2-cyclopentadione, maltol, 4-(4-hydroxyphenyl)butan-2-one, ethyl maltol, or ethyl propionate.

In some embodiments, a suitable amount of flavoring agent is present in liquid pharmaceutical compositions described herein. In some embodiments, a flavoring agent is present in the oral liquid pharmaceutical composition in an amount of about 0.001% w/v to about 5% w/v. In other embodiments, the flavoring agent is present in the liquid pharmaceutical composition in an amount of about 0.001% w/v to about 0.005% w/v, about 0.005% w/v to about 0.01% w/v, about 0.01% w/v to about 0.05% w/v, about 0.05% w/v to about 0.1% w/v, about 0.1% w/v to about 0.5% w/v, about 0.5% w/v to about 1% w/v, about 1% w/v to about 2% w/v, or about 2% w/v to about 5% w/v. In some embodiments, the flavoring agent is present in the liquid pharmaceutical composition in an amount of about 0.005% w/v to about 0.5% w/v. In some embodiments, the flavoring agent is present in the liquid pharmaceutical composition in an amount of about 0.01% w/v to about 0.1% w/v.

In some embodiments, desmopressin oral liquid formulations described herein further comprise a sweetener. Sweeteners or sweetening agents can include any compounds that provide a sweet taste to enhance the palatability of the formulation, including natural and synthetic sugars and natural and synthetic sweeteners (i.e., non-sugar sweetening agents). Sweeteners can include glucose, fructose, sucrose, lactose, maltose or other pharmaceutically acceptable monosaccharides and disaccharides or sugar alcohols, such as xylitol, mannitol, lactitol, maltitol, or sorbitol. Also, sweeteners can include maltodextrin, polydextrose and the like. Other sweeteners can include glycerin, inulin, maltol, salts of acesulfame, alitame, aspartame, neotame, cyclamate salts, sucralose, sorbitol solution, saccharin and its salts, and other artificial and naturally occurring agents providing sweetness either singly or in combination.

Sweeteners illustratively include glucose, fructose, sucrose, maltose, xylitol, tagatose, sucralose, maltitol, isomaltulose, hydrogenated isomaltulose (e.g., sold under the trademark Isomalt™), lactitol, sorbitol, erythritol, trehalose, maltodextrin, polydextrose, and the like. Sweeteners can also include, by way of example and without limitation, aspartame, polyols such as mannitol, sorbitol and xylitol, acesulfame, neotame, stevia, dextrose, saccharin sodium, fructose, high fructose corn syrup, maltodextrin, sucralose, sucrose, and other materials known to one of ordinary skill in the art, and combinations thereof. Other sweeteners illustratively include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweeteners can be used in the form of crude or refined products such as hydrogenated starch hydrolysates, maltitol syrup, high fructose corn syrup, etc., and as branded products, e.g., a combination of propylene glycol, ethyl alcohol, and proprietary artificial flavor sold under the trademark Sweet Am™ liquid by Flavors of North America, a combination of maltodextrin, sorbitol, and fructose sold under the trademark Sweet Am™ powder with Product Code 918.005, a combination of water, propylene glycol, sorbitol, fructose, and proprietary natural and artificial flavor sold under the trademark Sweet Am™ powder with Product Code 918.010 by Flavors of North America, a combination of 1-10% proprietary plant/vegetable extract and 90-99% dextrose sold under the trademark ProSweet™ by Virginia Dare, a maltitol solution sold under the trademark Maltisweet™ by Ingredion, a sorbitol and sorbitol/xylitol solution sold under the trademark Sorbo™ by SPI Polyols, a high fructose corn syrup sold under the trademark Invertose™ by Ingredion, a combination of sucralose and maltodextrin sold under the trademark Rebalance M60 and X60 by Tate and Lyle, and a sugar containing and sugar-free flavored syrups sold under the trademarks Ora-Sweet® and Ora-Sweet-SF®, respectively, by Paddock Laboratories, Inc. Sweeteners can be used singly or in combinations of two or more. Suitable concentrations of different sweetening agents can be selected based on published information, manufacturers' data sheets and by routine testing.

In some embodiments, the sweetener is a sugar (e.g., glucose, fructose, sucrose, lactose, maltose) or sugar alcohol (e.g., xylitol, mannitol, lactitol, maltitol, or sorbitol). In some embodiments, the sweetener comprises glucose, fructose, sucrose, xylitol, tagatose, sucralose, maltitol, isomaltulose, hydrogenated isomaltulose, lactitol, sorbitol, erythritol, trehalose, maltodextrin, or polydextrose. In some embodiments, the sweetener is glucose, fructose, sucrose, xylitol, tagatose, sucralose, maltitol, isomaltulose, hydrogenated isomaltulose, lactitol, sorbitol, erythritol, trehalose, maltodextrin, or polydextrose. In some embodiments, the sweetener is glucose. In some embodiments, the sweetener is sucrose. In some embodiments, the sweetener is sucralose. In some embodiments, the sweetener comprises sorbitol or maltitol, or a combination thereof. In some embodiments, the liquid pharmaceutical compositions do not contain a sweetener.

In some embodiments, a suitable amount of sweetener is present in liquid pharmaceutical compositions described herein. In some embodiments, a sweetener is present in the liquid pharmaceutical composition in an amount of about 0.01% w/v to about 15% w/v. In some embodiments, the sweetener is present in the liquid pharmaceutical composition in an amount of about 0.01% w/v to about 0.05% w/v, about 0.05% w/v to about 0.1% w/v, about 0.1% w/v to about 0.5% w/v, about 0.5% w/v to about 0.7% w/v, about 0.7% w/v to about 1% w/v, about 1% w/v to about 2% w/v, about 2% w/v to about 5% w/v, about 5% w/v to about 10% w/v, or about 10% w/v to about 15% w/v. In some embodiments, the sweetener is present in the liquid pharmaceutical composition in an amount of about 0.1% w/v to about 5% w/v. In some embodiments, the sweetener is present in the liquid pharmaceutical composition in an amount of about 0.5% w/v to about 2% w/v. In other embodiments, a sweetener (e.g., a sugar alcohol) is present in a liquid pharmaceutical composition described herein in an amount of about 0.01% w/v to about 0.1% w/v, about 0.1% w/v to about 1% w/v, about 1% w/v to about 5% w/v, about 5% w/v to about 10% w/v, about 10% w/v to about 15% w/v, about 15% w/v to about 20% w/v, about 20% w/v to about 30% w/v, about 30% w/v to about 40% w/v, about 40% w/v to about 50% w/v, about 50% w/v to about 60% w/v, about 60% w/v to about 70% w/v, about 70% w/v to about 80% w/v, about 80% w/v to about 90% w/v. In some embodiments, a sweetener (e.g., a sugar alcohol) is present in the liquid pharmaceutical composition in an amount of about 0.01% w/v to about 90% w/v. In some embodiments, a sugar alcohol is present in the liquid pharmaceutical composition in an amount of about 1% w/v to about 50% w/v. In some embodiments, a sugar alcohol is present in the liquid pharmaceutical composition in an amount of about 20% w/v to about 70% w/v. In some embodiments, a sweetener (e.g., a sugar alcohol) is present in the liquid pharmaceutical composition in an amount of about 10% w/v to about 90% w/v. In other embodiments, the liquid pharmaceutical composition does not comprise a sweetener.

Additional Excipients

In further embodiments, a desmopressin oral liquid formulation described herein comprises additional excipients including, but not limited to coloring agents and thickeners. Additional excipients such as bulking agents and tonicity agents are within the scope of the embodiments.

In further embodiments, the desmopressin oral liquid formulation comprises a coloring agent for identity and/or aesthetic purposes. Coloring agents or colorants are pigments and/or dyes or a combination thereof, that are used to impart color to the composition. In some embodiments, colorants include, but are not limited to, FD&C approved colorants. Examples include caramel colorant, red colorant Enocianin, Indigo yellow, Quinoline yellow, Quinizarine Green, FD&C Blue #1 Aluminum Lake, FD&C Blue #2, other FD&C Blue colors, titanium dioxide, iron oxide, and/or combinations thereof. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof.

Thickeners impart viscosity or weight to the resultant liquid forms from desmopressin oral liquid formulations described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose and certain gums (xanthan gum, locust bean gum, etc.). In certain embodiments, the desmopressin oral liquid formulation comprises a thickener.

Additional excipients are contemplated in the desmopressin oral liquid formulation embodiments. These additional excipients are selected based on function and compatibility with the desmopressin oral liquid formulations described herein and may be found, for example in Remington: The Science and Practice of Pharmacy, Nineteenth Ed (Easton, PA: Mack Publishing Company, 1995); Hoover, John E., Remington's Pharmaceutical Sciences, (Easton, PA: Mack Publishing Co 1975); Liberman, H. A. and Lachman, L., Eds., Pharmaceutical Dosage Forms (New York, NY: Marcel Decker 1980); and Pharmaceutical Dosage Forms and Drug Delivery Systems, Seventh Ed (Lippincott Williams & Wilkins 1999), herein incorporated by reference in their entirety.

Direct Dosing Device

Provided herein, in one aspect, is a direct dosing device comprising liquid pharmaceutical compositions described herein.

As used herein, the term "direct dosing device" refers to a device or container that is used to administer, adapted to administer, or configured to administer its contents directly to a patient via oral administration. In some embodiments, the direct dosing device is a measuring device. In some embodiments, the direct dosing device is a measuring device with graduations. In some embodiments, the graduations are in mL (e.g., 1 mL, 0.5 mL, or 0.1 mL). In some embodiments, the direct dosing device is an oral syringe. In some embodiments, the oral syringe has 1 mL, 0.5 mL, 0.1 mL, 0.05 mL, or 0.01 mL graduated marks. In some embodiments, the oral syringe has 0.1 mL graduated marks. The direct dosing device can be used to administer desmopressin acetate oral liquid pharmaceutical compositions described herein to a subject in need thereof.

Examples of such direct dosing devices include, but are not limited to, syringes, for example oral syringes, cups for example dosing cups, an ampoule, a vial, spoons for example dosage spoons, teaspoons and tablespoons, a dropper or dropper assembly, a pipette, a measuring device with graduations, or any device customarily used for, or capable of being used to dispense a liquid medicament to a patient for oral administration. Such devices, including dosage cups, dosage spoons, droppers and dropper assemblies, oral syringes, bottles with fitments, and total dispensing systems are sold by several companies, including for example Comar, Voorhees, NJ. Examples of the foregoing dosage cups, dosage spoons, droppers and dropper assemblies, oral syringes, and total dispensing systems can be found on the Comar website at www.comar.com., the O.Berk website at www.oberk.com, and the Drug Plastic website at www.drugplastics.com.

In some embodiments, the oral syringe comprises a simple piston pump with a plunger. In some embodiments, the plunger fits tightly in one end of a cylindrical tube (the barrel) and can be pushed or pulled along inside the barrel to create negative or positive relative pressure within the barrel that causes the syringe to take in or expel a liquid or gas through an orifice (nozzle) at the opposing end of the barrel. In some embodiments, the barrel of an oral syringe is made of plastic and is at least partially transparent along its length with graduated markings to indicate the volume of fluid in the syringe based on the position of the plunger visible within the barrel. Suitable oral syringes can come in a wide range of sizes and with some variation in configuration. Oral syringes can be marked in units of milliliters and come in sizes ranging from 0.5 to 60 milliliters. An annular flange partially or fully encircling the outside surface of the barrel can be provided to facilitate compression of the plunger into the barrel. In some embodiments, the plunger is plastic as this provides a good seal within the barrel and is inexpensive to produce so as to be disposable. In some embodiments, the use of oral syringe to administer liquid pharmaceutical compositions described herein that are ready-to-use without dilution or addition of any further components to the liquid pharmaceutical composition provides increased dosing accuracy and reduced risk of microbial contamination of the liquid pharmaceutical composition during the administration.

In some embodiments, a direct dosing device described herein contains a desired amount of a liquid pharmaceutical composition described herein for direct administration to a subject via oral administration. In some embodiments, the direct dosing device is an oral syringe, e.g., an oral syringe having with incremental markings to indicate liquid volume in the syringe. In some embodiments, the direct dosing device is a dropper, e.g., a dropper with incremental markings to indicate liquid volume in the dropper. In some embodiments, the direct dosing device is a pipette. In some embodiments, the direct dosing device is a measuring device with incremental markings to indicate liquid volume in the device. In some embodiments, the direct dosing device is a device customarily used for orally dispensing an oral liquid pharmaceutical composition to a subject. In some embodiments, the direct dosing device is a device that is configured adapted to administer, or configured to administer an oral liquid pharmaceutical composition. In some embodiments, the direct dosing device contains from 0.005 mg to 1.2 mg of desmopressin free base or a pharmaceutically acceptable salt thereof (e.g., desmopressin acetate). In some embodiments, the direct dosing device contains from 0.005 mg to 0.10 mg of desmopressin free base or a pharmaceutically acceptable salt thereof (e.g., desmopressin acetate). In some embodiments, the direct dosing device contains from 0.005 mg to 0.050 mg of desmopressin free base or a pharmaceutically acceptable salt thereof (e.g., desmopressin acetate).

In some embodiments, the direct dosing device is a syringe, for example an oral syringe, containing a desired amount of the desmopressin oral liquid pharmaceutical compositions described herein. The syringe can be preloaded with a desired amount of desmopressin oral liquid pharmaceutical compositions described herein, for example a dose of the desmopressin composition to be administered to the patient, or can be filled with a desired amount of desmopressin oral liquid pharmaceutical compositions described herein, for example a dose of the desmopressin composition to be administered to the subject, at the point of administration by, for example, withdrawal of the desired amount of desmopressin from a liquid pharmaceutical composition as described herein. In some embodiments, the administration does not involve dilution or addition of any further components to the desmopressin oral liquid pharmaceutical compositions.

Methods of Treatment or Administration

Provided herein, in one aspect, are methods of treating a disease or condition, or symptoms thereof comprising administration of desmopressin oral liquid compositions described herein to a subject in need thereof. In some embodiments, the liquid pharmaceutical composition is administered to the subject orally. In some embodiments, the liquid pharmaceutical composition is administered to the subject via a direct dosing device as described herein, such as an oral syringe. In some embodiments, the liquid pharmaceutical composition is administered to the subject in a therapeutically effective amount. In some embodiments, the desmopressin oral liquid composition is administered to the subject through a nasogastric tube. In some embodiments, the liquid pharmaceutical composition is administered to the subject through jejunostomy tube. In some embodiments, the liquid pharmaceutical composition is administered to the subject through gastrostomy tube.

Desmopressin oral liquid compositions described herein can treat a disease or condition, or symptoms thereof in a subject in need thereof. In some embodiments, the disease or condition, or symptoms thereof is selected from diabetes insipidus, bedwetting, hemophilia A, von willebrand disease, polyurea, and high blood urea levels. In some embodiments, the disease or condition, or symptoms thereof is selected from central diabetes insipidus, primary nocturnal enuresis, nocturia, polydipsia, nocturnal polyuria, hypothalamic injury-induced obesity (HIO), bleeding in subjects with Hemophilia A and/or with von Willebrand-Jürgens disease, and postoperative bleeding. In some embodiments, the disease or condition, or symptoms thereof is central diabetes insipidus. In some embodiments, the disease or condition, or symptoms thereof is primary nocturnal enuresis. In some embodiments, the disease or condition, or symptoms thereof is nocturia. In some embodiments, the disease or condition, or symptoms thereof is polydipsia. In some embodiments, the disease or condition, or symptoms thereof is nocturnal polyuria. In some embodiments, the disease or condition, or symptoms thereof is bleeding in subjects. In some embodiments, the bleeding in subjects comprises bleeding in subjects with Hemophilia A. In some embodiments, the bleeding in subjects comprises bleeding in subjects with von Willebrand-Jurgens disease. In some embodiments, the bleeding in subjects comprises postoperative bleeding.

In some instances, the subject is an adult. In some instances, the subject has an age of more than 18 years old. In some instances, the subject is within a pediatric population. In some instances, the subject has an age of not more than 18 years old. In some instances, the subject has an age of not more than 17 years old. In some instances, the subject has an age of not less than 3 years old. In some instances, the subject has an age of not less than 4 years old. In some instances, the subject has an age of not less than 4 years old and not more than 18 years old. In some embodiments, the term "adult" refers to a human of age 17 or older. In some embodiments, the term "adult" refers a human of age 18 or older. In some embodiments, the term "pediatric" when used to describe a human subject, indicates that the human subject is from 2-17 years old. In some embodiments, the term "pediatric" when used to describe a human subject, indicates that the human subject is from 2-16 years old.

In some embodiments, administration of a liquid pharmaceutical composition described herein to the subject is made via a direct dosing device described herein. In some embodiments, administration of a liquid pharmaceutical composition described herein to the subject does not involve dilution. In some embodiments, administration of a liquid pharmaceutical composition described herein to the subject does not involve addition of any further components to the liquid pharmaceutical composition. In some embodiments, administration of a liquid pharmaceutical composition described herein to the subject does not involve dilution and does not involve addition of any further components to the liquid pharmaceutical composition.

In certain therapeutic applications, the desmopressin oral liquid formulations are administered to a patient already suffering from a disease, e.g., diabetes insipidus, primary nocturnal enuresis, or polyurea, in an amount sufficient to cure the disease or at least partially arrest or ameliorate the symptoms, e.g., increase blood pressure, blood sugar, or appetite. Amounts effective for this use depend on the severity of the disease, previous therapy, the patient's health status, weight, and response to the desmopressin oral liquid formulations, and the judgment of the treating physician. In some embodiments, the liquid pharmaceutical compositions are administered in a therapeutically effective amount.

Therapeutically effective amounts for each use described herein can optionally be determined by methods including, but not limited to, a dose escalation clinical trial. The precise therapeutically effective amounts for each use described herein can also depend on the patient's state of health, weight, and the like. When used in a patient, the therapeutically effective amounts for each use described herein can depend on the risk or susceptibility of developing the particular disease, previous therapy, the patient's health status and response to the desmopressin acetate formulations, and the judgment of the treating physician.

In certain embodiments wherein the patient's condition does not improve, upon the doctor's discretion the administration of a desmopressin oral liquid composition described herein are administered chronically, that is, for an extended period of time, including throughout the duration of the patient's life, if needed, in order to ameliorate or otherwise control or limit the symptoms of the patient's disease. In other embodiments, administration of a desmopressin oral liquid composition continues until complete or partial response of a disease.

In certain embodiments wherein a patient's status does improve, the dose of a desmopressin oral liquid composition being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, desmopressin oral liquid compositions described herein are administered chronically. For example, in some embodiments, a desmopressin oral liquid composition is administered as a continuous dose, i.e., administered daily to a subject. In some other embodiments, desmopressin oral liquid compositions described herein are administered intermittently (e.g., drug holiday that includes a period of time in which the formulation is not administered or is administered in a reduced amount).

In some embodiments a desmopressin oral liquid composition is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, a desmopressin oral liquid composition is administered orally to a subject who is in a fasted state for at least 8 hours. In other embodiments, a desmopressin oral liquid composition is administered to a subject who is in a fasted state for at least 10 hours. In yet other embodiments, a desmopressin oral liquid composition is administered to a subject who is in a fasted state for at least 12 hours. In other embodiments, a desmopressin oral liquid composition is administered to a subject who has fasted overnight.

In other embodiments a desmopressin oral liquid composition is administered to a subject who is in a fed state. A fed state refers to a subject who has taken food or has had a meal. In certain embodiments, a desmopressin oral liquid composition is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1-hour post-meal, or 2 hours post-meal. In certain instances, a desmopressin oral liquid composition is administered to a subject in a fed state 30 minutes post-meal. In other instances, a desmopressin oral liquid composition is administered to a subject in a fed state 1-hour post-meal. In yet further embodiments, a desmopressin oral liquid composition is administered to a subject with food.

In further embodiments described herein, a desmopressin oral liquid composition is administered at a certain time of day for the entire administration period. For example, a desmopressin oral liquid composition can be administered at a certain time in the morning, in the evening, or prior to bed. In certain instances, a desmopressin oral liquid composition is administered in the morning. In other embodiments, a desmopressin oral liquid composition can be administered at different times of the day for the entire administration period. For example, a desmopressin oral liquid composition can be administered on 8:00 am in the morning for the first day, 12 pm noon for the next day or administration, 4 pm in the afternoon for the third day or administration, and so on.

In some embodiments, the method of treating a disease or disorder, or a symptom thereof comprises orally administering to a subject in need thereof desmopressin oral liquid pharmaceutical compositions described herein. In some embodiments, the disease or disorder, or symptom thereof is one described herein. In some embodiments, the disease or disorder, or symptom thereof is selected from: from diabetes insipidus, bedwetting, hemophilia A, von willebrand disease and high blood urea levels. In some embodiments, the method comprises orally administering to a subject in need thereof desmopressin oral liquid pharmaceutical compositions described herein, wherein the desmopressin oral liquid pharmaceutical compositions are administered to the subject from a direct dosing device described herein. In some embodiments, the direct dosing device is an oral syringe or a dropper. In some embodiments, the desmopressin oral liquid pharmaceutical compositions described herein is administered to the subject without dilution. In some embodiments, the subject a pediatric subject. In some embodiments, the subject is from 2-9 years old. In some embodiments, the subject is at least 10 years old. In some embodiments, the subject is from 2-16 years old. In some embodiments, the subject is an adult. In some embodiments, the method further comprises the step of filling the direct dosing device with desmopressin oral liquid pharmaceutical compositions described herein. In some embodiments, the amount of the pharmaceutical composition administered to the subject is sufficient to provide from 0.005 mg to 0.20 mg of desmopressin free base or a pharmaceutically acceptable salt thereof (e.g., desmopressin acetate) to the subject.

Also provided herein, in one aspect, are methods for administering desmopressin free base or a pharmaceutically acceptable salt thereof to a subject in need thereof, comprising orally administering a liquid pharmaceutical composition described herein. In some embodiments, the method comprises orally administering the liquid pharmaceutical composition without dilution. In some embodiments, the method comprises orally administering the liquid pharmaceutical composition without addition of any further components to the liquid pharmaceutical composition. In some embodiments, the method comprises orally administering the liquid pharmaceutical composition without dilution or addition of any further components to the liquid pharmaceutical composition. In some embodiments, administration of the liquid pharmaceutical composition to a subject in need thereof is made via a direct dosing device described herein, such as an oral syringe with graduated marks. In some cases, the method comprises a reduced risk of microbial contamination as compared to a method of orally administering a desmopressin composition that involves dilution and/or addition of any further components to such desmopressin composition prior to administration to the subject. In some cases, the method comprises an increased accuracy of dosing as compared to a method of orally administering a desmopressin composition that involves dilution and/or addition of any further components to such desmopressin composition prior to administration to the subject. In some embodiments, the desmopressin composition that involves dilution and/or addition of any further components requires one or more of dilution of the composition, dissolution of a solid (e.g., a crushed tablet; a crushed tablet comprising desmopressin), or suspension of a solid (e.g., a crushed tablet; a crushed tablet comprising desmopressin) prior to administration to the subject.

In some embodiments, the method for administering desmopressin free base or a pharmaceutically acceptable salt thereof, to a subject in need thereof, comprising orally ingesting desmopressin oral liquid pharmaceutical composition described herein. In some embodiments, desmopressin oral liquid pharmaceutical compositions are administered to the subject from a direct dosing device described herein. In some embodiments, the direct dosing device is an oral syringe or a dropper. In some embodiments, the desmopressin oral liquid pharmaceutical compositions described herein is administered to the subject without dilution. In some embodiments, the subject a pediatric subject. In some embodiments, the subject is from 2-9 years old. In some embodiments, the subject is at least 10 years old. In some embodiments, the subject is from 2-16 years old. In some embodiments, the subject is an adult. In some embodiments, the method further comprises the step of filling the direct dosing device with desmopressin oral liquid pharmaceutical compositions described herein. In some embodiments, the amount of the pharmaceutical composition administered to the subject is sufficient to provide from 0.005 mg to 0.20 mg of desmopressin free base or a pharmaceutically acceptable salt thereof (e.g., desmopressin acetate) to the subject. In some embodiments, the method for administering desmopressin free base or a pharmaceutically acceptable salt thereof (e.g., desmopressin acetate) comprises administering a desmopressin oral liquid pharmaceutical formulation described herein to a subject from a direct dosing device, e.g., an oral syringe with incremental markings to indicate liquid volume added or dispensed.

In some embodiments, the method for administering desmopressin free base or a pharmaceutically acceptable salt thereof comprises reducing risk of microbial contamination of a pharmaceutical composition comprising desmopressin free base or a pharmaceutically acceptable salt thereof (e.g., desmopressin acetate); and/or increasing the accuracy of dosing, in the administration of desmopressin free base or a pharmaceutically acceptable salt thereof (e.g., desmopressin acetate) to a patient. In some embodiments, the method comprising one more of: a) preparing a desmopressin oral liquid pharmaceutical composition described herein; and/or b) placing the composition from (a) in a direct dosing device described herein; and/or c) administering to a patient in need thereof of a liquid pharmaceutical composition described herein.

The present disclosure also provides the use of a composition as described herein in the preparation of a medicament for the treatment of any of the disease or disorders, or symptom thereof, as disclosed herein.

Dosing

In one aspect, desmopressin oral liquid compositions described herein are used for the treatment of diseases and conditions described herein. In addition, a method for treating any of the diseases or conditions described herein in a subject in need of such treatment, involves administration of desmopressin oral liquid compositions in therapeutically effective amounts to said subject.

Dosages of desmopressin oral liquid compositions described can be determined by any suitable method. In various embodiments, a patient in need of desmopressin acetate is monitored for improvement of symptoms, and the dose is individually adjusted to their optimum therapeutic dose. Maximum tolerated doses (MTD) and maximum response doses (MRD) for desmopressin acetate can be determined via established animal and human experimental protocols as well as in the examples described herein. For example, toxicity and therapeutic efficacy of desmopressin acetate can be determined by standard pharmaceutical procedures in cell cultures or experimental animals, including, but not limited to, for determining the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Desmopressin acetate dosages exhibiting high therapeutic indices are of interest. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given desmopressin oral liquid composition that corresponds to such an amount varies depending upon factors such as the particular desmopressin acetate salt or form, disease condition and its severity, the identity (e.g., weight, sex) of the subject or host in need of treatment, but can nevertheless be determined according to the particular circumstances surrounding the case, including, e.g., the specific agent being administered, the liquid composition type, the condition being treated, and the subject or host being treated. In many instances, the dose of the desmopressin oral liquid compositions can be adjusted based on any change or lack thereof of the symptoms in a patient, such as an improvement, no change or effect, or deterioration of a symptom or a condition. In some instances, the desmopressin oral liquid compositions can be discontinued if there is a lack of satisfactory response is noted.

In some embodiments, desmopressin oral liquid compositions described herein are provided in a dose per day from about 0.005 mg to 5 mg, from about 0.005 mg to about 2 mg, from about 0.005 mg to about 1.2 mg, from about 0.01 mg to about 1.2 mg, from about 0.05 mg to about 1.2 mg, from about 0.05 mg to about 1 mg, from about 0.05 mg to about 0.5 mg, from about 0.05 mg to about 0.1 mg, from about 0.01 mg to about 0.05 mg, from about 0.05 mg to about 0.1 mg, from about 0.01 mg to about 0.2 mg, or from about 0.2 mg to about 0.5 mg of desmopressin acetate. In certain embodiments, the desmopressin oral liquid compositions described herein are provided in a daily dose of about 0.005 mg to about 0.01 mg, about 0.01 mg to about 0.02 mg, about 0.02 mg to about 0.05 mg, about 0.05 mg to about 0.1 mg, about 0.1 mg to about 0.25 mg, about 0.25 mg to about 0.5 mg, about 0.5 mg to about 1 mg, about 1 mg to about 1.2 mg, about 1.2 mg to about 2 mg, about 2 mg to about 3 mg, about 3 mg to about 5 mg. In certain instances, the desmopressin oral liquid compositions described herein are provided in a dose per day of about 0.005 to about 0.01 mg. In certain instances, the desmopressin oral liquid compositions described herein are provided in a dose per day of about 0.01 to about 0.03 mg. In certain instances, the desmopressin oral liquid compositions described herein are provided in a dose per day of about 0.02 to about 0.05 mg. In certain instances, the desmopressin oral liquid compositions described herein are provided in a dose per day of about 0.05 to about 0.08 mg. In certain instances, the desmopressin oral liquid compositions described herein are provided in a dose per day of about 0.08 to about 0.1 mg. In certain instances, the desmopressin oral liquid compositions described herein are provided in a dose per day of about 0.1 to about 0.5 mg. In certain instances, the desmopressin oral liquid compositions described herein are provided in a dose per day of about 0.5 to about 1.2 mg. In certain instances, the desmopressin oral liquid compositions described herein are provided in a dose per day of about 1 to about 5 mg. In certain instances, the desmopressin oral liquid compositions described herein are provided in a dose per day of about 0.005 mg. In certain instances, the desmopressin oral liquid compositions described herein are provided in a dose per day of about 0.01 mg. In certain instances, the desmopressin oral liquid compositions described herein are provided in a dose per day of about 0.02 mg. In certain instances, the desmopressin oral liquid compositions described herein are provided in a dose per day of about 0.025 mg. In certain instances, the desmopressin oral liquid compositions described herein are provided in a dose per day of about 0.03 mg. In certain instances, the desmopressin oral liquid compositions described herein are provided in a dose per day of about 0.04 mg. In certain instances, the desmopressin oral liquid compositions described herein are provided in a dose per day of about 0.05 mg. In certain instances, the desmopressin oral liquid compositions described herein are provided in a dose per day of about 0.06 mg. In certain instances, the desmopressin oral liquid compositions described herein are provided in a dose per day of about 0.07 mg. In certain instances, the desmopressin oral liquid compositions described herein are provided in a dose per day of about 0.08 mg. In certain instances, the desmopressin oral liquid compositions described herein are provided in a dose per day of about 0.09 mg. In certain instances, the desmopressin oral liquid compositions described herein are provided in a dose per day of about 0.1 mg. In certain instances, the desmopressin oral liquid compositions described herein are provided in a dose per day of about 0.15 mg. In certain instances, the desmopressin oral liquid compositions described herein are provided in a dose per day of about 0.2 mg. In certain instances, the desmopressin oral liquid compositions described herein are provided in a dose per day of about 0.3 mg. In certain instances, the desmopressin oral liquid compositions described herein are provided in a dose per day of about 0.4 mg. In certain instances, the desmopressin oral liquid compositions described herein are provided in a dose per day of about 0.5 mg. In certain instances, the desmopressin oral liquid compositions described herein are provided in a dose per day of about 0.6 mg. In certain instances, the desmopressin oral liquid compositions described herein are provided in a dose per day of about 0.7 mg. In certain instances, the desmopressin oral liquid compositions described herein are provided in a dose per day of about 0.8 mg. In certain instances, the desmopressin oral liquid compositions described herein are provided in a dose per day of about 0.9 mg. In certain instances, the desmopressin oral liquid compositions described herein are provided in a dose per day of about 1 mg. In certain instances, the desmopressin oral liquid compositions described herein are provided in a dose per day of about 1.2 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the desmopressin oral liquid compositions described herein are from about 0.01 ug/kg to about 100 ug/kg, from about 0.1 ug/kg to about 10 ug/kg, from about 0.25 ug/kg to about 5 ug/kg, from about 0.3 ug/kg to about 3 ug/kg, from about 0.5 ug/kg to about 1 ug/kg per body weight. In one embodiment, the daily dosages appropriate for the desmopressin oral liquid compositions are from about 0.02 ug/kg to about 0.05 ug/kg desmopressin acetate per body weight. In another embodiment, the daily dosage appropriate for the desmopressin oral liquid compositions are from about 0.03 ug/kg to about 0.08 ug/kg per body weight. In another embodiment, the daily dosage appropriate for the desmopressin oral liquid compositions are from about 0.05 ug/kg to about 0.5 ug/kg per body weight. In some embodiment, the daily dosage appropriate for the desmopressin oral liquid compositions is about 0.05 ug/kg, about 0.06 ug/kg, about 0.07 ug/kg, about 0.08 ug/kg, about 0.10 ug/kg, about 0.15 ug/kg, about 0.20 ug/kg, about 0.30 ug/kg, about 0.40 ug/kg, about 0.50 ug/kg, about 0.60 ug/kg, about 0.70 ug/kg, about 0.80 ug/kg, about 0.90 ug/kg, or about 1 ug/kg. In some embodiment, the daily dosage appropriate for the desmopressin oral liquid compositions is from about 2 ug/kg to about 10 ug/kg, from about 5 ug/kg to about 20 ug/kg, from about 10 ug/kg to about 50 ug/kg. In another embodiment, the daily dosage appropriate for the desmopressin oral liquid compositions is about 0.005 ug/kg, about 0.006 ug/kg, about 0.007 ug/kg, about 0.008 ug/kg, about 0.010 ug/kg, about 0.015 ug/kg, about 0.020 ug/kg.

In other embodiments the desmopressin oral liquid compositions are provided at the maximum tolerated dose (MTD) for desmopressin acetate or a pharmaceutically acceptable salt thereof. In other embodiments, the amount of the desmopressin oral liquid compositions administered is from about 10% to about 90% of the maximum tolerated dose (MTD), from about 25% to about 75% of the MTD, or about 50% of the MTD. In particular embodiments, the amount of the desmopressin oral liquid compositions administered is from about 5% to about 10%, about 10% to about 20%, about 20% to about 30%, about 30% to about 40%, about 40% to about 50%, about 50% to about 60%, about 60% to about 70%, about 70% to about 80%, about 80% to about 90%, about 90% to about 99% or higher, of the MTD for desmopressin acetate or a pharmaceutically acceptable salt thereof.

In some embodiments, the desmopressin oral liquid compositions are administered to a subject with an amount of desmopressin acetate to be 90%-110% relative to a dose required for delivering a therapeutically relevant exposure of desmopressin acetate using a desmopressin acetate oral tablet formulation. In some embodiments, the subject is in the fasted state when administered the desmopressin oral liquid compositions or the desmopressin acetate oral tablet formulation. In some embodiments, the desmopressin acetate oral tablet formulation is sold under the trade name DDAVP. In some embodiments, the desmopressin oral liquid compositions are administered to a subject with an amount of desmopressin acetate to be 95%-105% relative to a dose required for delivering a therapeutically relevant exposure of desmopressin acetate using a desmopressin acetate oral tablet formulation. In some embodiments, the desmopressin oral liquid compositions are administered to a subject with an amount of desmopressin acetate to be 98%-102% relative to a dose required for delivering a therapeutically relevant exposure of desmopressin acetate using a desmopressin acetate oral tablet formulation. In some embodiments, the desmopressin oral liquid compositions are administered to a subject with an amount of desmopressin acetate to 100% relative to a dose required for delivering a therapeutically relevant exposure of desmopressin acetate using a desmopressin acetate oral tablet formulation.

In some embodiments, the desmopressin oral liquid compositions are provided in a dosage that is lower than a dosage of a known desmopressin acetate tablet formulation (e.g., 0.1 mg or 0.2 mg). In some embodiments, the desmopressin oral liquid compositions are provided in a dosage that is at least 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 25 times, 30 times, 35 times, or 40 times lower than a dosage of a known desmopressin acetate tablet formulation (e.g., 0.1 mg or 0.2 mg). In some embodiments, the desmopressin oral liquid compositions are provided in a dosage that is at least 2 times lower than a dosage of a known desmopressin acetate tablet (e.g., 0.1 mg). In some embodiments, the desmopressin oral liquid compositions are provided in a dosage that is at least 3 times lower than a dosage of a known desmopressin acetate tablet (e.g., 0.1 mg). In some embodiments, the desmopressin oral liquid compositions are provided in a dosage that is at least 4 times lower than a dosage of a known desmopressin acetate tablet (e.g., 0.1 mg). In some embodiments, the desmopressin oral liquid compositions are provided in a dosage that is at least 5 times lower than a dosage of a known desmopressin acetate tablet (e.g., 0.1 mg). In some embodiments, the desmopressin oral liquid compositions are provided in a dosage that is at least 6 times lower than a dosage of a known desmopressin acetate tablet (e.g., 0.1 mg). In some embodiments, the desmopressin oral liquid compositions are provided in a dosage that is at least 7 times lower than a dosage of a known desmopressin acetate tablet (e.g., 0.1 mg). In some embodiments, the desmopressin oral liquid compositions are provided in a dosage that is at least 8 times lower than a dosage of a known desmopressin acetate tablet (e.g., 0.1 mg). In some embodiments, the desmopressin oral liquid compositions are provided in a dosage that is at least 9 times lower than a dosage of a known desmopressin acetate tablet (e.g., 0.1 mg). In some embodiments, the desmopressin oral liquid compositions are provided in a dosage that is at least 10 times lower than a dosage of a known desmopressin acetate tablet (e.g., 0.1 mg). In some embodiments, the desmopressin oral liquid compositions are provided in a dosage that is at least 11 times lower than a dosage of a known desmopressin acetate tablet (e.g., 0.1 mg). In some embodiments, the desmopressin oral liquid compositions are provided in a dosage that is at least 12 times lower than a dosage of a known desmopressin acetate tablet (e.g., 0.1 mg). In some embodiments, the desmopressin oral liquid compositions are provided in a dosage that is at least 13 times lower than a dosage of a known desmopressin acetate tablet (e.g., 0.1 mg). In some embodiments, the desmopressin oral liquid compositions are provided in a dosage that is at least 14 times lower than a dosage of a known desmopressin acetate tablet (e.g., 0.1 mg). In some embodiments, the desmopressin oral liquid compositions are provided in a dosage that is at least 15 times lower than a dosage of a known desmopressin acetate tablet (e.g., 0.1 mg). In some embodiments, the desmopressin oral liquid compositions are provided in a dosage that is at least 16 times lower than a dosage of a known desmopressin acetate tablet (e.g., 0.1 mg). In some embodiments, the desmopressin oral liquid compositions are provided in a dosage that is at least 17 times lower than a dosage of a known desmopressin acetate tablet (e.g., 0.1 mg). In some embodiments, the desmopressin oral liquid compositions are provided in a dosage that is at least 18 times lower than a dosage of a known desmopressin acetate tablet (e.g., 0.1 mg). In some embodiments, the desmopressin oral liquid compositions are provided in a dosage that is at least 19 times lower than a dosage of a known desmopressin acetate tablet (e.g., 0.1 mg). In some embodiments, the desmopressin oral liquid compositions are provided in a dosage that is at least 20 times lower than a dosage of a known desmopressin acetate tablet formulation (e.g., 0.1 mg). In further embodiments, the desmopressin oral liquid compositions are provided in a dosage that is similar, comparable or equivalent to a dosage of a known desmopressin acetate tablet formulation (e.g., 0.1 mg or 0.2 mg).

Further Combinations

The treatment of certain diseases or conditions (e.g., central diabetes insipidus, primary nocturnal enuresis and others) in a subject with a desmopressin oral liquid pharmaceutical composition described herein encompass additional therapies and treatment regimens with other agents in some embodiments. Such additional therapies and treatment regimens can include another therapy, e.g., anticholinergic medication, such as oxybutynin, for treatment of the particular disease or condition in some embodiments. In one instance, desmopressin oral liquid composition can be used in conjunction with anticholinergic medication, such as oxybutynin to treat nocturnal enuresis where applicable. Alternatively, in other embodiments, additional therapies and treatment regimens include other agents used to treat adjunct conditions associated with the disease or condition or a side effect from the desmopressin oral liquid composition in the therapy.

Preparation of Desmopressin Oral Liquid Formulations

Preparation of the desmopressin oral liquid composition described herein includes any known pharmaceutical method. In one embodiment, the desmopressin oral liquid composition described herein is prepared by mixing desmopressin free base or a pharmaceutically acceptable salt thereof (e.g., desmopressin acetate) with a solvent (e.g., water), thereby forming a solution of desmopressin, e.g., in a compounding container. In some cases, the method comprises adding a buffer system (e.g., a two-component, dual-functional, preservative-buffer system or a buffer system that also functions as a preservative as described herein) into the solution of desmopressin. In some cases, the buffer system is added to water before mixing desmopressin free base or a pharmaceutically acceptable salt thereof with water. In some cases, the buffer system is added to the solvent (e.g., water) after mixing desmopressin free base or a pharmaceutically acceptable salt thereof with the solvent (e.g., water). In some cases, the method comprises adding a preservative into the solution of desmopressin. In some cases, the preservative is added to the solvent (e.g., water) before mixing desmopressin free base or a pharmaceutically acceptable salt thereof with the solvent (e.g., water). In some cases, the preservative is added to the solvent (e.g., water) after mixing desmopressin free base or a pharmaceutically acceptable salt thereof with the solvent (e.g., water). In some cases, the method comprises adding a flavoring agent or a sweeter into the solution of desmopressin. In some cases, the preservative, optionally the sweeter, and optionally the flavoring agent is added to with the solvent (e.g., water) before mixing desmopressin acetate or a pharmaceutically acceptable salt thereof with the nonaqueous liquid carrier. In some cases, the method comprises adding a desirable amount of the solvent (e.g., water) to make up the final volume. In some instances, the method comprises optionally filtering the solution of desmopressin over a filter into a container. In some embodiments, the desmopressin or a pharmaceutically acceptable salt thereof and the excipients such as a buffer system (e.g., a two-component, dual-functional, preservative-buffer system or a buffer system that also functions as a preservative as described herein), and optionally preservative, a sweetener and a flavoring agent, can be combined in any order of addition. In some embodiments, the method comprises testing pH of the composition and adjusting the pH by adding an additional amount of buffer system to about 4.5 to about 5.5, or to about 5.0. In some embodiments, the testing and adjusting the pH is performed before adding desmopressin free base or a pharmaceutically acceptable salt thereof.

In some embodiments, a method of making a desmopressin oral liquid composition described herein further comprises adding a liquid carrier as described herein. In some embodiments, the method comprises dissolving desmopressin or a pharmaceutically acceptable salt thereof in water in a first container thereby forming a solution of desmopressin. In some embodiments, the method comprises dissolving buffer system (e.g., a two-component, dual-functional, preservative-buffer system or a buffer system that also functions as a preservative as described herein) in the water in the first container. In some embodiments, the method comprises adding a liquid carrier in a second container. In some embodiments, the method comprises dissolving a preservative (e.g., an antioxidant), optionally a flavoring agent or sweetener in the liquid carrier in the second container. In some embodiments, the method comprises adding the solvent in the second container to the first container. In some embodiments, the desmopressin or a pharmaceutically acceptable salt thereof, the nonaqueous liquid carrier, and the excipients such as a buffer system, optionally a preservative, a sweetener and a flavoring agent can be combined in any order of addition. In some embodiments, desmopressin free base or a pharmaceutically acceptable salt thereof is added after buffer system, optionally a liquid carrier, preservatives, sweeteners, flavoring agents are combined with water in a compounding container. In some embodiments, a liquid carrier, for example, propylene glycol is added to the compounding container before desmopressin or a pharmaceutically acceptable salt thereof is dissolved. In some embodiments, desmopressin or a pharmaceutically acceptable salt thereof is added after buffer system (e.g., a two-component, dual-functional, preservative-buffer system or a buffer system that also functions as a preservative as described herein) and optionally other excipients are dissolved in a compounding container. In some embodiments, a sufficient amount of water is added after desmopressin or a pharmaceutically acceptable salt thereof to the compounding container to obtain a desirable volume. In some embodiments, the liquid pharmaceutical composition in the compounding container is optionally filtered through a filter unit. In some embodiment, the liquid pharmaceutical composition in the compounding container is stored in a storage tank after filtration. In some embodiments, the method comprises testing pH of the composition and adjusting the pH by adding an additional amount of buffer system to about 4.5 to about 5.5, or to about 5.0. In some embodiments, the testing and adjusting the pH is performed before adding desmopressin free base or a pharmaceutically acceptable salt thereof.

In some embodiments, the present disclosure provides a method for preparing a desmopressin oral liquid pharmaceutical composition described herein, which comprises a) providing a first container containing a solvent (e.g., water); b) adding the buffer system to the container and mixing until the buffer system is dissolved; optionally combining a liquid carrier and an antioxidant in a second container and mixing until they are dissolved; optionally d) combining the contents of the first and second containers to form a combined solution. In some embodiments, the method comprises e) adding desmopressin free base or a pharmaceutically acceptable salts thereof (e.g., desmopressin acetate) to the combined solution from (d) and mixing until the desmopressin free base or a pharmaceutically acceptable salt thereof (e.g., desmopressin acetate) is dissolved; and f) optionally adjusting the volume of the resulting solution form (e) by adding additional solvent (e.g., water). In another embodiment, the method further comprises g) adding the second solvent to the first container, h) optionally testing the pH and adjusting if necessary by adding an additional amount of buffer system; i) adding the desmopressin free base or a pharmaceutically acceptable salt thereof to the combined solution from (i) and mixing until the desmopressin free base or a pharmaceutically acceptable salt thereof is dissolved; and j) optionally adjusting the volume of the resulting solution form (e) by adding additional solvent (e.g., water). In yet another embodiments, the method comprises k) adjusting the volume of the resulting solution from (b) by adding additional solvent; and l) adding the desmopressin free base or a pharmaceutically acceptable salt thereof (e.g., desmopressin acetate) to the combined solution from (i) and mixing until the desmopressin, or a pharmaceutically acceptable salt or base thereof is dissolved. The above-mentioned steps that can be employed in preparing a desmopressin oral liquid pharmaceutical composition described herein can be combined where needed or performed in an order that is different from the numbering of (a), (b), (c) etc., as designated.

Kits and Articles of Manufacture

For the desmopressin acetate liquid compositions described herein, kits and articles of manufacture are also described. In some aspects, provided herein is a kit comprising a package enclosing liquid pharmaceutical compositions described herein or a direct dosing device described herein. Such kits can comprise a carrier, package, or container that is compartmentalized to receive one or more containers such as bottles, vials, tubes, and the like, each of the container(s) comprising one of the separate elements to be used in a method described herein including a desmopressin acetate liquid composition. Suitable containers include, for example, tanks, bottles, vials, syringes, and test tubes. The containers can be formed from a variety of materials such as glass or plastic. The containers can further comprise a light protection mechanism, for example, an amber glass bottle. The containers can have different sizes, such as about 12 oz, about 10 oz, about 8 oz, or about 4 oz. The containers can have seal, such as induction seal. In some embodiments, the kit comprises a package enclosing the liquid pharmaceutical composition described herein. In some embodiments, the package is a bottle. In some embodiments, the kit comprises a package enclosing a liquid pharmaceutical composition described herein and further comprises a direct dosing device described herein (e.g., an oral syringe with graduated marks).

A kit can comprise one or more additional containers, each with one or more of various materials (such as reagents, optionally in concentrated form, and/or devices) desirable from a commercial and user standpoint for a desmopressin acetate liquid composition described herein. Non-limiting examples of such materials include, but not limited to, needles, syringes, carrier, package, container, vial and/or tube labels listing contents and/or instructions for use, and package inserts with instructions for use associated with a desmopressin oral liquid formulation described herein. A set of instructions can also be included. In some embodiments, the kit comprises instructions for use of the liquid pharmaceutical compositions described herein.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as desmopressin acetate is directed to the treatment and/or the amelioration of, reversal of, or stabilization of the symptoms of central diabetes insipidus, primary nocturnal enuresis, and other conditions described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with a desmopressin acetate formulation, can include, but is not limited to providing a desmopressin acetate formulation systemically to a patient by, e.g., oral administration whereby the therapeutic reaches the target tissue or cells. "Administering" a formulation may be accomplished by oral administration, injection, topical administration, or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with central diabetes insipidus, primary nocturnal enuresis, or other conditions described herein. A patient can be a human suffering from central diabetes insipidus or primary nocturnal enuresis other conditions described herein.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Effective amount," and "sufficient amount" may be used interchangeably, and refer to an amount of a substance that is sufficient to achieve an intended purpose or objective.

A "therapeutically effective amount" when used in connection with a pharmaceutical composition described herein is an amount of one or more pharmaceutically active agent(s) sufficient to produce a therapeutic result in a subject in need thereof.

"Therapeutically equivalent" when used in connection with a pharmaceutical composition described herein refers to an amount or quantity of a pharmaceutically acceptable salt or ester of a pharmaceutically active agent that is equivalent to the therapeutically effective amount of the free base or alcohol of the pharmaceutically active agent.

The terms "treat," "treated," "treatment," or "treating" as used herein refers to therapeutic treatment, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example A: Preparation of Desmopressin Formulations

Desmopressin acetate compositions in accordance with some embodiments of the present disclosure is prepared containing the ingredients as described in Table A-1.

TABLE A-1

Desmopressin Formulation Compositions

| | Weight by Volume percentage concentration (% w/v) | | | | | | |
|---|---|---|---|---|---|---|---|
| Ingredient | A RB0059-130H | B RB0059-143A | C RB0317-2A | D RB0317-6A (2.5X) | E RB0317-6B (10X) | F RB0317-2B | G RB0317-7A (2.5X) |
| Water (initial amount) | 90 | 90 | 90 | 90 | 90 | 90 | 90 |
| Benzoic Acid | 0.03 | 0.03 | 0.03 | 0.02 | 0.02 | 0.02 | 0.02 |
| Sodium Benzoate | 0.07 | 0.07 | 0.07 | 0.0442 | 0.0442 | 0.19 | 0.1654 |
| Propylene Glycol | 5 | 5 | 5 | — | — | 5 | — |
| BHA | 0.01 | 0.01 | — | — | — | — | — |
| Desmopressin Acetate | 0.001 | 0.001 | 0.001 | 0.00264 | 0.01 | 0.001 | 0.00264 |
| Final volume (Qs with water) | Qs to 500 mL | Qs to 1000 mL | Qs to 500 mL | Qs to 1000 mL | Qs to 1000 mL | Qs to 500 mL | Qs to 1000 mL |
| API Strength | 0.01 mg/mL | 0.01 mg/mL | 0.01 mg/mL | 0.026 mg/mL | 0.1 mg/mL | 0.01 mg/mL | 0.026 mg/mL |
| Initial pH | 4.52 | 4.51 | 4.5 | 4.5 | 4.5 | 5.0 | 5.0 |

| | Weight by Volume percentage concentration (% w/v) | | | | | |
|---|---|---|---|---|---|---|
| Ingredient | H RB0317-7B (10X) | I RB0059-143C | J RB0317-2C | K RB0317-8A | L RB0317-47B | M RB0317-49B |
| Water (initial amount) | 90 | 90 | 90 | 90 | 90 | 90 |
| Benzoic Acid | 0.02 | 0.02 | 0.02 | 0.02 | 0.0342 | 0.1 |
| Sodium Benzoate | 0.1654 | 0.50 | 0.472 | 0.1654 | 0.285 | 0.425 |
| Propylene Glycol | — | 5 | 5 | — | — | — |
| BHA | — | 0.01 | — | — | — | — |
| Desmopressin Acetate | 0.01 | 0.001 | 0.001 | 0.005 | 0.005 | 0.005 |
| Final volume (Qs with water) | Qs to 1000 mL | Qs to 1000 mL | Qs to 500 mL | Qs to 1000 mL | Qs to 1000 mL | Qs to 1000 mL |
| API Strength | 0.1 mg/mL | 0.01 mg/mL | 0.01 mg/mL | 0.05 mg/mL | 0.05 mg/mL | 0.05 mg/mL |
| Initial pH | 5.0 | 5.5 | 5.5 | 5.0 | 5.0 | 4.71 |

Qs = Quantum satis, or sufficient quantity

Preparation of Compositions A, B and I

Purified water was added to the main container. The benzoic acid and sodium benzoate were then added to the container and mixed until dissolved. Propylene glycol was weighed into a separate container, to which was also added BHA, and the contents were mixed until they dissolved. The propylene glycol solution was transferred to the main container and the contents mixed well. The desmopressin acetate was then added to the main container and the contents mixed until dissolved. Purified water was then added to achieve the desired final volume.

Preparation of Compositions C, F and J:

Purified water was added to the main container. The benzoic acid and sodium benzoate were then added to the container and mixed until dissolved. Propylene glycol was added to the same container, and the contents were mixed well. The pH of the solution was then tested and adjusted by addition of either sodium benzoate or benzoic acid. The desmopressin acetate was then added to the main container and the contents mixed until dissolved. Purified water was then added to achieve the desired final volume.

Manufacturing Procedure for D, E, G, H, K, L and M

Purified water (~90% of the theoretical amount initially) was added to the main container. The benzoic acid and sodium benzoate were then added to the container and mixed until dissolved. Purified water was then added achieve the desired final volume, and then the desmopressin acetate was then added to the main container and the contents mixed until dissolved.

Additional desmopressin compositions were prepared according to Tables A-2, A-3, A-4, A5, A-6, A-7, and A-8.

TABLE A-2

Desmopressin Formulation Composition with benzoic acid and sodium benzoate at a lower ionic strength
Batch No.: RB0317-11A (pH 5.0)

| Ingredient | % w/v | Weight (g) |
|---|---|---|
| Water (initial amount) | 90 | 900 |
| Benzoic Acid | 0.01 | 0.1 |
| Sodium Benzoate | 0.0827 | 0.827 |
| Desmopressin Acetate | 0.005 | 0.05 |
| Water | Qs to 100 mL | Qs to 1000 mL |

Qs = Quantum satis, or sufficient quantity

Manufacturing Process for Batch No.: RB0317-11A

Purified water (~90% of the theoretical amount initially) was added to the main container. The benzoic acid and sodium benzoate were then added to the main container and mixed until dissolved. The desmopressin acetate was then added to the main container and was mixed until dissolved. Purified water was then added to achieve the desired final volume.

TABLE A-3

Desmopressin Formulation Composition with citric acid, sodium citrate buffer, propylene glycol and preservatives
Batch No.: RB0059-130B (pH 4.5)

| Ingredient | Weight (g) |
|---|---|
| Water (initial amount) | 450 |
| Citric Acid | 2.5 |
| Sodium Citrate | 3.65 |
| Propylene Glycol | 25 |
| Propylparaben | 0.1 |
| Methylparaben | 0.9 |
| BHA | 0.05 |
| Desmopressin Acetate | 0.005 |
| Water | Qs 500 mL |

Qs = Quantum satis, or sufficient quantity

Manufacturing Process for Batch No.: RB0059-130B

Purified water (~90% of the theoretical amount initially) was added to the main container. The citric acid and sodium citrate were then added to the main container and mixed until dissolved. Propylene glycol was added to a second container. The methylparaben, propylparaben, and BHA were then added to the second container with propylene glycol and were mixed until dissolved. Then, the propylene glycol solution from the second container was added to the main container. The desmopressin acetate was then added to the main container and was mixed until dissolved. Purified water was then added to achieve the desired final volume.

TABLE A-4

Desmopressin Formulation Composition with citric acid, sodium hydroxide, propylene glycol and preservatives
Batch No.: RB0059-130D (pH 4.5)

| Ingredient | Weight (g) |
|---|---|
| Water (initial amount) | 450 |
| Citric Acid | 3 |
| 1N NaOH | 24.25 |
| EDTA | 0.5 |
| Propylene Glycol | 25 |
| Propylparaben | 0.1 |
| Methylparaben | 0.9 |
| BHA | 0.05 |
| Desmopressin Acetate | 0.005 |
| Water | Qs 500 mL |

Qs = Quantum satis, or sufficient quantity

Manufacturing Process for Batch No.: RB0059-130D

Purified water (~90% of the theoretical amount initially) was added to the main container. The citric acid and NaOH were then added to the main container and mixed until dissolved. The EDTA was added to the main container and was mixed until dissolved. Propylene glycol was added to a second container. The methylparaben, propylparaben, and BHA were then added to the second container with propylene glycol and were mixed until dissolved. Then, the propylene glycol solution from the second container was added to the main container. The desmopressin acetate was then added to the main container and was mixed until dissolved. Purified water was then added to achieve the desired final volume.

TABLE A-5

Desmopressin Formulation Composition with EDTA, Propylene glycol and BHA
Batch No.: RB0059-130J (pH 4.5)

| Ingredient | Weight (g) |
|---|---|
| Water (initial amount) | 450 |
| EDTA | 0.5 |
| Propylene Glycol | 25 |
| BHA | 0.05 |
| Desmopressin Acetate | 0.005 |
| Water | Qs 500 mL |

Qs = Quantum satis, or sufficient quantity

Manufacturing Process for Batch No.: RB0059-130J

Purified water (~90% of the theoretical amount initially) was added to the main container. The EDTA was added to the main container and was mixed until dissolved. Propylene glycol was added to a second container. The BHA was added to the second container with propylene glycol and were mixed until dissolved. Then, the propylene glycol solution from the second container was added to the main container. The desmopressin acetate was then added to the main container and was mixed until dissolved. Purified water was then added to achieve the desired final volume.

TABLE A-6

Desmopressin Formulation Composition with citric
acid, sodium benzoate, EDTA and propylene glycol
Batch No.: RB0059-130K (pH 4.5)

| Ingredient | Weight (g) |
| --- | --- |
| Water (initial amount) | 450 |
| Citric Acid | 0.15 |
| Sodium Benzoate | 0.5 |
| EDTA | 0.5 |
| Propylene Glycol | 25 |
| BHA | 0.05 |
| Desmopressin Acetate | 0.005 |
| Water | Qs 500 mL |

Qs = Quantum satis, or sufficient quantity

Manufacturing Process for Batch No.: RB0059-130K

Purified water (~90% of the theoretical amount initially) was added to the main container. The citric acid and sodium benzoate were then added to the main container and mixed until dissolved. The EDTA was added to the main container and was mixed until dissolved. Propylene glycol was added to a second container. The BHA was added to the second container with propylene glycol and were mixed until dissolved. Then, the propylene glycol solution from the second container was added to the main container. The desmopressin acetate was then added to the main container and was mixed until dissolved. Purified water was then added to achieve the desired final volume.

TABLE A-7

Desmopressin Formulation Composition with tartaric
acid, sodium hydroxide, propylene glycol and preservatives
Batch No.: RB0059-130M (pH 4.5)

| Ingredient | Weight (g) |
| --- | --- |
| Water (initial amount) | 450 |
| Tartaric Acid | 3 |
| 1N NaOH | 35.45 |
| Propylene Glycol | 25 |
| Propylparaben | 0.1 |
| Methylparaben | 0.9 |
| BHA | 0.05 |
| Desmopressin Acetate | 0.005 |
| Water | Qs 500 mL |

Qs = Quantum satis, or sufficient quantity

Manufacturing Process for Batch No.: RB0059-130M

Purified water (~90% of the theoretical amount initially) was added to the main container. The tartaric acid and NaOH were then added to the main container and mixed until dissolved. Propylene glycol was added to a second container. The methylparaben, propylparaben and BHA were added to the second container with propylene glycol and were mixed until dissolved. Then, the propylene glycol solution from the second container was added to the main container. The desmopressin acetate was then added to the main container and was mixed until dissolved. Purified water was then added to achieve the desired final volume.

TABLE A-8

Desmopressin Formulation Composition with
benzoic acid and sodium benzoate
Batch No.: RB0317-21A (pH 5.0)

| Ingredient | % w/v | Weight (g) |
| --- | --- | --- |
| Water (initial amount) | 90 | 4500 |
| Benzoic Acid | 0.02 | 1 |
| Sodium Benzoate | 0.186 | 9.30 |
| Desmopressin Acetate | 0.005 | 0.25 |
| Water | Qs to 100 mL | Qs to 5000 mL |

Qs = Quantum satis, or sufficient quantity

Manufacturing Process for Batch No.: RB0317-21A

Purified water (~90% of the theoretical amount initially) was added to the main container. The benzoic acid and sodium benzoate were then added to the main container and mixed until dissolved. The desmopressin acetate was then added to the main container and was mixed until dissolved. Purified water was then added to achieve the desired final volume.

Example B—Stability and Forced Degradation Results of the Compositions

Desmopressin composition Batch No.: RB0317-9A was made according to Composition K (RB0317-8A) in Table A-1 and was tested for assay and impurity when placed for stability testing at about 25° C. and about 60% RH and at about 40° C. and about 75% RH. The testing results of 1 month and 2 months stability under both conditions are summarized in Table B-1.

TABLE B-1

Stability data for desmopressin acetate oral solution
0.05 mg/ml (Batch No.: RB0317-9A) (pH 5.0)

| Batch No.: RB0317-9A | Assay (%) | Total Imp (%) | Imp 2 $Asp^5$ (%) | Imp 7 $Gly^9OH$ (%) | Imp 4 $Glu^4$ (%) | Imp 5 $L\text{-}Arg^8$ (%) | Imp 3 $Gln^4(ACM)$ (%) | Imp 6 $Asn^5(ACM)$ (%) |
| --- | --- | --- | --- | --- | --- | --- | --- | --- |
| Initial | 100.8 | 0.17 | 0.03 | ND | 0.06 | 0.05 | 0.03 | ND |
| 1 m-25/60 | 99.8 | 0.20 | 0.06 | ND | 0.09 | 0.05 | ND | ND |
| 2 m-25/60 | 100.3 | 0.34 | 0.06 | 0.07 | 0.08 | 0.06 | 0.03 | ND |
| 1 m-40/75 | 99.2 | 0.61 | 0.09 | 0.18 | 0.11 | 0.06 | ND | ND |
| 2 m-40/75 | 99.1 | 0.90 | 0.15 | 0.34 | 0.16 | 0.05 | ND | 0.10 |

ND = not detected

Forced degradation studies were performed for Composition K (Batch No.: RB0317-8A) under various conditions, including, 80° C., 0.1N HCl at 60° C., 0.1 N NaOH at ambient, 2% H₂O₂ at ambient, white light at 1.2 million Lux-hours, and UV at 200 Watts-hours per sq meter. The forced degradation results are summarized in Tables B-2 to B-7.

TABLE B-2

Thermal Degradation Results for Batch No.: RB0317-8A
RB0317-8A Desmopressin Composition 0.05 mg/mL Thermal Degradation

| Impurities | Condition: 80° C. Oven 4 Days | | | Label Claim | | Desmopressin Actual Conc. | | |
|---|---|---|---|---|---|---|---|---|
| | Retention Time | RRT | RRF | (mg/mL) Area | 0.050 % Area | (mg/mL) % Impurity | 0.04755 Results |
| RRT~0.488 | 13.174 | 0.488 | 1.00 | 2077 | 0.03 | 0.029 | 0.03 |
| RRT~0.496 | 13.402 | 0.496 | 1.00 | 2613 | 0.04 | 0.037 | 0.04 |
| RRT~0.506 | 13.651 | 0.506 | 1.00 | 7434 | 0.11 | 0.104 | 0.10 |
| RRT~0.518 | 13.971 | 0.518 | 1.00 | 3257 | 0.05 | 0.046 | 0.05 |
| Unknown_5 | 14.866 | 0.551 | 1.00 | 4257 | 0.06 | 0.060 | 0.06 |
| RRT~0.567 | 15.303 | 0.567 | 1.00 | 3046 | 0.04 | 0.043 | 0.04 |
| RRT~0.591 | 15.962 | 0.591 | 1.00 | 1104 | 0.02 | 0.015 | 0.02 |
| Unknown~0.613 | 16.598 | 0.615 | 1.00 | 2434 | 0.03 | 0.034 | 0.03 |
| RRT~0.629 | 16.978 | 0.629 | 1.00 | 4727 | 0.07 | 0.066 | 0.07 |
| RRT~0.651 | 17.572 | 0.651 | 1.00 | 876 | 0.01 | 0.012 | 0.01 |
| Unknown~0.668 | 18.017 | 0.667 | 1.00 | 2589 | 0.04 | 0.036 | 0.04 |
| RRT~0.679 | 18.320 | 0.679 | 1.00 | 910 | 0.01 | 0.013 | 0.01 |
| RRT~0.742 | 20.043 | 0.742 | 1.00 | 1192 | 0.02 | 0.017 | 0.02 |
| Unknown_4 | 20.361 | 0.754 | 1.00 | 4840 | 0.07 | 0.068 | 0.07 |
| RRT~0.769 | 20.767 | 0.769 | 1.00 | 3228 | 0.05 | 0.045 | 0.05 |
| Unknown~0.799 | 21.472 | 0.795 | 1.00 | 4248 | 0.06 | 0.059 | 0.06 |
| RRT~0.804 | 21.703 | 0.804 | 1.00 | 2482 | 0.04 | 0.035 | 0.03 |
| Unknown~0.826 | 22.223 | 0.823 | 1.00 | 3434 | 0.05 | 0.048 | 0.05 |
| RRT~0.842 | 22.721 | 0.842 | 1.00 | 1951 | 0.03 | 0.027 | 0.03 |
| Unknown~0.872 | 23.469 | 0.869 | 1.00 | 10746 | 0.15 | 0.150 | 0.15 |
| RRT~0.882 | 23.814 | 0.882 | 1.00 | 6479 | 0.09 | 0.091 | 0.09 |
| RRT~0.892 | 24.071 | 0.892 | 1.00 | 3819 | 0.05 | 0.053 | 0.05 |
| RRT~0.908 | 24.500 | 0.908 | 1.00 | 31339 | 0.45 | 0.439 | 0.44 |
| Glu-4/Imp 4 | 24.992 | 0.926 | 1.00 | 20205 | 0.29 | 0.283 | 0.28 |
| Asp5/Imp 7 | 25.470 | 0.944 | 1.00 | 129830 | 1.86 | 1.818 | 1.82 |
| Gly9OH/Imp 2 | 25.747 | 0.954 | 1.00 | 25719 | 0.37 | 0.360 | 0.36 |
| RRT~0.966 | 26.087 | 0.966 | 1.00 | 2421 | 0.03 | 0.034 | 0.03 |
| RRT~0.976 | 26.360 | 0.976 | 1.00 | 871 | 0.01 | 0.012 | 0.01 |
| L-Arg8 | 26.534 | 0.983 | 1.00 | 6125 | 0.09 | 0.086 | 0.09 |
| RRT~0.991 | 26.749 | 0.991 | 1.00 | 1114 | 0.02 | 0.016 | 0.02 |
| Desmopressin | 26.995 | 1.000 | 1.00 | 6619536 | 94.60 | 92.707 | 92.71 |
| ASn5(ACM) | 27.708 | 1.026 | 1.00 | 13189 | 0.19 | 0.185 | 0.18 |
| Gln6(ACM) | 28.014 | 1.038 | 1.00 | 4940 | 0.07 | 0.069 | 0.07 |
| Gly9-NMe2 | 28.785 | 1.066 | 1.00 | 1496 | 0.02 | 0.021 | 0.02 |
| Unknown~1.096 | 29.238 | 1.083 | 1.00 | 1743 | 0.02 | 0.024 | 0.02 |
| RRT~1.098 | 29.628 | 1.098 | 1.00 | 36275 | 0.52 | 0.508 | 0.51 |
| RRT~1.117 | 30.160 | 1.117 | 1.00 | 21096 | 0.30 | 0.295 | 0.30 |
| RRT~1.238 | 33.411 | 1.238 | 1.00 | 2144 | 0.03 | 0.030 | 0.03 |
| Gly9-OnBu | 37.523 | 1.390 | 1.00 | 1725 | 0.02 | 0.024 | 0.02 |
| Total (%) | | | | 6997511 | 100.0 | Mass Balance | 98.01 |

TABLE B-3

Acid Degradation Results for Batch No.: RB0317-8A
RB0317-8A Desmopressin Composition 0.05 mg/mL Acid Degradation

| Impurities | Condition: 0.1N HCl 60° C. 1 hDilution 1.25 | | | Label Claim | | Desmopressin Actual Conc. | |
|---|---|---|---|---|---|---|---|
| | Retention Time | RRT | RRF | (mg/mL) Area | 0.050 % Area | (mg/mL) % Impurity | 0.03804 Results |
| RRT~0.516 | 13.917 | 0.516 | 1.00 | 922 | 0.02 | 0.016 | 0.02 |
| RRT~0.566 | 15.274 | 0.566 | 1.00 | 3306 | 0.06 | 0.058 | 0.06 |
| Unknown~0.668 | 17.999 | 0.667 | 1.00 | 10195 | 0.18 | 0.178 | 0.18 |
| Unknown~0.722 | 19.503 | 0.723 | 1.00 | 5584 | 0.10 | 0.098 | 0.10 |
| Unknown~0.799 | 21.461 | 0.795 | 1.00 | 2254 | 0.04 | 0.039 | 0.04 |
| RRT~0.808 | 21.815 | 0.808 | 1.00 | 3224 | 0.06 | 0.056 | 0.06 |

TABLE B-3-continued

Acid Degradation Results for Batch No.: RB0317-8A
RB0317-8A Desmopressin Composition 0.05 mg/mL Acid Degradation

| Impurities | Condition: 0.1N HCl 60° C. 1 hDilution 1.25 | | | Label Claim | | Desmopressin Actual Conc. | | |
|---|---|---|---|---|---|---|---|---|
| | Retention Time | RRT | RRF | (mg/mL) Area | 0.050 % Area | (mg/mL) % Impurity | 0.03804 Results |
| Unknown~0.826 | 22.085 | 0.818 | 1.00 | 22982 | 0.40 | 0.402 | 0.40 |
| RRT~0.844 | 22.789 | 0.844 | 1.00 | 5615 | 0.10 | 0.098 | 0.10 |
| Unknown~0.872 | 23.454 | 0.869 | 1.00 | 9260 | 0.16 | 0.162 | 0.16 |
| RRT~0.881 | 23.778 | 0.881 | 1.00 | 3840 | 0.07 | 0.067 | 0.07 |
| RRT~0.893 | 24.108 | 0.893 | 1.00 | 3016 | 0.05 | 0.053 | 0.05 |
| RRT~0.914 | 24.664 | 0.914 | 1.00 | 7014 | 0.12 | 0.123 | 0.12 |
| Glu-4/Imp 4 | 24.963 | 0.925 | 1.00 | 223965 | 3.91 | 3.921 | 3.92 |
| Asp5/Imp 7 | 25.366 | 0.940 | 1.00 | 68732 | 1.20 | 1.203 | 1.20 |
| Gly9OH/Imp 2 | 25.717 | 0.953 | 1.00 | 196425 | 3.43 | 3.439 | 3.44 |
| L-Arg8 | 26.471 | 0.981 | 1.00 | 3299 | 0.06 | 0.058 | 0.06 |
| Desmopressin | 26.988 | 1.000 | 1.00 | 5142188 | 89.75 | 90.021 | 90.02 |
| Gln6(ACM) | 27.984 | 1.037 | 1.00 | 4726 | 0.08 | 0.083 | 0.08 |
| Unknown~1.096 | 29.596 | 1.097 | 1.00 | 3956 | 0.07 | 0.069 | 0.07 |
| Unknown~1.116 | 30.118 | 1.116 | 1.00 | 5438 | 0.09 | 0.095 | 0.10 |
| RRT~1.236 | 33.370 | 1.236 | 1.00 | 1925 | 0.03 | 0.034 | 0.03 |
| RRT~1.323 | 35.711 | 1.323 | 1.00 | 1539 | 0.03 | 0.027 | 0.03 |
| Total (%) | | | | 5729405 | 100.0 | Mass Balance | 100.31 |

TABLE B-4

Base Degradation Results for Batch No.: RB0317-8A
RB0317-8A Desmopressin Composition 0.05 mg/mL Base Degradation

| Impurities | Condition: 0.1N NaOH Ambient 25 min; Dilution 1.25 | | | Label Claim | | Desmopressin Actual Conc. | | |
|---|---|---|---|---|---|---|---|---|
| | Retention Time | RRT | RRF | (mg/mL) Area | 0.050 % Area | (mg/mL) % Impurity | 0.03804 Results |
| RRT~0.518 | 13.978 | 0.518 | 1.00 | 2843 | 0.05 | 0.050 | 0.05 |
| Unknown__5 | 14.814 | 0.549 | 1.00 | 3673 | 0.06 | 0.064 | 0.06 |
| Unknown__4 | 20.733 | 0.768 | 1.00 | 2022 | 0.04 | 0.035 | 0.04 |
| Unknown~0.799 | 21.447 | 0.795 | 1.00 | 1561 | 0.03 | 0.027 | 0.03 |
| Unknown~0.826 | 22.066 | 0.818 | 1.00 | 10185 | 0.18 | 0.178 | 0.18 |
| Unknown~0.872 | 23.460 | 0.869 | 1.00 | 9655 | 0.17 | 0.169 | 0.17 |
| RRT~0.883 | 23.838 | 0.883 | 1.00 | 870 | 0.02 | 0.015 | 0.02 |
| RRT~0.893 | 24.100 | 0.893 | 1.00 | 2559 | 0.04 | 0.045 | 0.04 |
| RRT~0.915 | 24.699 | 0.915 | 1.00 | 3904 | 0.07 | 0.068 | 0.07 |
| Glu-4/Imp 4 | 24.961 | 0.925 | 1.00 | 10125 | 0.18 | 0.177 | 0.18 |
| Asp5/Imp 7 | 25.261 | 0.936 | 1.00 | 38664 | 0.67 | 0.677 | 0.68 |
| Gly9OH/Imp 2 | 25.720 | 0.953 | 1.00 | 18431 | 0.32 | 0.323 | 0.32 |
| L-Arg8 | 26.494 | 0.982 | 1.00 | 5508 | 0.10 | 0.096 | 0.10 |
| Desmopressin | 26.988 | 1.000 | 1.00 | 5486913 | 95.38 | 96.056 | 96.06 |
| Gln6(ACM) | 27.969 | 1.036 | 1.00 | 3867 | 0.07 | 0.068 | 0.07 |
| ASn5(ACM) | 28.178 | 1.044 | 1.00 | 2448 | 0.04 | 0.043 | 0.04 |
| Gly9-NMe2 | 28.888 | 1.070 | 1.00 | 5827 | 0.10 | 0.102 | 0.10 |
| Unknown~1.096 | 29.608 | 1.097 | 1.00 | 34672 | 0.60 | 0.607 | 0.61 |
| Unknown~1.116 | 30.117 | 1.116 | 1.00 | 90768 | 1.58 | 1.589 | 1.59 |
| Unknown~1.204 | 32.503 | 1.204 | 1.00 | 2391 | 0.04 | 0.042 | 0.04 |
| RRT~1.215 | 32.796 | 1.215 | 1.00 | 2405 | 0.04 | 0.042 | 0.04 |
| RRT~1.237 | 33.371 | 1.237 | 1.00 | 6765 | 0.12 | 0.118 | 0.12 |
| RRT~1.257 | 33.917 | 1.257 | 1.00 | 1792 | 0.03 | 0.031 | 0.03 |
| RRT~1.322 | 35.668 | 1.322 | 1.00 | 2947 | 0.05 | 0.052 | 0.05 |
| RRT~1.342 | 36.209 | 1.342 | 1.00 | 1896 | 0.03 | 0.033 | 0.03 |
| Total (%) | | | | 5752691 | 100.0 | Mass Balance | 100.72 |

TABLE B-5

Forced Degradation under Oxidation Results for Batch No.: RB0317-8A
RB0317-8A Desmopressin Composition 0.05 mg/mL Oxidation

| Condition: 2% H2O2 Ambient 2 hours | | | | Label Claim | | Desmopressin Actual Conc. | |
|---|---|---|---|---|---|---|---|
| | Retention | Dilution 1.03 | | (mg/mL) | 0.050 | (mg/mL) | 0.04617 |
| Impurities | Time | RRT | RRF | Area | % Area | % Impurity | Results |
| RRT~0.480 | 12.961 | 0.480 | 1.00 | 6495 | 0.10 | 0.094 | 0.09 |
| RRT~0.502 | 13.547 | 0.502 | 1.00 | 15343 | 0.23 | 0.221 | 0.22 |
| RRT~0.511 | 13.804 | 0.512 | 1.00 | 6457 | 0.10 | 0.093 | 0.09 |
| RRT~0.534 | 14.413 | 0.534 | 1.00 | 15243 | 0.23 | 0.220 | 0.22 |
| RRT~0.566 | 15.273 | 0.566 | 1.00 | 10292 | 0.15 | 0.148 | 0.15 |
| RRT~0.581 | 15.674 | 0.581 | 1.00 | 6424 | 0.10 | 0.093 | 0.09 |
| RRT~0.591 | 15.947 | 0.591 | 1.00 | 483421 | 7.28 | 6.973 | 6.97 |
| RRT~0.640 | 17.259 | 0.640 | 1.00 | 11862 | 0.18 | 0.171 | 0.17 |
| RRT~0.652 | 17.606 | 0.652 | 1.00 | 7795 | 0.12 | 0.112 | 0.11 |
| Unknown~0.668 | 17.871 | 0.662 | 1.00 | 2307 | 0.03 | 0.033 | 0.03 |
| RRT~0.680 | 18.363 | 0.680 | 1.00 | 3165 | 0.05 | 0.046 | 0.05 |
| RRT~0.687 | 18.527 | 0.687 | 1.00 | 1209 | 0.02 | 0.017 | 0.02 |
| RRT~0.730 | 19.692 | 0.730 | 1.00 | 4775 | 0.07 | 0.069 | 0.07 |
| RRT~0.740 | 19.971 | 0.740 | 1.00 | 1168 | 0.02 | 0.017 | 0.02 |
| Unknown_4 | 20.437 | 0.757 | 1.00 | 4865 | 0.07 | 0.070 | 0.07 |
| RRT~0.774 | 20.894 | 0.774 | 1.00 | 9587 | 0.14 | 0.138 | 0.14 |
| Unknown~0.799 | 21.182 | 0.785 | 1.00 | 1455 | 0.02 | 0.021 | 0.02 |
| RRT~0.805 | 21.724 | 0.805 | 1.00 | 2117 | 0.03 | 0.031 | 0.03 |
| Unknown~0.826 | 22.252 | 0.825 | 1.00 | 114231 | 1.72 | 1.648 | 1.65 |
| RRT~0.842 | 22.735 | 0.842 | 1.00 | 1730 | 0.03 | 0.025 | 0.02 |
| RRT~0.857 | 23.140 | 0.857 | 1.00 | 2575 | 0.04 | 0.037 | 0.04 |
| Unknown~0.872 | 23.477 | 0.870 | 1.00 | 9441 | 0.14 | 0.136 | 0.14 |
| RRT~0.893 | 24.100 | 0.893 | 1.00 | 132717 | 2.00 | 1.914 | 1.91 |
| RRT~0.914 | 24.668 | 0.914 | 1.00 | 272137 | 4.10 | 3.926 | 3.93 |
| Glu-4/Imp 4 | 25.179 | 0.933 | 1.00 | 1068 | 0.02 | 0.015 | 0.02 |
| Asp5/Imp 7 | 25.403 | 0.941 | 1.00 | 2150 | 0.03 | 0.031 | 0.03 |
| Gly9OH/Imp 2 | 25.716 | 0.953 | 1.00 | 4186 | 0.06 | 0.060 | 0.06 |
| L-Arg8 | 26.502 | 0.982 | 1.00 | 2412 | 0.04 | 0.035 | 0.03 |
| RRT~0.990 | 26.720 | 0.990 | 1.00 | 10430 | 0.16 | 0.150 | 0.15 |
| Desmopressin | 26.987 | 1.000 | 1.00 | 5472388 | 82.39 | 78.941 | 78.94 |
| Gln6(ACM) | 27.977 | 1.037 | 1.00 | 3703 | 0.06 | 0.053 | 0.05 |
| ASn5(ACM) | 28.147 | 1.043 | 1.00 | 1544 | 0.02 | 0.022 | 0.02 |
| Unknown~1.083 | 29.229 | 1.083 | 1.00 | 9613 | 0.14 | 0.139 | 0.14 |
| RRT~1.097 | 29.617 | 1.097 | 1.00 | 2045 | 0.03 | 0.029 | 0.03 |
| Unknown~1.126 | 30.384 | 1.126 | 1.00 | 2389 | 0.04 | 0.034 | 0.03 |
| Unknown~1.166 | 31.474 | 1.166 | 1.00 | 1949 | 0.03 | 0.028 | 0.03 |
| RRT~1.204 | 32.485 | 1.204 | 1.00 | 1469 | 0.02 | 0.021 | 0.02 |
| Total (%) | | | | 6642157 | 100.0 | Mass Balance | 95.80 |

TABLE B-6

Forced Degradation under White Light for Batch No.: RB0317-8A
RB0317-8A Desmopressin Composition 0.05 mg/mL White Light

| White Light 1.2 million Lux-hours | | | | Label Claim | | Desmopressin Actual Conc. | |
|---|---|---|---|---|---|---|---|
| | Retention | | | (mg/mL) | 0.050 | (mg/mL) | 0.04755 |
| Impurities | Time | RRT | RRF | Area | % Area | % Impurity | Results |
| RRT~0.520 | 14.012 | 0.520 | 1.00 | 1665 | 0.02 | 0.023 | 0.02 |
| Unknown~0.668 | 18.048 | 0.670 | 1.00 | 2242 | 0.03 | 0.031 | 0.03 |
| Unknown~0.826 | 22.242 | 0.825 | 1.00 | 3180 | 0.04 | 0.045 | 0.04 |
| Unknown~0.872 | 23.470 | 0.871 | 1.00 | 10750 | 0.15 | 0.151 | 0.15 |
| RRT~0.895 | 24.130 | 0.895 | 1.00 | 1963 | 0.03 | 0.027 | 0.03 |
| RRT~0.916 | 24.702 | 0.916 | 1.00 | 5381 | 0.08 | 0.075 | 0.08 |
| Glu-4/Imp 4 | 24.968 | 0.926 | 1.00 | 3683 | 0.05 | 0.052 | 0.05 |
| Asp5/Imp 7 | 25.397 | 0.942 | 1.00 | 3852 | 0.05 | 0.054 | 0.05 |
| Gly9OH/Imp 2 | 25.718 | 0.954 | 1.00 | 3668 | 0.05 | 0.051 | 0.05 |
| L-Arg8 | 26.497 | 0.983 | 1.00 | 4043 | 0.06 | 0.057 | 0.06 |
| Desmopressin | 26.956 | 1.000 | 1.00 | 7101398 | 99.26 | 99.456 | 99.46 |
| Gln6(ACM) | 27.975 | 1.038 | 1.00 | 5766 | 0.08 | 0.081 | 0.08 |
| ASn5(ACM) | 28.211 | 1.047 | 1.00 | 1036 | 0.01 | 0.015 | 0.01 |

TABLE B-6-continued

Forced Degradation under White Light for Batch No.: RB0317-8A
RB0317-8A Desmopressin Composition 0.05 mg/mL White Light

| | White Light 1.2 million Lux-hours | | | Label Claim | | Desmopressin Actual Conc. | | |
|---|---|---|---|---|---|---|---|---|
| Impurities | Retention Time | RRT | RRF | (mg/mL) Area | 0.050 % Area | (mg/mL) % Impurity | 0.04755 Results |
| Gly9-NMe2 | 28.723 | 1.066 | 1.00 | 1585 | 0.02 | 0.022 | 0.02 |
| Unknown~1.096 | 29.540 | 1.096 | 1.00 | 4210 | 0.06 | 0.059 | 0.06 |
| Total (%) | | | | 7154422 | 100.0 | Mass Balance | 100.19 |

TABLE B-7

Forced Degradation under UV for Batch No.: RB0317-8A
RB0317-8A Desmopressin Composition 0.05 mg/mL UV

| | UV 200 Watts Hours per sq meter | | | Label Claim | | Desmopressin Actual Conc. | |
|---|---|---|---|---|---|---|---|
| Impurities | Retention Time | RRT | RRF | (mg/mL) Area | 0.050 % Area | (mg/mL) % Impurity | 0.04755 Results |
| RRT~0.518 | 13.967 | 0.518 | 1.00 | 2726 | 0.04 | 0.038 | 0.04 |
| Unknown~0.667 | 17.997 | 0.667 | 1.00 | 1713 | 0.02 | 0.024 | 0.02 |
| Placebo~0.715 | 19.270 | 0.715 | 1.00 | 1801 | 0.03 | 0.025 | 0.03 |
| Unknown~0.824 | 22.224 | 0.824 | 1.00 | 5344 | 0.07 | 0.075 | 0.07 |
| Unknown~0.871 | 23.478 | 0.871 | 1.00 | 10757 | 0.15 | 0.151 | 0.15 |
| RRT~0.894 | 24.116 | 0.894 | 1.00 | 3914 | 0.05 | 0.055 | 0.05 |
| RRT~0.915 | 24.684 | 0.915 | 1.00 | 11301 | 0.16 | 0.158 | 0.16 |
| Gly9_Imp_2 | 24.960 | 0.926 | 1.00 | 3839 | 0.05 | 0.054 | 0.05 |
| Asp5_Imp 7 | 25.366 | 0.941 | 1.00 | 3769 | 0.05 | 0.053 | 0.05 |
| Glu4_Imp 4 | 25.737 | 0.954 | 1.00 | 2411 | 0.03 | 0.034 | 0.03 |
| L-Arg8 | 26.482 | 0.982 | 1.00 | 3589 | 0.05 | 0.050 | 0.05 |
| Desmopressin | 26.965 | 1.000 | 1.00 | 7081049 | 98.92 | 99.171 | 99.17 |
| ASn5(ACM) | 27.830 | 1.032 | 1.00 | 1104 | 0.02 | 0.015 | 0.02 |
| Gln6(ACM) | 27.991 | 1.038 | 1.00 | 4714 | 0.07 | 0.066 | 0.07 |
| Unknown | 28.173 | 1.045 | 1.00 | 2618 | 0.04 | 0.037 | 0.04 |
| Gly9-NMe2 | 28.730 | 1.065 | 1.00 | 3695 | 0.05 | 0.052 | 0.05 |
| Unknown~1.099 | 29.630 | 1.099 | 1.00 | 6319 | 0.09 | 0.088 | 0.09 |
| Placebo~1.155 | 31.155 | 1.155 | 1.00 | 1026 | 0.01 | 0.014 | 0.01 |
| RRT~1.199 | 32.343 | 1.199 | 1.00 | 1084 | 0.02 | 0.015 | 0.02 |
| RRT~1.231 | 33.196 | 1.231 | 1.00 | 2060 | 0.03 | 0.029 | 0.03 |
| RRT~1.306 | 35.203 | 1.306 | 1.00 | 1606 | 0.02 | 0.022 | 0.02 |
| RRT~1.323 | 35.688 | 1.323 | 1.00 | 1809 | 0.03 | 0.025 | 0.03 |
| Total (%) | | | | 7158248 | 100.0 | Mass Balance | 100.25 |

The effect of pH on stability was evaluated. Batches RB0317-13A to RB0317-13G were prepared with the same ingredients as Composition K (Batch No.: RB0317-8A) except that the amount of sodium benzoate was adjusted to achieve a specific pH, which falls within the range from about 3.5 to about 7.0, for each batch respectively. Batches RB0317-13A to RB0317-13G were tested for assay and impurity when placed for stability testing. The specific pH for each batch and the results of assay and impurity testing after stored at 60° C. for 4 days are summarized in Table B-8.

TABLE B-8 pH Stability Data for Batch Nos.: RB0317-13A to RB0317-13G

| Batch Nos: | pH | Assay (%) | Total Imp (%) | Imp 7 $Asp^5$ (%) | Imp 2 $Gly^9OH$ (%) | Imp 4 $Glu^4$ (%) | Imp 5 L-$Arg^8$ (%) | Imp 3 $Gln^4(ACM)$ (%) | Imp 6 $Asn^5(ACM)$ (%) | Imp 1 [Gly9N(CH3)2] (%) |
|---|---|---|---|---|---|---|---|---|---|---|
| RB0317-13A | 3.52 | 101.2 | 0.18 | ND | ND | 0.05 | 0.06 | 0.07 | ND | ND |
| 4 d/60° C. | | 100.1 | 2.28 | 0.03 | 0.72 | 0.88 | 0.06 | 0.06 | ND | ND |
| RB0317-13B | 4.0 | 101.2 | 0.12 | ND | ND | ND | 0.05 | 0.07 | ND | ND |
| 4 d/60° C. | | 100.7 | 0.99 | 0.17 | 0.24 | 0.28 | 0.06 | 0.07 | ND | ND |
| RB0317-8B | 4.5 | 104.0 | 0.28 | 0.02 | 0.03 | 0.06 | 0.05 | 0.07 | ND | ND |

TABLE B-8-continued pH Stability Data for Batch Nos.: RB0317-13A to RB0317-13G

| Batch Nos: | pH | Assay (%) | Total Imp (%) | Imp 7 Asp⁵ (%) | Imp 2 Gly⁹OH (%) | Imp 4 Glu⁴ (%) | Imp 5 L-Arg⁸ (%) | Imp 3 Gln⁴(ACM) (%) | Imp 6 Asn⁵(ACM) (%) | Imp 1 [Gly9N(CH3)2] (%) |
|---|---|---|---|---|---|---|---|---|---|---|
| 4 d/60° C. | | 103.6 | 0.72 | 0.11 | 0.12 | 0.15 | 0.05 | 0.01 | 0.03 | 0.02 |
| RB0317-13C | 5.0 | 101.2 | 0.19 | ND | ND | 0.06 | 0.06 | 0.07 | ND | ND |
| 4 d/60° C. | | 101.6 | 0.72 | 0.22 | 0.10 | 0.09 | 0.06 | 0.07 | ND | ND |
| RB0317-13D | 5.25 | 101.4 | 0.20 | ND | ND | 0.07 | 0.06 | 0.07 | ND | ND |
| 4 d/60° C. | | 101.8 | 0.66 | 0.22 | 0.07 | 0.07 | 0.07 | 0.07 | ND | ND |
| RB0317-13E | 5.5 | 100.4 | 0.19 | ND | ND | 0.07 | 0.06 | 0.06 | ND | ND |
| 4 d/60° C. | | 100.2 | 0.66 | 0.24 | 0.07 | 0.06 | 0.07 | 0.06 | ND | ND |
| RB0317-13F | 6.0 | 101.8 | 0.31 | ND | ND | 0.07 | 0.07 | 0.07 | ND | ND |
| 4 d/60° C. | | 101.4 | 0.71 | 0.26 | ND | 0.05 | 0.08 | 0.06 | ND | ND |
| RB0317-13G | 7.0 | 106.0 | 1.19 | ND | ND | ND | 0.22 | 0.05 | ND | ND |
| 4 d/60° C. | | 102.3 | 2.87 | 0.82 | 0.39 | 0.08 | 0.25 | 0.06 | ND | 0.06 |

ND = not detected

The results of impurity testing for batches RB0317-11A and RB0317-21A after stored at 60° C. for 4 days and/or after stored at about 40° C./75% RH for 1 month are summarized in Table B-9.

TABLE B-9

Impurity Data for Batch Nos.: RB0317-11A and RB0317-21A

| Batch# | Total Imp (%) | Imp 7 Asp⁵ (%) | Imp 2 Gly⁹OH (%) | Imp 4 Glu⁴ (%) | Imp 5 L-Arg⁸ (%) | Imp 3 Gln⁴(ACM) (%) | Imp 6 Asn⁵(ACM) (%) | Imp 1 [Gly9N(CH3)2] (%) |
|---|---|---|---|---|---|---|---|---|
| RB0317-11A (initial) | 0.13 | ND | ND | ND | 0.06 | 0.07 | ND | ND |
| RB0317-11A, 4 d/60° C. | 0.44 | 0.18 | 0.06 | 0.08 | 0.06 | 0.06 | ND | ND |
| RB0317-11A, 1 m-40° C. /75% RH | 0.54 | 0.18 | 0.09 | 0.09 | 0.05 | ND | 0.05 | ND |
| RB0317-21A (initial) | 0.27 | ND | ND | 0.07 | 0.06 | 0.10 | 0.04 | ND |
| RB0317-21A,1 m-40° C./75% RH | 0.53 | 0.12 | 0.05 | 0.06 | 0.04 | 0.08 | 0.02 | ND |

ND = not detected

Desmopressin composition Batch No.: RB0317-47B, as shown in Composition L in Table A-1, was tested for assay and impurity when placed for stability testing at about 25° C. and about 60 RH and at about 40° C. and about 75% RH. The testing results of initial, 3 months, and 6 months stability under both conditions are summarized in Table B-10.

TABLE B-10

Stability Data for Batch No.: RB0317-47B

| Batch No.: RB0317-47B | Assay, % | pH | Total Impurities, % | Gly9OH | Asp⁵ | Glu⁴ | L-Arg⁸ | Gln⁴ (ACM) | Asn⁵ (ACM) |
|---|---|---|---|---|---|---|---|---|---|
| Initial | 96.1 | 5.00 | 0.16 | ND | 0.05 | 0.06 | ND | ND | ND |
| 3 m-25/60 | 96.7 | 4.98 | 0.13 | BLOQ | BLOQ | BLOQ | ND | 0.06 | ND |
| 6 m-25/60 | 93.0 | 4.99 | 0.50 | 0.06 | 0.03 | 0.09 | ND | ND | 0.07 |
| 3 m-40/75 | 95.4 | 5.00 | 1.32 | 0.19 | 0.15 | 0.30 | ND | 0.03 | ND |
| 6 m-40/75 | 90.5 | 5.00 | 2.36 | 0.32 | 0.23 | 0.43 | 0.03 | ND | 0.05 |

ND = not detected,
BLOQ = Below the Limit of Quantification

Example C—Exemplary Manufacturing Process

Exemplary procedures of making a formulation of the disclosure are provided as follows.

Weigh a desirable amount of sodium benzoate NF, benzoic acid USP and desmopressin acetate USP, purified water USP Weight and record the tare weight of a compounding container and lid and add purified water USP Add benzoic acid and sodium benzoate to the compounding container, mix until dissolved Add desmopressin acetate to the compounding container, mix till dissolved Add purified water to the compounding container to make up the desired volume Filter into a storage container and package into desirable packaging materials During this process, bulk solution is collected for calculating yield and reconciliation and in-process samples are also collected for quality control testing.

Example D—Calculation of Buffer Capacity of 0.016% w/v (0.013M) Benzoic Acid/Benzoate Buffer at pH 4.5, 5.0 and 5.5

Buffer capacity is defined as the number of moles of acid or base that must be added to one liter of the buffer solution (in this case the composition of the present disclosure) to decrease or increase the pH by one unit. This value can be determined experimentally, or by calculation. The buffer capacity will depend on the specific buffer system (i.e., the pKa of the buffer), the buffer concentration and the initial pH of the buffer.

Calculation of Buffer Capacity of 0.016% w/v (0.013M) Benzoic Acid/Benzoate Buffer at pH 5.0

The pKa of benzoic acid is 4.2. Thus, the ratio of benzoate anion to benzoic acid for the buffer system is 6.3:1 at pH 5.0. For a buffer system at this pH having a total benzoate species (benzoic acid plus benzoate anion) concentration of 0.013M, these yields concentrations of benzoate anion=0.0112M and benzoic acid=0.0018M.

At an acidic pH shift of one unit (i.e., to pH 4.0), the ratio of benzoate anion to benzoic acid for the buffer system is 0.63:1, and the concentration of benzoate acid=0.008M and benzoic anion=0.005M. Thus, the concentration of benzoate anion changed from 0.0112M at pH 5.0 to 0.005M at pH 4.0. This requires 0.0062 moles of acid to effect this change. Accordingly, the buffer capacity of the original 0.013M benzoic acid/benzoate buffer solution at pH 5.0 is 0.0062.

A parallel calculation for a basic pH shift from pH 5.0 to pH 6.0 will yield a buffer capacity of 0.0016. This makes sense, as the addition of base to the buffer at pH 5.0 moves the pH of the solution further away from its optimal buffering pH (i.e., its pKa of 4.2). As used herein, the buffer capacity of the compositions of the present disclosure refer to the number of moles of acid or base that must be added to one liter of the composition of the present disclosure to decrease or increase the pH by one unit in the direction of the pKa of the buffer.

It can also be seen from the definition of buffer capacity above that the buffer capacity is directly dependent on the concentration of the buffer, because the number of moles required to provide a given pH shift will be directly proportional to the number of moles of buffer molecules present. Thus, the buffer capacity of a 0.32% w/v, (0.026M) benzoic acid/benzoate buffer solution at pH 5.0 would be 0.0124, and the buffer capacity of a 0.08% w/v (0.0065M) benzoic acid/benzoate buffer solution at pH 5.0 would be 0.0031.

Calculations for the benzoic acid/benzoate buffer systems pH 4.5, 5.0 and 5.5 are shown below in Table D.

TABLE D

Buffer capacity of benzoic acid/benzoate buffer systems pH 4.5, 5.0 and 5.5

| pH | Total Benzoic acid/Benzoate % w/v; (M) | Buffer Capacity |
| --- | --- | --- |
| 4.5 | 0.08 (0.0065M) | 0.0032 |
| 4.5 | 0.16 (0.013M) | 0.0065 |
| 4.5 | 0.32 (0.026M) | 0.013 |
| 5.0 | 0.08 (0.0065M) | 0.0031 |
| 5.0 | 0.16 (0.013M) | 0.0062 |
| 5.0 | 0.32 (0.026M) | 0.0124 |
| 5.5 | 0.08 (0.0065M) | 0.0019 |
| 5.5 | 0.16 (0.013M) | 0.0037 |
| 5.5 | 0.32 (0.026M) | 0.0074 |

Thus, in some embodiments, the compositions of the present disclosure comprising a benzoic acid/benzoate buffer having a total benzoate species concentration from about 0.008% w/v to about 0.032% w/v, and a buffer capacity of at least about 0.001; or at least about 0.002; or at least about 0.003; or at least about 0.004; or at least about 0.005; or at least about 0.006; or at least about 0.007; or at least about 0.008; or at least about 0.009; or at least about 0.01; or from about 0.001 to about 0.02; or from about 0.001 to about 0.015; or from about 0.003 to about 0.015; or from about 0.003 to about 0.007; or from about 0.003 to about 0.008; or about any of the values listed in Table D above.

Example E—Additional Formulations

Additional desmopressin acetate compositions using various concentration of desmopressin acetate, buffers and preservatives, can be prepared according to formulations in Tables E-1 to E-6 using the processes described in Examples A and C.

TABLE E-1

Additional Desmopressin Formulations

| Ingredient | Quantity % w/v (batch size: 100 mL) | | | | | |
| --- | --- | --- | --- | --- | --- | --- |
| | F-1 | F-2 | F-3 | F-4 | F-5 | F-6 |
| Water (initial amount) | 90 | 90 | 90 | 90 | 90 | 90 |
| Desmopressin Acetate | 0.005 | 0.005 | 0.005 | 0.005 | 0.005 | 0.005 |

TABLE E-1-continued

Additional Desmopressin Formulations

| Ingredient | | | | | | |
|---|---|---|---|---|---|---|
| API Strength (mg/mL) | 0.05 mg/mL | 0.05 mg/mL | 0.05 mg/mL | 0.05 mg/mL | 0.05 mg/mL | 0.05 mg/mL |
| Benzoic Acid | 0.022 | 0.025 | 0.03 | 0.032 | 0.037 | 0.04 |
| Sodium Benzoate | 0.18194 | 0.20675 | 0.2481 | 0.26464 | 0.30599 | 0.3308 |
| Parabens | Methyl-paraben, Propyl-paraben, or mixtures thereof: 0-0.5 | | | | | |
| pH | 4.7-5.0 | | | | | |
| Water | Qs to 100 mL | Qs to 100 mL | Qs to 100 mL | Qs to 100 mL | Qs to 100 mL | Qs to 100 mL |

| | Quantity % w/v (batch size: 100 mL) | | | | | |
|---|---|---|---|---|---|---|
| Ingredient | F-7 | F-8 | F-9 | F-10 | F-11 | F-12 |
| Water (initial amount) | 90 | 90 | 90 | 90 | 90 | 90 |
| Desmopressin Acetate | 0.005 | 0.005 | 0.005 | 0.005 | 0.005 | 0.005 |
| API Strength (mg/mL) | 0.05 mg/mL | 0.05 mg/mL | 0.05 mg/mL | 0.05 mg/mL | 0.05 mg/mL | 0.05 mg/mL |
| Benzoic Acid | 0.045 | 0.05 | 0.06 | 0.07 | 0.08 | 0.09 |
| Sodium Benzoate | 0.37215 | 0.4135 | 0.465 | 0.455 | 0.445 | 0.51 |
| Parabens | Methyl-paraben, Propyl-paraben, or mixtures thereof: 0-0.5 | | | | | |
| pH | 4.7-5.0 | | | | | |
| Water | Qs to 100 mL | Qs to 100 mL | Qs to 100 mL | Qs to 100 mL | Qs to 100 mL | Qs to 100 mL |

TABLE E-2

Additional Desmopressin Formulations

| | Quantity % w/v (batch size: 100 mL) | | | | | |
|---|---|---|---|---|---|---|
| Ingredient | F-13 | F-14 | F-15 | F-16 | F-17 | F-18 |
| Water (initial amount) | 90 | 90 | 90 | 90 | 90 | 90 |
| Desmopressin Acetate | 0.001 | 0.001 | 0.001 | 0.001 | 0.0025 | 0.0025 |
| API Strength (mg/mL) | 0.01 mg/mL | 0.01 mg/mL | 0.01 mg/mL | 0.01 mg/mL | 0.025 mg/mL | 0.025 mg/mL |
| Benzoic Acid | 0.03 | 0.0342 | 0.04 | 0.05 | 0.03 | 0.0342 |
| Sodium Benzoate | 0.2481 | 0.285 | 0.3308 | 0.4135 | 0.2481 | 0.285 |
| Parabens | Methyl-paraben, Propyl-paraben, or mixtures thereof: 0-0.5 | | | | | |
| pH | 5.0 | | | | | |
| Water | Qs to 100 mL | Qs to 100 mL | Qs to 100 mL | Qs to 100 mL | Qs to 100 mL | Qs to 100 mL |

| | Quantity % w/v (batch size: 100 mL) | | | | | |
|---|---|---|---|---|---|---|
| Ingredient | F-19 | F-20 | F-21 | F-22 | F-23 | F-24 |
| Water (initial amount) | 90 | 90 | 90 | 90 | 90 | 90 |
| Desmopressin Acetate | 0.0025 | 0.0025 | 0.01 | 0.01 | 0.01 | 0.01 |
| API Strength (mg/mL) | 0.025 mg/mL | 0.02 5 mg/mL | 0.01 mg/mL | 0.01 mg/mL | 0.01 mg/mL | 0.01 mg/mL |
| Benzoic Acid | 0.04 | 0.05 | 0.03 | 0.0342 | 0.04 | 0.05 |
| Sodium Benzoate | 0.3308 | 0.4135 | 0.2481 | 0.285 | 0.3308 | 0.4135 |
| Parabens | Methyl-paraben, Propyl-paraben, or mixtures thereof: 0-0.5 | | | | | |
| pH | 5.0 | | | | | |
| Water | Qs to 100 mL | Qs to 100 mL | Qs to 100 mL | Qs to 100 mL | Qs to 100 mL | Qs to 100 mL |

TABLE E-3

Additional Desmopressin Formulations

| Ingredient | Quantity % w/v (batch size: 100 mL) | | | | | |
|---|---|---|---|---|---|---|
| | F-25 | F-26 | F-27 | F-28 | F-29 | F-30 |
| Water (initial amount) | 90 | 90 | 90 | 90 | 90 | 90 |
| Desmopressin Acetate | 0.001 | 0.001 | 0.001 | 0.001 | 0.005 | 0.005 |
| API Strength (mg/mL) | 0.01 mg/mL | 0.01 mg/mL | 0.01 mg/mL | 0.01 mg/mL | 0.01 mg/mL | 0.01 mg/mL |
| Potassium Sorbate | 0.025 | 0.04 | 0.05 | 0.075 | 0.025 | 0.04 |
| Sorbic acid | 0.009 | 0.015 | 0.019 | 0.028 | 0.009 | 0.015 |
| Parabens | Methyl-paraben, Propyl-paraben, or mixtures thereof: 0.1-1.0 | | | | | |
| pH | *Amount of sorbic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

| Ingredient | Quantity % w/v (batch size: 100 mL) | | | | | |
|---|---|---|---|---|---|---|
| | F-31 | F-32 | F-33 | F-34 | F-35 | F-36 |
| Water (initial amount) | 90 | 90 | 90 | 90 | 90 | 90 |
| Desmopressin Acetate | 0.005 | 0.005 | 0.01 | 0.01 | 0.01 | 0.01 |
| API Strength (mg/mL) | 0.01 mg/mL | 0.01 mg/mL | 0.01 mg/mL | 0.01 mg/mL | 0.01 mg/mL | 0.01 mg/mL |
| Potassium Sorbate | 0.05 | 0.075 | 0.025 | 0.04 | 0.05 | 0.075 |
| Sorbic acid | 0.019 | 0.028 | 0.009 | 0.015 | 0.019 | 0.028 |
| Parabens | Methyl-paraben, Propyl-paraben, or mixtures thereof: 0.1-1.0 | | | | | |
| pH | *Amount of sorbic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

TABLE E-4

Additional Desmopressin Formulations

| Ingredient | Quantity % w/v (batch size: 100 mL) | | | | | |
|---|---|---|---|---|---|---|
| | F-25 | F-26 | F-27 | F-28 | F-29 | F-30 |
| Water (initial amount) | 90 | 90 | 90 | 90 | 90 | 90 |
| Desmopressin Acetate | 0.001 | 0.001 | 0.001 | 0.001 | 0.005 | 0.005 |
| API Strength (mg/mL) | 0.01 mg/mL | 0.01 mg/mL | 0.01 mg/mL | 0.01 mg/mL | 0.05 mg/mL | 0.05 mg/mL |
| Propionate | 0.05 | 0.1 | 0.2 | 0.25 | 0.05 | 0.1 |
| Propionic acid * | 0.03 | 0.07 | 0.13 | 0.17 | 0.03 | 0.07 |
| Parabens | Methyl-paraben, Propyl-paraben, or mixtures thereof: 0.1-1.0 | | | | | |
| pH | *Amount of propionic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

| Ingredient | Quantity % w/v (batch size: 100 mL) | | | | | |
|---|---|---|---|---|---|---|
| | F-31 | F-32 | F-33 | F-34 | F-35 | F-36 |
| Water (initial amount) | 90 | 90 | 90 | 90 | 90 | 90 |
| Desmopressin Acetate | 0.005 | 0.005 | 0.01 | 0.01 | 0.01 | 0.01 |

TABLE E-4-continued

Additional Desmopressin Formulations

| | | | | | | |
|---|---|---|---|---|---|---|
| API Strength (mg/mL) | 0.05 mg/mL | 0.05 mg/mL | 0.1 mg/mL | 0.1 mg/mL | 0.1 mg/mL | 0.1 mg/mL |
| Propionate | 0.2 | 0.25 | 0.05 | 0.1 | 0.2 | 0.25 |
| Propionic acid * | 0.13 | 0.17 | 0.03 | 0.07 | 0.13 | 0.17 |
| Parabens | Methyl-paraben, Propyl-paraben, or mixtures thereof: 0.1-1.0 | | | | | |
| pH | *Amount of propionic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

TABLE E-5

Additional Desmopressin Formulations

| | Quantity % w/v (batch size: 100 mL) | | | | | |
|---|---|---|---|---|---|---|
| Ingredient | F-25 | F-26 | F-27 | F-28 | F-29 | F-30 |
| Water (initial amount) | 90 | 90 | 90 | 90 | 90 | 90 |
| Desmopressin Acetate | 0.001 | 0.001 | 0.001 | 0.001 | 0.005 | 0.005 |
| API Strength (mg/mL) | 0.01 mg/mL | 0.01 mg/mL | 0.01 mg/mL | 0.01 mg/mL | 0.05 mg/mL | 0.05 mg/mL |
| Sodium acetate | 0.05 | 0.1 | 0.2 | 0.3 | 0.05 | 0.1 |
| Acetic acid * | 0.02 | 0.04 | 0.08 | 0.11 | 0.02 | 0.04 |
| Parabens | Methyl-paraben, Propyl-paraben, or mixtures thereof: 0.1-1.0 | | | | | |
| pH | *Amount of acetic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

| | Quantity % w/v (batch size: 100 mL) | | | | | |
|---|---|---|---|---|---|---|
| Ingredient | F-31 | F-32 | F-33 | F-34 | F-35 | F-36 |
| Water (initial amount) | 90 | 90 | 90 | 90 | 90 | 90 |
| Desmopressin Acetate | 0.005 | 0.005 | 0.01 | 0.01 | 0.01 | 0.01 |
| API Strength (mg/mL) | 0.05 mg/mL | 0.05 mg/mL | 0.1 mg/mL | 0.1 mg/mL | 0.1 mg/mL | 0.1 mg/mL |
| Sodium acetate | 0.2 | 0.3 | 0.05 | 0.1 | 0.2 | 0.3 |
| Acetic acid * | 0.08 | 0.11 | 0.02 | 0.04 | 0.08 | 0.11 |
| Parabens | Methyl-paraben, Propyl-paraben, or mixtures thereof: 0.1-1.0 | | | | | |
| pH | *Amount of acetic acid may vary to adjust pH to 4.5-5.0 | | | | | |
| Water | Qs to 100 mL | Qs to 100 mL | Qs to 100 mL | Qs to 100 mL | Qs to 100 mL | Qs to 100 mL |

TABLE E-6

Additional desmopressin oral compositions

| Ingredient | N | O | P | Q |
|---|---|---|---|---|
| Water (initial amount) | 900 mL | 900 mL | 900 mL | 900 mL |
| Benzoic Acid | 0.22 g | 0.22 g | 0.22 g | 0.22 g |
| Sodium Benzoate | 1.64 g | 1.64 g | 1.64 g | 1.64 g |
| Propylene Glycol | 0 | 0 | 5 | 5 |
| BHA | 0.02 g | 0.02 g | 0.02 g | 0.02 g |
| Desmopressin Acetate | 50 mg | 10 mg | 50 mg | 10 mg |
| Final volume (Water added) | Qs to 1000 mL | Qs to 1000 mL | Qs to 1000 mL | Qs to 1000 mL |

TABLE E-6-continued

Additional desmopressin oral compositions

| Ingredient | N | O | P | Q |
|---|---|---|---|---|
| Strength | 0.05 mg/mL | 0.01 mg/mL | 0.05 mg/mL | 0.01 mg/mL |
| pH | 5.0 | 5.0 | 5.0 | 5.0 |

Qs = Quantum satis, or sufficient quantity

The formulation stability such as assay and impurities of the desmopressin compositions described in Tables A-1 to A-8 and Tables E-1 to E-6 can be tested, for example, using any suitable HPLC methods, at different time points under various conditions, for example, after 1 month, 2 months, 3 months, 6 months, 12 months, 18 months, 24 months, 30 months, and/or 36 months of storage at refrigerated conditions, ambient conditions, accelerated conditions, and/or other conditions that simulate controlled room temperature. The desmopressin compositions are expected to retain about 90% w/w or greater of the initial amount of desmopressin free base or desmopressin acetate at the end of the stability testing schedule, such as at 24 months under ambient conditions. The desmopressin oral liquid compositions are expected to contain no more than 5% wt of total impurities and no more than 1% w/w of each of the peptide related impurities at the end of the stability testing schedule, such as at 24 months under ambient conditions.

Example F—Pilot Pharmacokinetics (PK) Study of Desmopressin Oral Solution

A comparative bioavailability study was conducted in healthy adult subjects to demonstrate the bioequivalence of DDAVP® desmopressin acetate tablet (0.2 mg, lot number #U12157E) and desmopressin oral solution having a composition as shown in Table A-8 (lot number #TB146B).

The study is an open label, balanced, randomized, single dose, two-treatment, two-sequence, two-period crossover comparative bioavailability study. A single oral dose of the reference product, desmopressin acetate tablet (0.2 mg×3 tablets) or a single oral dose of the test product, desmopressin oral solution 0.6 mg (12 ml×0.05 mg/ml) were administered to each subject in a random order as per randomization schedule in each of the two period of the study. The two periods were separated by a washout period. At the end of the study, each subject received a single oral dose of the reference product in one period and a single oral dose of the test product in the other period. A total of 18 healthy human adult subjects were involved in the study. Both the treatments were administered to the healthy human adult subjects under fasting condition. The plasma concentration of desmopressin acetate for each patient was measured after receiving a treatment and the mean plasma concentration versus time was plotted and shown in FIG. 1. Statistical analysis was performed according to the guidance entitled *Statistical Approaches to Establishing Bioequivalence*, issued by the U.S. Food & Drug Administration, Center for Drug Evaluation and Research. The approach of average bioequivalence was used, which involves the calculation of a 90% confidence interval for the ratio of the averages (population geometric means) of the measures for the Test and Reference products. To establish bioequivalence, the calculated confidence interval should generally fall within 80-125% for the ratio of the product averages. The statistical summary of the comparative bioavailability study results is shown in Table F-1. The results show that the DDAVP® desmopressin acetate tablet (0.2 mg, lot number #U12157E) and the desmopressin oral solution having a composition as shown in Table A-8 (lot number #TB146B) are bioequivalent.

TABLE F-1

Statistical Summary of the Comparative Bioavailability Study Results

| Parameter | Test Product | N | Reference Product | Ratio | 90% C.I. |
|---|---|---|---|---|---|
| $AUC_{0-t}$ (hr*pg/mL) | 243.788 | 18 | 256.445 | 95.06% | 84.04%-107.53% |
| $AUC_{0-\infty}$ (hr*pg/mL) | 256.167 | 18 | 270.362 | 94.75% | 83.75%-107.20% |
| $C_{max}$ (pg/mL) | 71.074 | 18 | 70.711 | 100.51% | 87.81%-115.06% |

Example G—Titration of Desmopressin Oral Solution

A pediatric patient suffering from a condition selected from diabetes insipidus, bedwetting, hemophilia A, von willebrand disease and high blood urea levels is administered with compositions in Tables A-1 to A-8 and Tables E-1 to E-6 at an amount equivalent to an initial dose of 0.05 mg desmopressin acetate, two times a day, using an oral syringe with graduated markings.

The patient is monitored for improvement of symptoms, and the dose is individually adjusted to their optimum therapeutic dose. There is no need for dilution or addition of any further components during the administration of the desmopressin oral liquid compositions, which is ready-to-use, with the adjusted dose.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

Numbered Embodiments

Embodiment 1. A liquid pharmaceutical composition comprising
  a) desmopressin free base or a pharmaceutically acceptable salt thereof in an amount of about 0.01 mg/mL to about 0.1 mg/mL;
  b) a two-component, dual-functional, preservative-buffer system; and
  c) water,
    wherein the liquid pharmaceutical composition is an oral solution, wherein the liquid pharmaceutical composition is stable after stored at room temperature for at least 2 months.

Embodiment 2. A liquid pharmaceutical composition comprising
a) desmopressin free base or a pharmaceutically acceptable salt thereof in an amount of about 0.01 mg/mL to about 0.1 mg/mL;
b) a buffer system in an amount of about 0.6% w/v or less; and
c) water,
wherein the liquid pharmaceutical composition is an oral solution,
wherein the buffer system also functions as a preservative;
wherein the liquid pharmaceutical composition is stable after stored at room temperature for at least 2 months.

Embodiment 3. The liquid pharmaceutical composition of embodiment 1 or 2, wherein desmopressin free base or a pharmaceutically acceptable salt thereof is present in an amount of about 0.01 mg/mL to about 0.08 mg/mL, about 0.03 mg/mL to about 0.07 mg/mL, or about 0.04 mg/mL to about 0.06 mg/mL.

Embodiment 4. The liquid pharmaceutical composition of any one of embodiments 1 to 3, wherein desmopressin free base or a pharmaceutically acceptable salt thereof is present in an amount of about 0.05 mg/mL.

Embodiment 5. The liquid pharmaceutical composition of any one of embodiments 1 to 4, wherein the pharmaceutically acceptable salt of desmopressin is desmopressin acetate.

Embodiment 6. The liquid pharmaceutical composition of embodiment 5, wherein desmopressin acetate is present in an amount of about 0.05 mg/mL.

Embodiment 7. The liquid pharmaceutical composition of any one of embodiments 1 or 3 to 6, wherein the two-component, dual-functional, preservative-buffer system comprises an acidic preservative and a salt of the acidic preservative, optionally a sodium salt or a potassium salt.

Embodiment 8. The liquid pharmaceutical composition of embodiment 7, wherein the acidic preservative and the salt of the acidic preservative are in a weight ratio of from about 1:50 to about 50:1, from about 1:40 to about 20:1, from about 1:30 to about 1:1, from about 1:20 to about 1:5, from about 1:15 to about 1:5, or from about 1:10 to about 1:6.

Embodiment 9. The liquid pharmaceutical composition of embodiment 7 or 8, wherein the two-component, dual-functional, preservative-buffer system is selected from sorbic acid/sorbate, benzoic acid/benzoate, propionic acid/propionate, citric acid/citrate, acetic acid/acetate, lactic acid/lactate, formic acid/formate, and ascorbic acid/ascorbate.

Embodiment 10. The liquid pharmaceutical composition of any one of embodiments 7 to 9, wherein the two-component, dual-functional, preservative-buffer system is sorbic acid/sorbate or benzoic acid/benzoate.

Embodiment 11. The liquid pharmaceutical composition of any one of embodiments 7 to 10, wherein two-component, dual-functional, preservative-buffer system is benzoic acid and sodium benzoate and optionally wherein benzoic acid and sodium benzoate are present in an amount of from about 0.01% w/v to about 0.6% w/v, about 0.01% w/v to about 0.5% w/v, about 0.05% w/v to about 0.45% w/v, about 0.08% w/v to about 0.4% w/v, about 0.1% w/v to about 0.35% w/v, about 0.15% w/v to about 0.32% w/v, or about 0.18% w/v to about 0.32% w/v.

Embodiment 12. The liquid pharmaceutical composition of any one of embodiments 7 to 11, wherein the two-component, dual-functional, preservative-buffer system is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.35% w/v or less, or about 0.32% w/v or less.

Embodiment 13. The liquid pharmaceutical composition of any one of embodiments 7 to 12, wherein the two-component, dual-functional, preservative-buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D.

Embodiment 14. The liquid pharmaceutical composition of embodiment 11, wherein benzoic acid and sodium benzoate are present in an amount of about 0.18% w/v to about 0.32% w/v and provide a pH that is from about 4.0 to about 6.0, about 4.5 to about 5.5, or about 5.0.

Embodiment 15. The liquid pharmaceutical composition of any one of embodiments 2 to 6, wherein the buffer system comprises an acid and its conjugate base, optionally wherein the acid is a weak acid.

Embodiment 16. The liquid pharmaceutical composition of embodiment 15, wherein the acid is an acidic preservative.

Embodiment 17. The liquid pharmaceutical composition of embodiment 15 or 16, wherein the buffer system comprises the acidic preservative and a salt of the acidic preservative, optionally a sodium salt or a potassium salt.

Embodiment 18. The liquid pharmaceutical composition of embodiment 17, wherein the buffer system comprises a combination of the acidic preservative and the salt of the acidic preservative in a weight ratio of from about 1:50 to about 1:1, from about 1:40 to about 1:1, from about 1:30 to about 1:4, from about 1:20 to about 1:5, from about 1:15 to about 1:5, or from about 1:10 to about 1:6, from about 1:6 to about 1:1, from about 1:3 to about 1:1, or from about 1:2 to about 1:1.

Embodiment 19. The liquid pharmaceutical composition of any one of embodiment 15 or 18, wherein the buffer system comprises sorbic acid, sorbate salts, benzoic acid, benzoate salts, propionic acid, propionate salts, citric acid, citrate salts, acetic acid, acetate salts, lactic acid, lactate salts, formic acid, formate salts, ascorbic acid, or ascorbate salts, or any combination thereof.

Embodiment 20. The liquid pharmaceutical composition of any one of embodiments 15 to 19, wherein the buffer system comprises benzoic acid, or a benzoate salt (optionally sodium benzoate), or a combination thereof.

Embodiment 21. The liquid pharmaceutical composition of embodiment 20, wherein the buffer system comprises benzoic acid and sodium benzoate, and optionally wherein benzoic acid and sodium benzoate are present in an amount of about 0.08% w/v to about 0.6% w/v, about 0.1% w/v to about 0.5% w/v, about 0.15% w/v to about 0.4% w/v, or about 0.16% w/v to about 0.32% w/v.

Embodiment 22. The liquid pharmaceutical composition of any one of embodiments 15 to 20, wherein the buffer system is present in an amount of about 0.6% w/v or less, about 0.5% w/v or less, about 0.4% w/v or less, or about 0.32% w/v or less.

Embodiment 23. The liquid pharmaceutical composition of any one of embodiments 15 to 22, wherein the buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D.

Embodiment 24. The liquid pharmaceutical composition of embodiment 21, wherein benzoic acid and sodium benzoate are present in an amount of about 0.18% w/v to about 0.32% w/v and provide a pH that is from about 4.0 to about 6.0, about 4.5 to about 5.5, or about 5.0.

Embodiment 25. A liquid pharmaceutical composition, comprising
a) desmopressin acetate;
b) sodium benzoate;
c) benzoic acid; and
d) water,
wherein the liquid pharmaceutical composition is an oral solution.

Embodiment 26. The liquid pharmaceutical composition of embodiment 25, comprising
a) desmopressin acetate in an amount of about 0.01 to about 0.1 mg/mL;
b) sodium benzoate in an amount of about 0.18% w/v to about 0.4% w/v;
c) benzoic acid in an amount of about 0.02% w/v to about 0.1% w/v; and
d) water.

Embodiment 27. The liquid pharmaceutical composition of embodiment 25 or 26, comprising
a) desmopressin acetate in an amount of about 0.025 to about 0.075 mg/mL;
b) sodium benzoate in an amount of about 0.2% w/v to about 0.35% w/v;
c) benzoic acid in an amount of about 0.03% w/v to about 0.04% w/v; and
d) water.

Embodiment 28. The liquid pharmaceutical composition of any one of the preceding embodiments, comprising
a) desmopressin acetate in an amount of about 0.05 mg/mL;
b) sodium benzoate in an amount of about 0.25% w/v to about 0.3% w/v;
c) benzoic acid in an amount of about 0.034% w/v; and
d) water.

Embodiment 29. The liquid pharmaceutical composition of any one of the preceding embodiments, comprising
a) desmopressin acetate in an amount of about 0.05 mg/mL;
b) sodium benzoate in an amount of about 0.285% w/v;
c) benzoic acid in an amount of about 0.034% w/v; and
d) water.

Embodiment 30. The liquid pharmaceutical composition of any one of the preceding embodiments, consisting essentially of
a) desmopressin acetate in an amount of about 0.05 mg/mL;
b) sodium benzoate in an amount of about 0.285% w/v;
c) benzoic acid in an amount of about 0.034% w/v; and
d) water.

Embodiment 31. The liquid pharmaceutical composition of any one of the preceding embodiments, consisting of
a) desmopressin acetate in an amount of about 0.05 mg/mL;
b) sodium benzoate in an amount of about 0.285% w/v;
c) benzoic acid in an amount of about 0.034% w/v; and
d) water.

Embodiment 32. The liquid pharmaceutical composition of any one of the preceding embodiments, wherein the liquid pharmaceutical composition is ready-to-use without dilution or addition of any further components to the liquid pharmaceutical composition.

Embodiment 33. A liquid pharmaceutical composition comprising
desmopressin free base or a pharmaceutically acceptable salt thereof in an amount of about 0.01 mg/mL to about 0.1 mg/mL,
wherein the liquid pharmaceutical composition is an oral solution that is ready-to-use without dilution or addition of any further components for administration in pediatric population,
wherein the liquid pharmaceutical composition does not comprise malic acid or malate, and
wherein the liquid pharmaceutical composition is stable after stored at room temperature for at least 2 months.

Embodiment 34. A liquid pharmaceutical composition comprising
desmopressin free base or a pharmaceutically acceptable salt thereof in an amount of about 0.01 mg/mL to about 0.1 mg/mL,
wherein the liquid pharmaceutical composition is an oral solution that is ready-to-use without dilution or addition of any further components for administration in pediatric population,
wherein the liquid pharmaceutical composition does not comprise a sweetener, and
wherein the liquid pharmaceutical composition is stable after stored at room temperature for at least 2 months.

Embodiment 35. The liquid pharmaceutical composition of any one of embodiments 25, 33 or 34, wherein desmopressin free base or a pharmaceutically acceptable salt thereof is present in an amount of about 0.01 mg/mL to about 0.08 mg/mL, about 0.03 mg/mL to about 0.07 mg/mL, or about 0.04 mg/mL to about 0.06 mg/mL.

Embodiment 36. The liquid pharmaceutical composition of any one of embodiments 25 or 33 to 35, wherein desmopressin free base or a pharmaceutically acceptable salt thereof is present in an amount of about 0.05 mg/mL.

Embodiment 37. The liquid pharmaceutical composition of any one of embodiments 25 or 33 to 35, wherein the pharmaceutically acceptable salt of desmopressin is desmopressin acetate.

Embodiment 38. The liquid pharmaceutical composition of embodiment 37, wherein desmopressin acetate is present in an amount of about 0.05 mg/mL.

Embodiment 39. The liquid pharmaceutical composition of any one of embodiments 25 or 33 to 38, wherein the liquid pharmaceutical composition comprises water and optionally further comprises a liquid carrier.

Embodiment 40. The liquid pharmaceutical composition of embodiment 39, wherein water is present in the liquid pharmaceutical composition in an amount of about 10% to about 99.9% w/v, about 20% to about 99.9% w/v, about 40% to about 99.9% w/v, about 60% to about 99.9% w/v, about 80% to about 99.9% w/v, about 90% to about 99.9% w/v, or about 95% to about 99.9% w/v.

Embodiment 41. The liquid pharmaceutical composition of embodiment 39, wherein the liquid carrier is aqueous.

Embodiment 42. The liquid pharmaceutical composition of embodiment 39, wherein the liquid carrier is non-aqueous.

Embodiment 43. The liquid pharmaceutical composition of embodiment 39, wherein the liquid pharmaceutical composition further comprises the liquid carrier and wherein the liquid carrier comprises polyethers, lower polyhydroxy alcohols, ethanol, propylene glycol, isosorbide dimethyl ether, di(ethylene glycol) ethyl ether, glycols, glycerin, polyethylene glycol (PEG), sugar alcohols (optionally sorbitol), or a combination thereof.

Embodiment 44. The liquid pharmaceutical composition of any one of embodiments 39 to 43, wherein the liquid carrier is present in an amount of from about 0.01% w/v to about 90% w/v, from about 1% w/v to about 80% w/v, from about 1% w/v to about 70% w/v, from about 1% w/v to about 60% w/v, from about 1% w/v to about 50% w/v, from about 1% w/v to about 40% w/v, from about 1% w/v to about 30% w/v, from about 1% w/v to about 20% w/v, from about 3% w/v to about 10% w/v, from about 3% w/v to about 7% w/v, or about 5% w/v.

Embodiment 45. The liquid pharmaceutical composition of any one of embodiments 39, 43, or 44, wherein the liquid carrier comprises propylene glycol, and optionally wherein propylene glycol is present in an amount of from about 3% w/v to about 10% w/v, from about 3% w/v to about 7% w/v, or about 5% w/v.

Embodiment 46. The liquid pharmaceutical composition of any one of embodiments 33 to 45, wherein the liquid pharmaceutical composition comprises a buffer system.

Embodiment 47. The liquid pharmaceutical composition of embodiment 46, wherein the buffer system comprises benzoic acid, benzoate, citric acid, citrate, acetic acid, acetate, sorbic acid, sorbate, propionic acid, propionate, carbonate, bicarbonate, glycine/glycine HCl, monobasic/dibasic phosphate, tartaric acid, tartrate, fumaric acid, ascorbic acid, ascorbate, formic acid, formate, phosphoric acid, phosphate, lactic acid, lactate, gluconates, aspartic acid, aspartate, glutamic acid, glutamate, maleic acid, maleate, succinic acid, or succinate, or a combination thereof.

Embodiment 48. The liquid pharmaceutical composition of embodiment 46 or 47, wherein the buffer system comprises benzoic acid, a benzoate salt (optionally sodium benzoate), or a combination thereof.

Embodiment 49. The liquid pharmaceutical composition of embodiment 48, wherein the buffer system comprises benzoic acid and sodium benzoate, and optionally wherein benzoic acid and sodium benzoate are present in an amount of from 0.01% w/v to about 0.6% w/v, about 0.08% w/v to about 0.4% w/v, about 0.1% w/v to about 0.4% w/v, about 0.15% w/v to about 0.35% w/v, or about 0.16% w/v to about 0.32% w/v.

Embodiment 50. The liquid pharmaceutical composition of any one of embodiments 46 to 48, about 0.9% w/v or less, about 0.8% w/v or less, about 0.7% w/v or less, about 0.6% w/v or less, about 0.5% w/v or less, about 0.4% w/v or less, about 0.35% w/v or less, or about 0.32% w/v or less.

Embodiment 51. The liquid pharmaceutical composition of any one of embodiments 46 to 50, wherein the buffer system provides a buffering capacity of at least about 0.001, at least about 0.002, at least about 0.003, at least about 0.004, at least about 0.005, at least about 0.006, at least about 0.007, at least about 0.008, at least about 0.009, at least about 0.01, from about 0.001 to about 0.02, from about 0.001 to about 0.015, from about 0.003 to about 0.015, from about 0.003 to about 0.01, from about 0.003 to about 0.008, from about 0.005 to about 0.008, from about 0.006 to about 0.008, or about any of the values listed in Table D.

Embodiment 52. The liquid pharmaceutical composition of any one of embodiments 11, 21, 25 or 49, wherein benzoic acid is present in an amount of from about 0.005% w/v to about 0.1% w/v, about 0.01% w/v to about 0.08% w/v, about 0.015% w/v to about 0.07% w/v, about 0.015% w/v to about 0.06% w/v, about 0.02% w/v to about 0.05% w/v, about 0.03% w/v to about 0.04% w/v, or about 0.034% w/v.

Embodiment 53. The liquid pharmaceutical composition of any one of embodiments 11, 21, 25 or 49, wherein sodium benzoate is present in an amount of from about 0.01% w/v to about 0.6% w/v, about 0.01% w/v to about 0.5% w/v, about 0.05% w/v to about 0.45% w/v, about 0.08% w/v to about 0.4% w/v, about 0.1% w/v to about 0.35% w/v, about 0.15% w/v to about 0.32% w/v, about 0.18% w/v to about 0.32% w/v, about 0.25% w/v to about 0.3% w/v, or about 0.285% w/v.

Embodiment 54. The liquid pharmaceutical composition of any one of embodiments 25 to 27 or 49, wherein benzoic acid and sodium benzoate are present in an amount of from about 0.25% w/v to about 0.35% w/v, about 0.28% w/v to about 0.33% w/v, or about 0.32% w/v, and provide a pH that is from about 4.0 to about 6.0, about 4.5 to about 5.5, or about 5.0.

Embodiment 55. The liquid pharmaceutical composition of any one of embodiments 25 to 29 or 33 to 54, wherein the liquid pharmaceutical composition comprises a preservative.

Embodiment 56. The liquid pharmaceutical composition of embodiment 55, wherein the preservative comprises an antimicrobial agent, a chelating agent, an antioxidant, or a combination thereof.

Embodiment 57. The liquid pharmaceutical composition of embodiment 55 or 56, wherein the preservative comprises a paraben or a mixture of parabens, benzoic acid or a pharmaceutically acceptable salt thereof, sorbic acid or a pharmaceutically acceptable salt thereof, phenoxyethanol, benzyl alcohol, propionic acid, or a combination thereof.

Embodiment 58. The liquid pharmaceutical composition of embodiment 57, wherein paraben or the mixture of parabens comprises methyl paraben, ethyl paraben, or propyl paraben, or a combination thereof.

Embodiment 59. The liquid pharmaceutical composition of embodiment 57 or 58, wherein the mixture of parabens is present in an amount of from about 0.01% to about 0.5% w/v, from about 0.15 to about 0.25% w/v, or about 0.2% w/v.

Embodiment 60. The liquid pharmaceutical composition of embodiment 55 or 56, wherein the preservative comprises disodium ethylenediaminetetraacetic acid, polyphosphates, citric acid, calcium disodium edetate, ethylenediaminetetraacetic acid (EDTA), or a combination thereof.

Embodiment 61. The liquid pharmaceutical composition of embodiment 60, wherein EDTA is present in an amount of from about 0.01% to about 0.5% w/v, from about 0.05% to about 0.2% w/v, or about 0.1% w/v.

Embodiment 62. The liquid pharmaceutical composition of embodiment 55 or 56, wherein the preservative comprises an antioxidant, optionally wherein the antioxidant comprises vitamin A, monothioglycerol, ascorbic acid, sodium bisulfite, sodium sulfite, α-Tocopherol acetate (vitamin E), butylated hydroxyanisole (BHA), butylated hydroxytoluene (BHT), propyl gallate, vitamin E, hydroquinone, hydroxycoumarins, ethanolamine, lecithin, cephalin, ascorbic acid, sorbitol, phosphoric acid, bisulfite, sodium metabisulfite, thiodipropionic acid and its esters, or dithiocarbamates or a combination thereof.

Embodiment 63. The liquid pharmaceutical composition of embodiment 62, wherein the antioxidant comprises BHA, BHT, or any combination thereof, and optionally wherein the antioxidant is present in an amount of from about 0.001% to about 0.1% w/v, or about 0.01% w/v.

Embodiment 64. The liquid pharmaceutical composition of embodiment 55 or 56, wherein the preservative comprises benzyl alcohol, benzoic acid, sorbic acid, sodium benzoate, sodium sorbate, EDTA and its salts, parabens (such as methylparaben, ethylparaben, propylparaben, butylparaben and their salts), potassium sorbate, antibacterial agents such as halogenated diphenyl ether (optionally triclosan), herbal extracts and essential oils (optionally rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (optionally chlorhexidine, alexidine or octenidine), quaternary ammonium compounds (optionally cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, phthalic acid, monoperthalic acid and its esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, or any combination thereof.

Embodiment 65. The liquid pharmaceutical composition of embodiment 55 or 56, wherein the preservative comprises benzoic acid, or sodium benzoate, or a combination thereof.

Embodiment 66. The liquid pharmaceutical composition of any one of embodiments 55 to 57, 60, 62, 64, or 65, wherein the preservative is present in an amount of about 1% w/v or less, about 0.9% w/v or less, about 0.8% w/v or less, about 0.7% w/v or less, about 0.6% w/v or less, about 0.5% w/v or less, about 0.4% w/v or less, about 0.32% w/v or less, about 0.3% w/v or less, or about 0.2% w/v or less.

Embodiment 67. The liquid pharmaceutical composition of any one of embodiments 25 to 29 or 33 to 66, wherein the liquid pharmaceutical composition further comprises a flavoring agent.

Embodiment 68. The liquid pharmaceutical composition of embodiment 67, wherein the liquid pharmaceutical composition further comprises a flavoring agent and wherein the flavoring agent comprises a natural flavoring agent, an artificial flavoring agent, or a combination thereof.

Embodiment 69. The liquid pharmaceutical composition of embodiment 68, wherein the flavoring agent comprises 4-hydroxy-3-methoxybenzaldehyde, methyl anthranilate, 3,5-dimethyl-1,2-cyclopentadione, maltol, 4-(4-hydroxyphenyl)butan-2-one, ethyl maltol, or ethyl propionate.

Embodiment 70. The liquid pharmaceutical composition of any one of embodiments 25 to 29, 33, or 35 to 69, wherein the pharmaceutical composition further comprises a sweetener.

Embodiment 71. The liquid pharmaceutical composition of embodiment 70, wherein the sweetener is a sugar (e.g., glucose, fructose, sucrose, lactose, maltose) or sugar alcohol (e.g., xylitol, mannitol, lactitol, maltitol, or sorbitol).

Embodiment 72. The liquid pharmaceutical composition of embodiment 70, wherein the sweetener comprises glucose, fructose, sucrose, xylitol, tagatose, sucralose, maltitol, isomaltulose, hydrogenated isomaltulose, lactitol, sorbitol, erythritol, trehalose, maltodextrin, or polydextrose.

Embodiment 73. The liquid pharmaceutical composition of embodiment 70, wherein the sweetener comprises sorbitol or maltitol, or a combination thereof.

Embodiment 74. The liquid pharmaceutical composition of any one of embodiments 1 to 73, wherein the liquid pharmaceutical composition has a pH of from about 3.5 to about 6.0, about 4.0 to about 6.0, about 4.5 to about 5.5, about 4.75 to about 5.25, or about 5.0.

Embodiment 75. The liquid pharmaceutical composition of embodiment 74, wherein the liquid pharmaceutical composition has a pH of about 5.0.

Embodiment 76. The liquid pharmaceutical composition of any one of embodiments 1 to 75, wherein the liquid pharmaceutical composition contains no more than 5% wt of total impurities and not more than 1% wt of each of the following impurities: [Asp$^5$]desmopressin, [Glu$^4$]desmopressin, [Gly$^9$OH]desmopressin, [L-Arg$^8$] desmopressin, [Gln$^4$(Acm)]desmopressin, [Asn$^5$(Acm)]desmopressin, [Gly$^9$N(CH$_3$)$_2$]desmopressin, after stored at about 2° C. to about 8° C. for 3, 6, 9, 12, 18, 24, 30, or 36 months, after stored at room temperature for 3, 6, 9, 12, 18, or 24 months, and/or after stored at about 40° C.±2° C. for 1, 2, 3, or 6 months.

Embodiment 77. The liquid pharmaceutical composition of any one of embodiments 1 to 76, wherein the liquid pharmaceutical composition retains at least 90% wt of the initial desmopressin acetate amount after stored at about 2° C. to about 8° C. for 3, 6, 9, 12, 18, 24, 30, or 36 months, after stored at room temperature for 3, 6, 9, 12, 18, or 24 months, and/or after stored at about 40° C.±2° C. for 1, 2, 3, or 6 months.

Embodiment 78. The liquid pharmaceutical composition of any one of embodiments 76 to 77, wherein the amount of desmopressin acetate and impurities are determined according to High-performance liquid chromatography (HPLC) method.

Embodiment 79. The liquid pharmaceutical composition of any one of the preceding embodiments, wherein the liquid pharmaceutical composition remains stable after stored at about 2° C. to about 8° C. for at least 3, 6, 9, 12, 18, or 24 months, after stored at room temperature for at least 3, 6, 9, 12, 18, or 24 months, and/or after stored at about 40° C.±2° C. for at least 1, 2, 3, or 6 months.

Embodiment 80. The liquid pharmaceutical composition of any one of the preceding embodiments, wherein the liquid pharmaceutical composition exhibits a bioavailability that is bioequivalent to a reference pharmaceutical composition that comprises desmopressin acetate, when measured as the total area under the curve (AUC) after oral administration or when measured as $C_{max}$ after oral administration, optionally wherein the reference pharmaceutical composition is an oral tablet sold under the trade name DDAVP.

Embodiment 81. The liquid pharmaceutical composition of any one of the preceding embodiments, wherein the liquid pharmaceutical composition exhibits a bioavailability that is from 80% to 125% relative to a bioavailability of a reference pharmaceutical composition that comprises desmopressin acetate with a 90% confidence interval, when measured as the total area under the curve (AUC) after oral administration or when measured as $C_{max}$ after oral administration, optionally wherein the reference pharmaceutical composition is an oral tablet sold under the trade name DDAVP.

Embodiment 82. A direct dosing device comprising the liquid pharmaceutical composition of any one of embodiments 1 to 81.

Embodiment 83. The direct dosing device of embodiment 82, wherein the direct dosing device is a measuring device with graduations.

Embodiment 84. The direct dosing device of embodiment 82 or 83, wherein the direct dosing device is an oral syringe.

Embodiment 85. A method of treating a disease or condition, or symptoms thereof, comprising administering the liquid pharmaceutical composition of any one of embodiments 1 to 81 to a subject in need thereof.

Embodiment 86. The method of embodiment 85, wherein the liquid pharmaceutical composition is administered to the subject orally or through a nasogastric, jejunostomy, or gastrostomy tube.

Embodiment 87. The method of embodiment 85 or 86, wherein the disease or condition, or symptoms thereof is selected from diabetes insipidus, bedwetting, hemophilia A, von willebrand disease, polyurea, and high blood urea levels.

Embodiment 88. The method of embodiment 85 or 86, wherein the disease or condition, or symptoms thereof is selected from central diabetes insipidus, primary nocturnal enuresis, nocturia, polydipsia, nocturnal polyuria, hypothalamic injury-induced obesity (HIO), bleeding in subjects with Hemophilia A and/or with von Willebrand-Jurgens disease, and postoperative bleeding.

Embodiment 89. The method of any one of embodiments 85 to 88, wherein the liquid pharmaceutical composition is administered in a therapeutically effective amount.

Embodiment 90. The method of any one of embodiments 85 to 89, wherein the administered amount of desmopressin acetate is 90%-110%, 95%-105%, or 100% relative to a dose required for delivering a therapeutically relevant exposure of desmopressin acetate in the fasted state using an desmopressin acetate oral tablet formulation, optionally wherein the desmopressin acetate oral tablet formulation is sold under the trade name DDAVP.

Embodiment 91. The method of any one of embodiments 85 to 90, wherein the administration of the liquid pharmaceutical composition to the subject is made via the direct dosing device of any one of embodiments 82-84.

Embodiment 92. The method of any one of embodiments 85 to 91, wherein the administration of the liquid pharmaceutical composition to the subject does not involve dilution and/or addition of any further components to the liquid pharmaceutical composition.

Embodiment 93. A method for administering desmopressin free base or a pharmaceutically acceptable salt thereof to a subject in need thereof, the method comprising orally administering the liquid pharmaceutical composition of any one of embodiments 1 to 81 without dilution or addition of any further components to the liquid pharmaceutical composition.

Embodiment 94. The method of embodiment 93, wherein the administration of the liquid pharmaceutical composition to the subject is made via the direct dosing device of any one of embodiments 82 to 84.

Embodiment 95. The method of embodiment 93 or 94, wherein the method comprises a reduced risk of microbial contamination as compared to a method of orally administering a desmopressin composition that involves dilution and/or addition of any further components to such desmopressin composition prior to administration to the subject.

Embodiment 96. The method of embodiment 93 or 94, wherein the method comprises an increased accuracy of dosing as compared to a method of orally administering a desmopressin composition that involves dilution and/or addition of any further components to such desmopressin composition prior to administration to the subject.

Embodiment 97. The method of any one of embodiments 85 to 96, wherein the subject has an age of less than 18 years old.

Embodiment 98. A method of making the liquid pharmaceutical composition of any one of embodiments 1 to 81, wherein the method comprises mixing desmopressin free base or a pharmaceutically acceptable salt thereof with water, thereby forming a solution of desmopressin.

Embodiment 99. The method of embodiment 98 wherein the method comprises adding a buffer system or a two-component, dual-functional, preservative-buffer system into the solution of desmopressin.

Embodiment 100. The method of embodiment 98, wherein the buffer system or the two-component, dual-functional, preservative-buffer system is added to water before mixing desmopressin free base or a pharmaceutically acceptable salt thereof with water.

Embodiment 101. A kit comprising a package enclosing the liquid pharmaceutical composition of any one of embodiments 1 to 81 or the direct dosing device of any one of embodiments 82 to 84.

Embodiment 102. The kit of embodiment 101, wherein the kit comprises instructions for use of the liquid pharmaceutical composition.

SEQUENCE LISTING

```
Sequence total quantity: 1
SEQ ID NO: 1           moltype = AA  length = 9
FEATURE                Location/Qualifiers
source                 1..9
                       mol_type = protein
                       organism = synthetic construct
SITE                   1
                       note = 3-mercaptopropionic acid
SITE                   8
                       note = D-Arginine
SITE                   9
                       note = Amidated Glycine
SEQUENCE: 1
XYFQNCPRG                                                                9
```

What is claimed is:

1. A liquid pharmaceutical composition comprising
   a) desmopressin acetate, wherein desmopressin acetate is present in an amount of from about 0.01 mg/mL to about 0.1 mg/mL;
   b) a two-component, dual-functional, preservative-buffer system that comprises sodium benzoate and benzoic acid, wherein the two-component, dual-functional, preservative-buffer system provides a pH of the liquid pharmaceutical composition that is about 5.0; and
   c) water;
   wherein the liquid pharmaceutical composition is an oral solution.

2. The liquid pharmaceutical composition of claim 1, wherein desmopressin acetate is present in an amount from of about 0.03 mg/mL to about 0.07 mg/mL.

3. The liquid pharmaceutical composition of claim 1, wherein desmopressin acetate is present in an amount of about 0.05 mg/mL.

4. The liquid pharmaceutical composition of claim 1, wherein benzoic acid is present in an amount of from about 0.005% w/v to about 0.1% w/v.

5. The liquid pharmaceutical composition of claim 1, wherein benzoic acid is present in an amount of from about 0.02% w/v to about 0.05% w/v.

6. The liquid pharmaceutical composition of claim 1, wherein sodium benzoate is present in an amount of from about 0.01% w/v to about 0.6% w/v.

7. The liquid pharmaceutical composition of claim 1, wherein sodium benzoate is present in an amount of from about 0.15% w/v to about 0.32% w/v.

8. The liquid pharmaceutical composition of claim 1, wherein benzoic acid and sodium benzoate are present in an amount of from about 0.25% w/v to about 0.35% w/v.

9. The liquid pharmaceutical composition of claim 1, wherein the liquid pharmaceutical composition further comprises a preservative, and wherein the preservative comprises an antimicrobial agent, a chelating agent, an antioxidant, or a combination thereof.

10. The liquid pharmaceutical composition of claim 9, wherein the preservative comprises a paraben or mixture of parabens.

11. The liquid pharmaceutical composition of claim 1, wherein the liquid pharmaceutical composition has a pH that is about 5.0 after stored at 40° C.±2° C. and 75±5% RH for at least 6 months.

12. The liquid pharmaceutical composition of claim 1, comprising:
    a) desmopressin acetate in an amount of from about 0.01 mg/mL to about 0.1 mg/mL;
    b) sodium benzoate in an amount of from about 0.18% w/v to about 0.4% w/v;
    c) benzoic acid in an amount of from about 0.02% w/v to about 0.1% w/v; and
    d) water.

13. The liquid pharmaceutical composition of claim 1, comprising:
    a) desmopressin acetate in an amount of from about 0.025 mg/mL to about 0.075 mg/mL;
    b) sodium benzoate in an amount of from about 0.2% w/v to about 0.35% w/v;
    c) benzoic acid in an amount of from about 0.03% w/v to about 0.04% w/v; and
    d) water.

14. The liquid pharmaceutical composition of claim 1, comprising:
    a) desmopressin acetate in an amount of about 0.05 mg/mL;
    b) sodium benzoate in an amount of about 0.285% w/v;
    c) benzoic acid in an amount of about 0.034% w/v; and
    d) water.

15. The liquid pharmaceutical composition of claim 1, consisting essentially of:
    a) desmopressin acetate in an amount of about 0.05 mg/ml;
    b) sodium benzoate in an amount of about 0.285% w/v;
    c) benzoic acid in an amount of about 0.034% w/v; and
    d) water.

16. The liquid pharmaceutical composition of claim 1, consisting of
    a) desmopressin acetate in an amount of about 0.05 mg/mL;
    b) sodium benzoate in an amount of about 0.285% w/v;
    c) benzoic acid in an amount of about 0.034% w/v; and
    d) water.

17. The liquid pharmaceutical composition of claim 1, wherein the liquid pharmaceutical composition is ready-to-use without dilution or addition of any further components to the liquid pharmaceutical composition.

18. The liquid pharmaceutical composition of claim 1, wherein the liquid pharmaceutical composition contains no more than 5% wt of total impurities and not more than 1% wt of each of the following impurities: [Asp$^5$] desmopressin, [Glu$^4$] desmopressin, [Gly$^t$OH] desmopressin, [L-Arg$^8$] desmopressin, [Gln$^4$ (Acm)] desmopressin, [Asn$^5$ (Acm)] desmopressin, and [Gly$^9$N (CH3)$^2$] desmopressin after stored at 40° C.±2° C. and 75±5% RH humidity for 6 months, wherein the amount of impurities is determined according to High-performance liquid chromatography (HPLC) method.

19. The liquid pharmaceutical composition of claim 1, wherein the liquid pharmaceutical composition retains at least 90% wt of the initial desmopressin acetate amount after stored at 40° C.±2° C. and 75±5% RH for 6 months, wherein the desmopressin acetate amount is determined according to High-performance liquid chromatography (HPLC) method.

20. The liquid pharmaceutical composition of claim 1, wherein the liquid pharmaceutical composition exhibits a bioavailability that is bioequivalent to a reference oral tablet composition comprising desmopressin acetate, when measured as the total area under the curve (AUC) after oral administration or when measured as Cmax after oral administration.

21. A direct dosing device comprising the liquid pharmaceutical composition of claim 1.

22. A kit comprising a package enclosing the liquid pharmaceutical composition of claim 1.

* * * * *

UNITED STATES PATENT AND TRADEMARK OFFICE
CERTIFICATE OF CORRECTION

PATENT NO. : 12,214,010 B2
APPLICATION NO. : 18/625923
DATED : February 4, 2025
INVENTOR(S) : Yu-Hsing Tu et al.

It is certified that error appears in the above-identified patent and that said Letters Patent is hereby corrected as shown below:

In the Claims

Claim 1, Column 115, Line 1:
comprising

Should be corrected to:
comprising:

Claim 2, Column 115, Lines 16-17:
from of

Should be corrected to:
of from

Claim 15, Column 116, Line 16:
mg/ml;

Should be corrected to:
mg/mL;

Claim 16, Column 116, Line 21:
consisting of

Should be corrected to:
consisting of:

Claim 18, Column 116, Line 35:
Gly'OH

Signed and Sealed this
Eleventh Day of March, 2025

Coke Morgan Stewart
*Acting Director of the United States Patent and Trademark Office*

Should be corrected to:
Gly$^9$OH